(12) United States Patent
Tokuyasu et al.

(10) Patent No.: US 7,521,496 B2
(45) Date of Patent: Apr. 21, 2009

(54) ORGANOPHOSPHORUS COMPOUND HAVING PHOSPHATE-PHOSPHONATE BOND, AND FLAME-RETARDANT POLYESTER FIBER AND FLAME-RETARDANT POLYURETHANE RESIN COMPOSITION EACH CONTAINING THE SAME

(75) Inventors: Noriaki Tokuyasu, Tokai (JP); Kazuo Fujimoto, Handa (JP); Manabu Hirata, Handa (JP)

(73) Assignee: Daihachi Chemical Industry Co., Ltd., Osaka (JP)

(*) Notice: Subject to any disclaimer, the term of this patent is extended or adjusted under 35 U.S.C. 154(b) by 427 days.

(21) Appl. No.: 10/559,012

(22) PCT Filed: Jun. 4, 2004

(86) PCT No.: PCT/JP2004/007839

§ 371 (c)(1),
(2), (4) Date: Mar. 17, 2006

(87) PCT Pub. No.: WO2004/108736

PCT Pub. Date: Dec. 16, 2004

(65) Prior Publication Data

US 2006/0167145 A1    Jul. 27, 2006

(30) Foreign Application Priority Data

Jun. 9, 2003    (JP) .............................. 2003-164437

(51) Int. Cl.
*C08K 5/527*    (2006.01)
(52) U.S. Cl. ...................... 524/116; 524/123; 524/127
(58) Field of Classification Search ................ 524/123, 524/127, 116
See application file for complete search history.

(56) References Cited

U.S. PATENT DOCUMENTS

| 3,042,699 A | 4/1962 | Birum |
| 3,060,008 A | 10/1962 | Stange ......................... 44/69 |
| 4,407,765 A | 10/1983 | Hardy ......................... 260/970 |
| 4,416,877 A | 11/1983 | Bentzen et al. ............. 424/204 |
| 4,697,030 A | 9/1987 | Hardy et al. ................ 558/163 |
| 5,821,554 A * | 10/1998 | Harada et al. ........... 252/182.24 |
| 2006/0009423 A1 * | 1/2006 | Niesor et al. ................ 514/130 |

FOREIGN PATENT DOCUMENTS

| BE | 634428 A | 11/1983 |
| JP | 57-137377 | 8/1982 |
| JP | 2000-328450 | 5/1999 |
| WO | WO 92/22559 | 12/1992 |
| WO | WO 03/070179 A | 8/2003 |

OTHER PUBLICATIONS

Moskva, et al., Zhurnal Obshchei Khimii (1987), 57(12), 2794-4); in Russian; English abstract provided.
A. Tromelin et al., "α Cétophosphonates et Esters Cycliques D'Hydroxyméthylénes Diphosphonates Syntheses, Structures et Hydrolyse", *Phosphorus and Sulfur*, vol. 27, pp. 301-312, 1986, Gordon and Breach, Science Publishers, Inc., UK.
International Search Report for International Application No. PCT/JP2004/007839, in English and Japanese languages, 6 pages.
Hammerschmidt, F., "Neuartige synthetische Aspekte der Phosphonal-Phosphat-Umlagerung, 2. Mitt", *Monatshefte fuer Chernie*, Apr. 21, 1980, 1015-1023. 111, Springer-Verlag. Universitat Wien, Osterreich.
Maier, L. Organic Phosphorous Compounds 61 Esterification and Chlorination of Nitrito-tri(methylene-phosphonic acid), N (CH2PO3H2)3, and Hydroxyethylidenediphosphonic Acid, H2O3PC (OH) (CH3)PO3H2, and the Corresponding Esters), *Helvetica Chimca Acta*, 1973, 1257-1266, vol. 56, No. 4, Monsanto Research S.A., Zurich, Switzerland.
International Search Report for PCT/JP2004/007839 mailed Aug. 22, 2008.

* cited by examiner

*Primary Examiner*—Peter Szekely
(74) *Attorney, Agent, or Firm*—Ivor R. Elrifi, Esq.; Mintz Levin Cohn Ferris Glovsky and Popeo PC

(57) ABSTRACT

A phosphate-phosphonate compound which is lowly volatile, has a high phosphorus content, and does not influence various properties of a product when used as a material therefor. It is reduced in environmental burden in view of suitability for recycling and contains no halogen atoms including chlorine and bromine. The phosphorus compound has a phosphate-phosphonate bond within the molecule and has a specific ring structure. Because of this, the compound has excellent flame retardancy. Addition of the phosphate-phosphonate compound as a flame retardant for polyurethanes or polyesters imparts satisfactory plasticity and flame retardancy. The flame retardant is reduced in the exertion of adverse influences on the material properties of, in particular, polyurethane foams, polyester fibers, and the like.

45 Claims, 49 Drawing Sheets

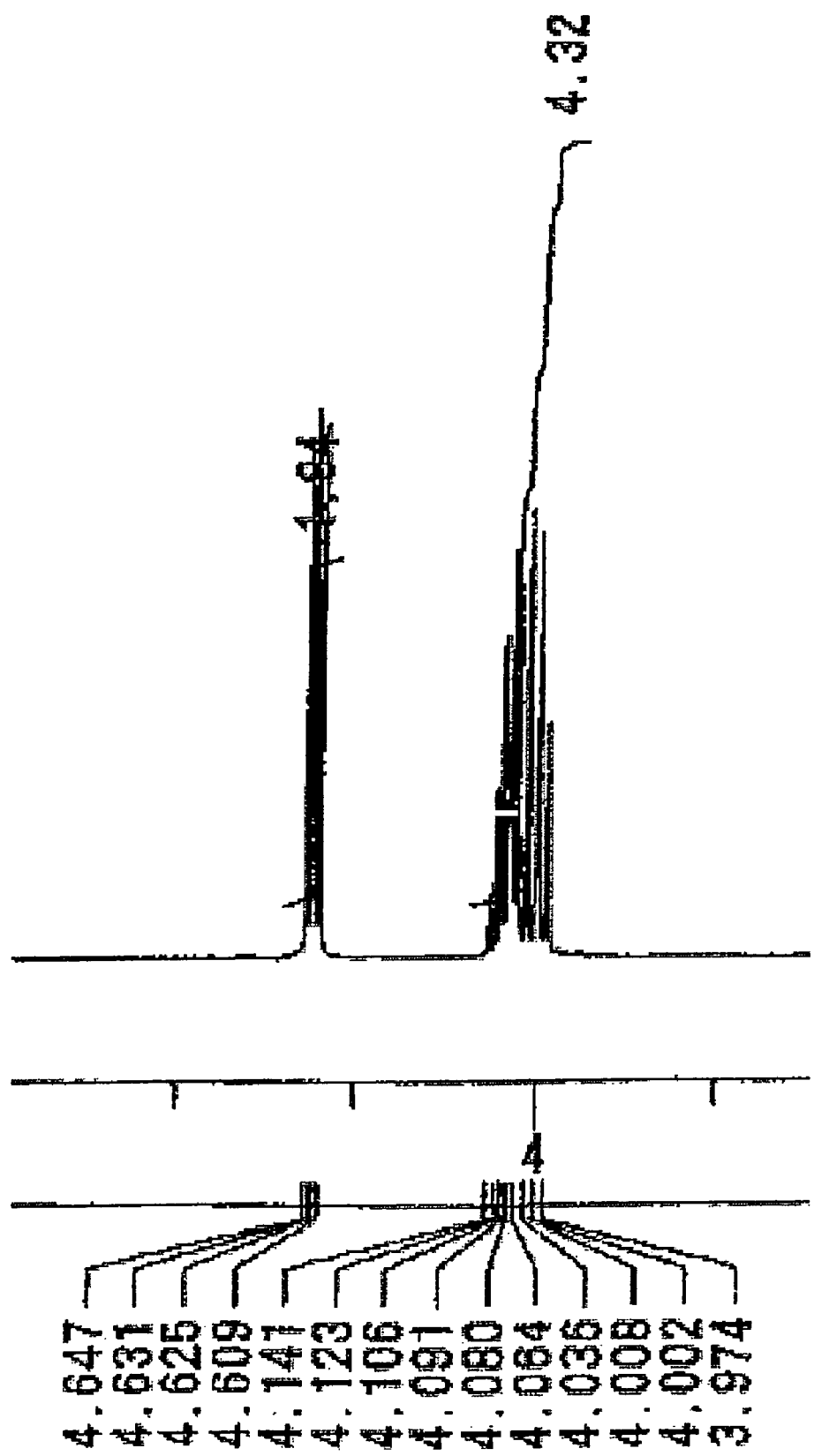

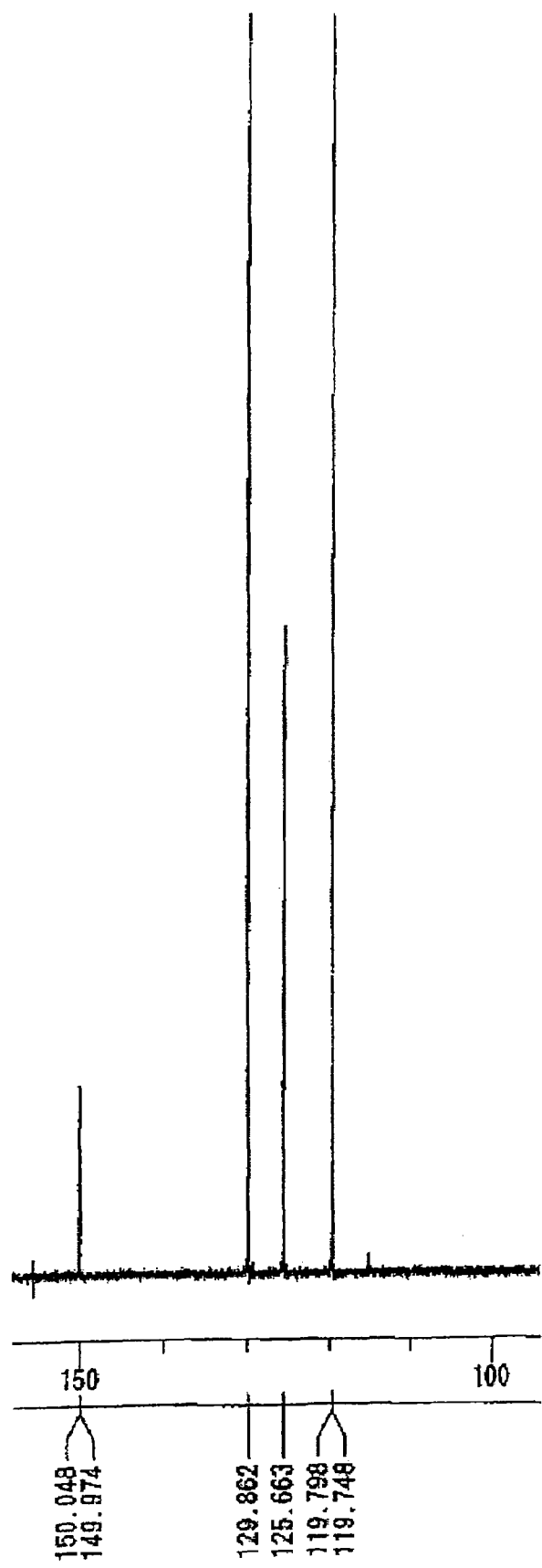

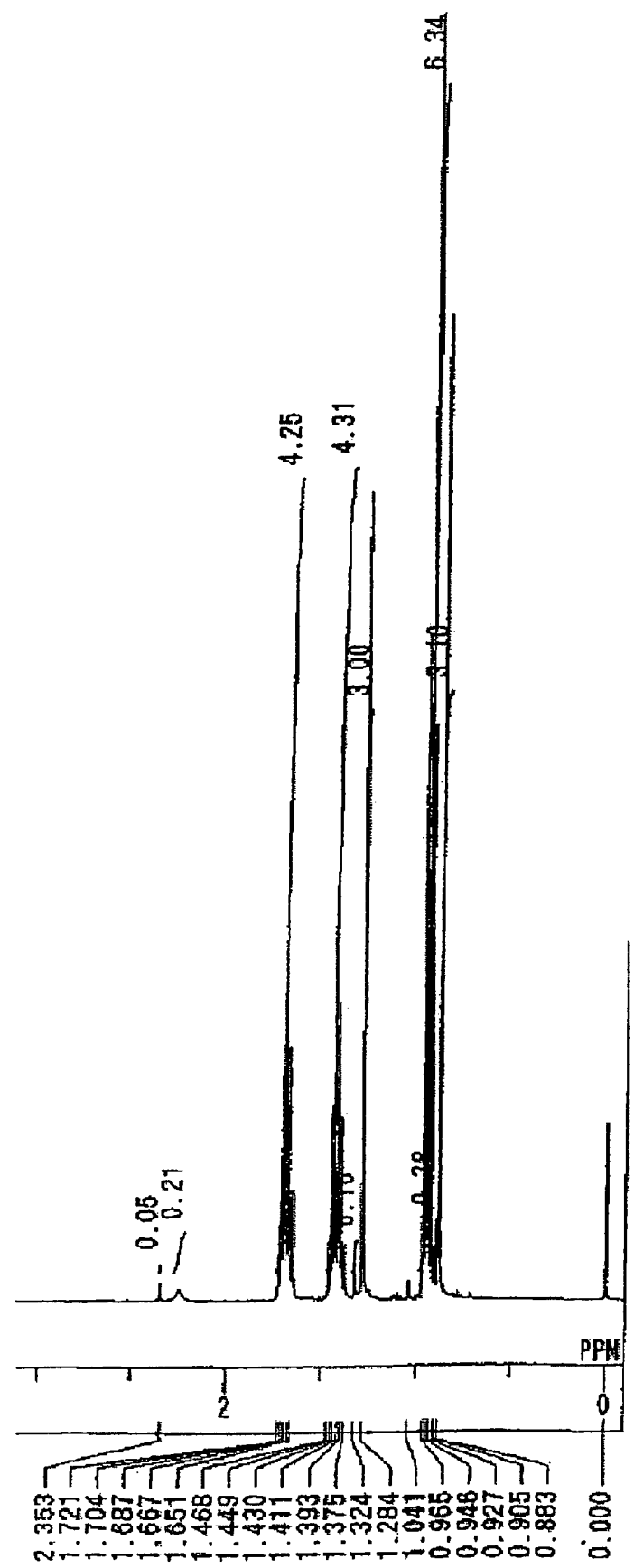

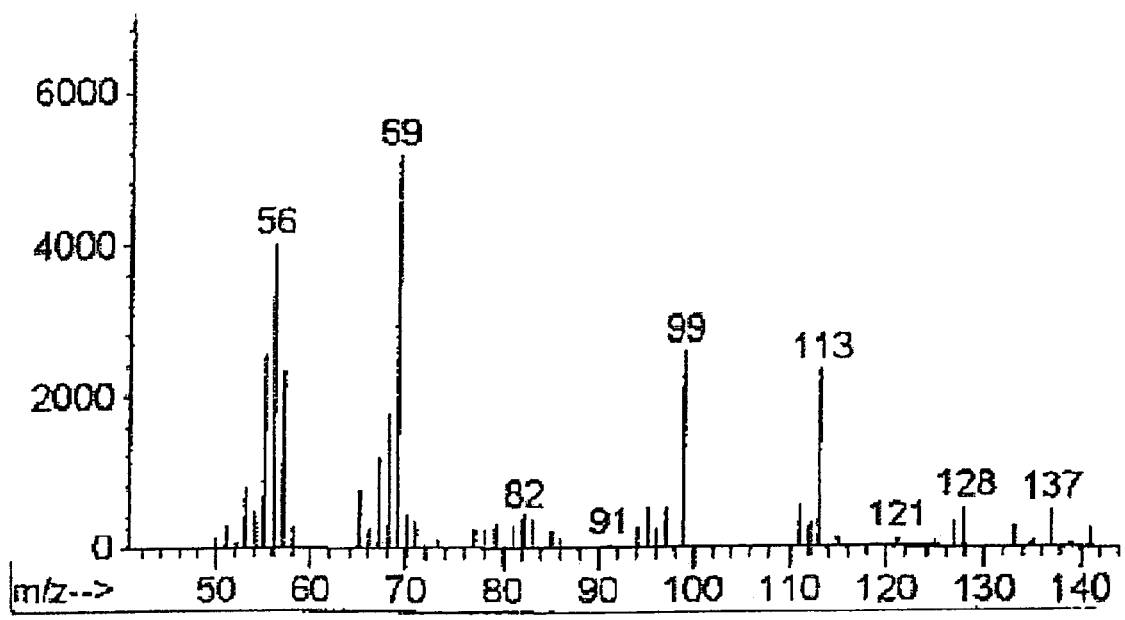

FIG.13A

```
Mon Apr 12 11:07:53 2004
PEAK              38
MXINT      39.5799561
RESOL       0.2439453 HZ
RESOL       0.0006102 PPM
EXREF       0.0000000 PPM
OBS         -7857.48 HZ
ABOBS   399790.9062500 KHZ
NGAIN             1
COMNT  TF-I-DPI8
```

| NO. | PPM | INT(%) | FREQU(HZ) | POSITION | BAR GRAPH |
|---|---|---|---|---|---|
| 1 | 7.38568 | 4.01189 | 2952.714 | 12193 | |
| 2 | 4.28655 | 14.76097 | 1713.716 | 17272 | ++ |
| 3 | 4.26031 | 16.52904 | 1703.226 | 17315 | +++ |
| 4 | 4.10594 | 2.58189 | 1641.508 | 17568 | |
| 5 | 4.09251 | 5.04667 | 1636.141 | 17590 | + |
| 6 | 4.08153 | 7.65801 | 1631.750 | 17608 | + |
| 7 | 4.06810 | 23.17965 | 1626.383 | 17630 | ++++ |
| 8 | 4.05468 | 33.43100 | 1621.017 | 17652 | +++++ |
| 9 | 4.04065 | 19.34356 | 1615.406 | 17675 | +++ |
| 10 | 4.03699 | 18.05576 | 1613.942 | 17681 | +++ |
| 11 | 4.02234 | 8.06413 | 1608.088 | 17705 | + |
| 12 | 4.01197 | 5.69927 | 1603.940 | 17722 | + |
| 13 | 3.99732 | 2.96177 | 1598.086 | 17746 | |
| 14 | 3.89420 | 10.30257 | 1556.859 | 17915 | ++ |
| 15 | 3.86674 | 9.49121 | 1545.881 | 17960 | + |
| 16 | 3.83745 | 10.11642 | 1534.172 | 18008 | ++ |
| 17 | 3.81000 | 9.05709 | 1523.195 | 18053 | + |
| 18 | 1.79944 | 64.63757 | 719.395 | 21348 | +++++++++++ |
| 19 | 1.76038 | 64.36422 | 703.782 | 21412 | +++++++++++ |
| 20 | 1.59563 | 11.33837 | 637.917 | 21682 | ++ |
| 21 | 1.58099 | 10.00955 | 632.062 | 21706 | ++ |
| 22 | 1.44858 | 5.45621 | 579.126 | 21923 | + |
| 23 | 1.42966 | 12.12356 | 571.564 | 21954 | ++ |
| 24 | 1.41441 | 19.12524 | 565.465 | 21979 | +++ |
| 25 | 1.39854 | 19.05975 | 559.123 | 22005 | +++ |
| 26 | 1.38207 | 14.77763 | 552.536 | 22032 | ++ |
| 27 | 1.36437 | 13.08113 | 545.462 | 22061 | ++ |
| 28 | 1.31190 | 61.82702 | 524.482 | 22147 | +++++++++++ |
| 29 | 1.30458 | 61.30605 | 521.555 | 22159 | +++++++++++ |
| 30 | 1.28627 | 80.05070 | 514.237 | 22189 | ++++++++++++++ |
| 31 | 1.06843 | 1.57033 | 427.148 | 22546 | |
| 32 | 1.04098 | 1.57656 | 416.171 | 22591 | |
| 33 | 0.93846 | 45.85678 | 375.188 | 22759 | +++++++++ |
| 34 | 0.91955 | 100.00000 | 367.626 | 22790 | +++++++++++++++++++ |
| 35 | 0.90063 | 95.10282 | 360.063 | 22821 | +++++++++++++++++++ |
| 36 | 0.88416 | 30.93235 | 353.477 | 22848 | ++++++ |
| 37 | 0.85792 | 73.03387 | 342.987 | 22891 | ++++++++++++++ |
| 38 | -0.00122 | 1.32142 | -0.488 | 24299 | |

FIG.14A

```
Thu Apr 08 12:50:56 2004
PEAK              32
MXINT     192.5510712
RESOL       0.8292816 HZ
RESOL       0.0082494 PPM
EXREF      77.0000000 PPM
OBS          -25951.57 HZ
ABOBS   100537.1015625 KHZ
NGAIN              1
COMNT   TF-I-OPI8
```

| NO. | PPM | INT(%) | FREQU(HZ) | POSITION | BAR GRAPH |
|---|---|---|---|---|---|
| 1 | 81.35565 | 6.59461 | 8178.730 | 18644 | + |
| 2 | 81.27316 | 6.58503 | 8170.437 | 18654 | + |
| 3 | 79.57379 | 6.41876 | 7999.599 | 18860 | + |
| 4 | 79.49130 | 6.14781 | 7991.306 | 18870 | + |
| 5 | 77.68470 | 34.33687 | 7809.687 | 19089 | +++++ |
| 6 | 77.61870 | 37.46143 | 7803.052 | 19097 | ++++++ |
| 7 | 77.31347 | 16.28221 | 7772.368 | 19134 | +++ |
| 8 | 77.00000 | 16.70792 | 7740.854 | 19172 | +++ |
| 9 | 76.67828 | 17.36732 | 7708.511 | 19211 | +++ |
| 10 | 68.72591 | 19.31449 | 6909.055 | 20175 | +++ |
| 11 | 68.70117 | 29.15245 | 6906.567 | 20178 | +++++ |
| 12 | 68.65167 | 23.28378 | 6901.591 | 20184 | ++++ |
| 13 | 68.62692 | 28.89265 | 6899.103 | 20187 | +++++ |
| 14 | 40.13371 | 23.43668 | 4034.664 | 23641 | ++++ |
| 15 | 40.10896 | 35.67627 | 4032.176 | 23644 | +++++++ |
| 16 | 40.06771 | 25.36395 | 4028.030 | 23649 | +++++ |
| 17 | 40.05121 | 33.98823 | 4026.371 | 23651 | ++++++ |
| 18 | 31.87612 | 16.95840 | 3204.524 | 24642 | +++ |
| 19 | 31.81837 | 16.24236 | 3198.719 | 24649 | +++ |
| 20 | 29.75604 | 48.65124 | 2991.392 | 24899 | +++++++++ |
| 21 | 29.73129 | 71.72946 | 2988.904 | 24902 | ++++++++++++++ |
| 22 | 28.68363 | 39.21879 | 2883.581 | 25029 | +++++++ |
| 23 | 28.62588 | 56.12524 | 2877.776 | 25036 | +++++++++++ |
| 24 | 23.33805 | 55.08837 | 2346.188 | 25677 | +++++++++++ |
| 25 | 23.15657 | 52.36468 | 2327.943 | 25699 | ++++++++++ |
| 26 | 23.10707 | 52.08830 | 2322.967 | 25705 | ++++++++++ |
| 27 | 22.76885 | 100.00000 | 2288.965 | 25746 | ++++++++++++++++++++ |
| 28 | 21.69644 | 39.07910 | 2181.155 | 25876 | +++++++ |
| 29 | 20.02182 | 29.74919 | 2012.805 | 26079 | +++++ |
| 30 | 13.84307 | 72.41095 | 1391.651 | 26828 | ++++++++++++++ |
| 31 | 10.74956 | 41.32890 | 1080.660 | 27203 | ++++++++ |
| 32 | 10.71657 | 64.65044 | 1077.343 | 27207 | ++++++++++++ |

ORGANOPHOSPHORUS COMPOUND HAVING PHOSPHATE-PHOSPHONATE BOND, AND FLAME-RETARDANT POLYESTER FIBER AND FLAME-RETARDANT POLYURETHANE RESIN COMPOSITION EACH CONTAINING THE SAME

BACKGROUND OF THE INVENTION

1. Field of the Invention

The present invention relates to a novel phosphorus compound having a phosphate-phosphonate bond in one molecule. As used herein, the term "phosphate-phosphonate bond" refers to a bond between a phosphorus atom and another phosphorus atom which is provided by a linking group formed of an alkylene, which may have one or more substituents, and an oxygen atom. In this specification, a compound having a phosphate-phosphonate bond in one molecule is referred to as a "phosphate-phosphonate compound" for the sake of simplicity.

Such a compound is useful as a flame retardant agent, especially, as a flame retardant agent for a resin material.

In another aspect of the invention, the present invention relates to a flame retardant polyester fiber which contains, as a flame retardant agent, an organic phosphorus compound having a phosphate-phosphonate bond in one molecule and is superb in flame retarding property, thermal resistance, and hydrolysis resistance. More specifically, the present invention relates to a flame retardant polyester fiber which is flame-retarded by the phosphorus compound and thus is less adversely influenced regarding various properties of the fiber, does not contain halogen, and is durable against washing.

In still another aspect of the invention, the present invention relates to a flame retardant polyurethane resin composition. In more detail, the present invention relates to a flame retardant polyurethane resin composition which contains, as a flame retardant agent, a specific organic phosphorus compound having a phosphate-phosphonate bond in one molecule, and is superb in flame retarding property, thermal resistance, and volatilization resistance.

2. Description of the Related Art

Phosphorus compounds are generally used in various fields as multi-functional compounds, and various types of phosphorus compounds have been developed. Among those functions, phosphorus compounds are conventionally known as being useful as a flame retardant agent. Phosphorus compounds can be used as a flame retardant agent for a wide range of resins, for example, thermoplastic resins including polycarbonate, ABS resins, and PPE; thermosetting resins including polyurethane resins, epoxy resins, and phenol resins; and resins or fibers of polyester including polyethylene terephthalate, and polybutylene terephthalate.

The flame retarding property of a phosphorus compound generally relies on the phosphorus content thereof. When a phosphorus compound is used for a resin in an amount which is sufficient to provide an intended level of flame retarding property, the physical properties of the resin may significantly be lowered. Therefore, a phosphorus compound having a high phosphorus content is desired in order to provide a sufficient level of flame retarding property with a smaller amount of phosphorus compound.

Further, a flame retardant agent for a resin is exposed to a very high temperature for kneading or molding the resin. Accordingly, a phosphorus compound having a high stability at a high temperature is desired.

Among the above-mentioned resin and fiber materials, polyester fibers are used in various fields including clothing, interior products, filing cotton, non-woven cloth, and materials for industrial use, for its superb dynamic characteristics and ease of processing. The polyester fiber products used for interior decoration of hotels, hospitals, movie theaters and the like are strictly restricted by the Fire Services Act, in order to minimize damages of fires caused by matches, cigarettes and the like. As the awareness of disaster prevention of the general public has been increased recently, development of flame retardant polyester fiber products has been desired in order to create a highly safe and comfortable living environment.

The flame retarding property of a phosphorus compound generally relies on the phosphorus content thereof. Namely, in general, as the phosphorus content is higher, the flame retarding property is higher. This general principle is not necessarily true for flame-retarded polyester fibers.

For example, even when a phosphorus compound having a high phosphorus content is used, the flame-retarded polyester fiber may have the phosphorus compound merely adhering to the surface of the fiber, without penetrating deep into the fiber. Clothing or the like, which is produced of the flame-retarded fiber in such a state, is not continuously provided with the intended level of flame retarding property since the phosphorus compound is easily detached from the fiber by washing.

Conversely, even a phosphorus compound having a low phosphorus content can provide an intended level of flame retarding property if the phosphorus compound fully penetrates into the polyester fiber and strongly adheres to the polyester fiber physically.

Accordingly, a phosphorus compound desired in the technical field of polyester fibers has a high phosphorus content such that the amount of phosphorus compound can be reduced to provide a sufficient level of flame retarding property. In addition, a phosphorus compound which is not easily detached from the polyester fiber is desired in the technical field of polyester fiber.

Polyurethane resins are mainly used in various fields of products for daily life, including automobile upholstery, furniture, materials for electrical devices, and building materials, for their characteristics of being low cost, lightweight, and easy to shape. Polyurethane resins are mostly used as polyurethane foams. However, polyurethane resins, which are polymeric organic compounds, are inflammable and may possibly cause an uncontrollable combustion once ignited. A fire caused in a living environment may lead to disaster affecting people's lives. From this point of view, the polyurethane foam production industry has made efforts to avoid fires by introducing flame retardation technology into the foams. Today, parts of the products formed of polyurethane foams, including automobile upholstery, furniture, and materials for electrical devices, are legally required to be flame retardant. Such legal regulations are provided by, for example, the UL Standards for electric products and the FMVSS-302 for automobiles in the United States.

In general, a polyurethane resin can be flame-retarded by adding a flame retardant agent when foaming the polyurethane resin. When a flame-retardant agent is added to the polyurethane resin in an amount which is sufficient to provide an intended level of flame retarding property, the physical properties of the polyurethane resin may be significantly lowered. Accordingly, a phosphorus compound having a high phosphorus content is desired in order to provide a sufficient level of flame retarding property with a smaller amount of phosphorus compound. However, use of a phosphorus compound having a high phosphorus content does not necessarily guarantee a high flame retarding property or various physical properties required of the polyurethane resin composition.

A type of flame retardant agent, which has increasingly been used recently, foams and carbonizes the material to be flame-retarded at the time of combustion to form a char, and thus cuts off oxygen and provides a flame retardation effect. Such a property of the flame retardant agent is referred to as intumescent. The effect is not controlled only by the phosphorus content, but often relies on the molecular structure of the flame retardant agent. When the flame retardant agent fulfills the required conditions regarding the phosphorus content and molecular structure, a polyurethane foam having a higher level of flame retarding property can be provided by the synergistic effect. In foaming polyurethane, as the foaming scale is increased, the temperature of the heat accumulated internally is increased. Thus, a phosphorus compound having a high thermal stability at such a high temperature is desired.

Phosphorus compounds are roughly classified by structure into, for example, phosphate, phosphonate, phosphinate, phosphate, phosphonite, phosphinite, phosphine oxide, and phosphine. There are also phosphorus compounds having a plurality of different types of bonds in one molecule. A phosphate-phosphonate compound is one example thereof. More specifically, known examples of phosphate-phosphonate compounds include phosphate-phosphonate compounds containing a halogen atom such as chlorine, bromine or the like in the molecule, phosphate-phosphonate compounds containing an alcoholic hydroxyl group in the molecule, and phosphate-phosphonate compounds containing a short alkyl group such as, for example, an ethyl group.

These phosphate-phosphonate compounds are described in, for example, the following documents:

Japanese Laid-Open Publication No. 2000-328450 (pages 2 to 6);
Japanese Laid-Open Publication No. 57-137377 (pages 1 to 10);
U.S. Pat. No. 4,697,030 (pages 2 to 9);
Zhurnal Obshchei Kimii (1987), 57(12), 2793-4; and
U.S. Pat. No. 3,060,008 (pages 1 to 3).

For example, Japanese Laid-Open Publication No. 2000-328450 discloses a technology for using a phosphate-phosphonate compound containing a halogen atom to flame-retard a metha-type aromatic polyamide fiber. Japanese Laid-Open Publication No. 57-137377 discloses a technology for using a compound containing a halogen atom such as hexabromocyclododecane to flame-retard a fiber.

However, use of these compounds containing halogen has problems in that when the fiber is, for example, burned, the decomposition of the phosphorus compound used as the flame retardant agent generates gas harmful to the human body such as hydrogen halides or the like, corrodes the incinerator, or generates dioxin, which is more harmful than hydrogen halides.

U.S. Pat. No. 4,697,030 discloses a phosphate-phosphonate compound containing an alcoholic hydroxyl group, and examples of using a phosphate-phosphonate compound for a polyester fiber and a polyurethane foam.

However, a phosphate-phosphonate compound having an alcoholic hydroxyl group is not superb in water resistance. For example, when a phosphate-phosphonate compound having an alcoholic hydroxyl group is added to a polyester fiber, as the product formed of the fiber and the compound is washed repeatedly, the phosphate-phosphonate compound is gradually eluted to the washing water since the compound has affinity with water. As a result, the flame retarding property of the fiber is easily lowered.

This problem is solved by using a method of reacting the above-mentioned phosphorus compound when synthesizing polyester and thus incorporating the phosphorus compound into the backbone structure of the polyester. Such a reaction cannot be performed by processing manufacturers, which use a method of simply purchasing a polyester fiber and allowing a flame retardant agent to be absorbed into the polyester fiber (post-processing method). In other words, there is a limit in the manner of using the phosphorus compound.

A polyurethane foam is generally produced by reacting two types of hydroxyl groups, i.e., hydroxyl groups of polyol and a hydroxyl group of water as a foaming agent, with isocyanate groups of polyisocyanate. When this phosphorus compound is used for a polyurethane foam, there occurs a necessity of controlling the reaction of these three types of hydroxyl groups having different reactivities with the is isocyanate group. Due to the difficulty in controlling the reaction, it is very difficult with the conventional compositions to obtain a foam which sufficiently fulfills various physical properties required of the foam. Even if a foam which is superb in various physical properties is obtained, the range of ratios of materials and a catalyst usable for forming a foam is very narrow, and it is disadvantageously required to perform highly strict control in the actual production process of the foam.

A compound described in U.S. Pat. No. 4,697,030 is inferior in hydrolysis resistance and has a problem in storage stability. For example, for dyeing or flame-retarding a polyester fiber, the compound is used in an emulsified state. Since the emulsification stability of the compound is inferior, it is likely that the color is made uneven and oil spots are generated when the polyester fiber is heated to be processed.

Zhurnal Obshchei Kimii (1987), 57(12), 2793-4, discloses a phosphate-phosphonate compound having four ethoxy groups (C$_2$H$_5$O—) in the molecule.

However, this compound is relatively volatile and has the following disadvantages. When this compound is used for, for example, a polyurethane foam, a fogging phenomenon is likely to occur when the resultant polyurethane foam is exposed to a high temperature. As result, it is likely that the flame retarding property of the resultant polyurethane foam is lowered, or gas harmful to the human body is generated.

Zhurnal Obshchei Khimii (1987), 57(12), 2793-4, does not specifically describe or suggest using a phosphorus compound described therein as a flame retardant agent of a polyurethane resin or a polyester fiber.

U.S. Pat. No. 3,060,008 discloses use of a phosphorus compound for uses other than a flame retardant agent; i.e., a technology of adding a compound represented by the following formula (V) to a fuel of engine.

(V)

(In the formula, R is either n-butyl, iso-butyl, or sec-butyl.)

However, U.S. Pat. No. 3,060,008 does not specifically describe or suggest a phosphorus compound having a cyclic structure in which two R's are combined to each other.

U.S. Pat. No. 3,060,008 does not specifically describe or suggest using a phosphorus compound described therein as a flame retardant agent of a polyurethane resin or a polyester fiber.

SUMMARY OF THE INVENTION

The present inventors performed active research in order to solve the above-described problems, and as a result, found that a phosphate-phosphonate compound represented by formula (I) or (III) solves the above-described problems and completed the present invention.

The present inventors performed active research in order to solve the above-described problems, and as a result, found that when a specific phosphorus compound is used for a polyester fiber as a flame retardant agent, a flame retardant polyester fiber which is superb in thermal resistance and hydrolysis resistance of the flame retardant agent, and has superb physical properties as a fiber (e.g., flame retarding property, washing durability) is obtained and completed the present invention.

The present inventors performed active research in order to solve the above-described problems, and as a result, found that using a specific phosphorus compound as a flame retardant agent, a flame retardant polyurethane resin composition of excellent characteristics, which is superb in thermal resistance, does not deteriorate the urethane foam, does not generate scorch at the time of foaming, and provides a high level of flame retarding property to a resin, is obtained and completed the present invention.

According to the first aspect of the invention, the following phosphorus compound is provided.

(1) A compound represented by the following formula (I):

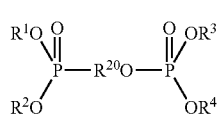
(I)

wherein, in formula (I), $R^1$, $R^2$, $R^3$ and $R^4$ are identical to or different from each other, and are:

a $C_{2-8}$ alkyl group having a straight or branched chain, a $C_{5-10}$ cycloalkyl group which may have one or more substituents, or a $C_{6-15}$ aryl group which may have one or more substituents; or $R^1$ and $R^2$ may be combined to become a $C_{2-9}$ alkylene group and form the following cyclic structure A together with the oxygen atoms and the phosphorus atom;

Cyclic structure A:

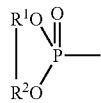

(in cyclic structure A, —$R^1$-$R^2$— is the $C_{2-9}$ alkylene group); or $R^3$ and $R^4$ may be combined to become a $C_{2-9}$ alkylene group and form the following cyclic structure B together with the oxygen atoms and the phosphorus atom;

Cyclic structure B:

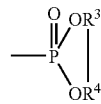

(in cyclic structure B, —$R^3$-$R^4$— is the $C_{2-9}$ alkylene group);

wherein:

the compound indispensably has at least one of cyclic structure A and cyclic structure B; and $R^{20}$ is a linking group having formula 67:

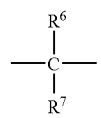
(Formula 67)

(in formula 67, $R^6$ and $R^7$ may be identical to or different from each other; are either hydrogen, a $C_{1-6}$ alkyl group, or $C_{6-11}$ aryl group; or $R^6$ and $R^7$ may be combined to become a $C_{4-10}$ alkylene group which may have one or more substituents, the $C_{4-10}$ alkylene group forming the following cyclic structure together with the carbon atom

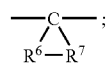;

and a total number of carbons of $R^6$ and $R^7$ is 0 to 12).

(2) A compound according to item (1), wherein $R^1$ and $R^2$ are combined to form the cyclic structure A and $R^3$ and $R^4$ are combined to form the cyclic structure B.

(3) A compound according to item (1), wherein $R^1$ and $R^2$ are combined to become an alkylene group represented by the following formula (II) and form the cyclic structure A, or $R^3$ and $R^4$ are combined to become an alkylene group represented by the following formula (II) and form the cyclic structure B.

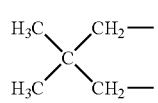
(II)

(4) A compound according to item (1), wherein $R^{20}$ is either a methylene group, a —CH(CH$_3$)— group, or a —C(CH$_3$)$_2$— group.

(5) A compound according to item (1), wherein at least one of $R^3$ and $R^4$ is a $C_{6-15}$ aryl group when the compound has the cyclic structure A, and at least one of $R^1$ and $R^2$ is a $C_{6-15}$ aryl group when the compound has the cyclic structure B.

(6) A compound represented by the following formula (III):

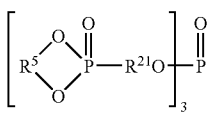
(III)

wherein, in formula (III), $R^5$ is a $C_{2-9}$ alkylene group, and $R^{21}$ is a linking group having formula 89:

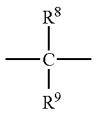
(Formula 89)

(in formula 89,
$R^8$ and $R^9$ may be identical to or different from each other; are either hydrogen, a $C_{1-6}$ alkyl group, or $C_{6-11}$ aryl group; or $R^8$ and $R^9$ may be combined to become a $C_{4-10}$ alkylene group which may have one or more substituents, the $C_{4-10}$ alkylene group forming the following cyclic structure together with the carbon atom

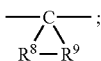

and
a total number of carbons of $R^8$ and $R^9$ is 0 to 12).
(7) A compound according to item (6), wherein $R^{21}$ is either a methylene group, a —CH(CH$_3$)— group, or a —C(CH$_3$)$_2$— group.
(8) A compound according to item (6), wherein $R^5$ is the following formula (IV).

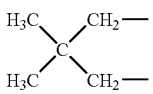
(IV)

Also according to the present invention, the following flame retardant agent, flame retardant polyester fiber, a flame retardant polyurethane resin composition, and the like are provided.
(9) A flame retardant agent for a resin formed of a compound represented by the following formula (I):

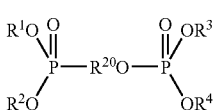
(I)

wherein, in formula (I),
$R^1$, $R^2$, $R^3$ and $R^4$ are identical to or different from each other, and are:
a $C_{2-8}$ alkyl group having a straight or branched chain,
a $C_{5-10}$ cycloalkyl group which may have one or more substituents, or a $C_{6-15}$ aryl group which may have one or more substituents; or
$R^1$ and $R^2$ may be combined to become a $C_{2-9}$ alkylene group and form the following cyclic structure A together with the oxygen atoms and the phosphorus atom;

Cyclic structure A:

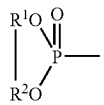

(in cyclic structure A, —$R^1$-$R^2$— is a $C_{2-9}$ alkylene group); or
$R^3$ and $R^4$ may be combined to become a $C_{2-9}$ alkylene group and form the following cyclic structure B together with the oxygen atoms and the phosphorus atom;

Cyclic structure B:

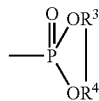

(in cyclic structure B, —$R^3$-$R^4$— is a $C_{2-9}$ alkylene group);
wherein:
the compound indispensably has at least one of cyclic structure A and cyclic structure B; and
$R^{20}$ is a linking group having formula 67:

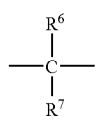
(Formula 67)

(in formula 67,
$R^6$ and $R^7$ may be identical to or different from each other; are either hydrogen, a $C_{1-6}$ alkyl group, or $C_{6-11}$ aryl group; or $R^6$ and $R^7$ may be combined to become a $C_{4-10}$ alkylene group which may have one or more substituents, the $C_{4-10}$ alkylene group forming the following cyclic structure together with the carbon atom

and
a total number of carbons of $R^6$ and $R^7$ is 0 to 12).
(10) A flame retardant agent for a resin formed of a compound represented by the following formula (III):

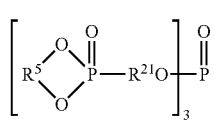
(III)

wherein, in formula (III), $R^5$ is a $C_{2-9}$ alkylene group, and $R^{21}$ is a linking group having formula 89:

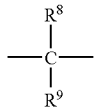

(Formula 89)

(in formula 89, $R^8$ and $R^9$ may be identical to or different from each other; are either hydrogen, a $C_{1-6}$ alkyl group, or $C_{6-11}$ aryl group; or $R^8$ and $R^9$ may be combined to become a $C_{4-10}$ alkylene group which may have one or more substituents, the $C_{4-10}$ alkylene group forming the following cyclic structure together with the carbon atom

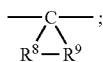

and a total number of carbons of $R^8$ and $R^9$ is 0 to 12).

(11) A flame retardant agent according to item (9), which is used for flame retardation of a polyester fiber.
(12) A flame retardant agent according to item (10), which is used for flame retardation of a polyester fiber.
(13) A polyester fiber processed with a flame retardant agent, the flame retardant agent being formed of a compound represented by the following formula (I):

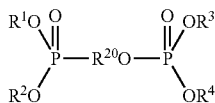

(I)

wherein, in formula (I), $R^1$, $R^2$, $R^3$ and $R^4$ are identical to or different from each other, and are:

a $C_{2-8}$ alkyl group having a straight or branched chain, a $C_{5-10}$ cycloalkyl group which may have one or more substituents, or a $C_{6-15}$ aryl group which may have one or more substituents; or $R^1$ and $R^2$ may be combined to become a $C_{2-9}$ alkylene group and form the following cyclic structure A together with the oxygen atoms and the phosphorus atom;

Cyclic structure A:

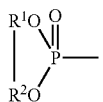

(in cyclic structure A, —$R^1$-$R^2$— is a $C_{2-9}$ alkylene group); or $R^3$ and $R^4$ may be combined to become a $C_{2-9}$ alkylene group and form the following cyclic structure B together with the oxygen atoms and the phosphorus atom;

Cyclic structure B:

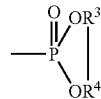

(in cyclic structure B, —$R^3$-$R^4$— is a $C_{2-9}$ alkylene group);

wherein:

the compound indispensably has at least one of cyclic structure A and cyclic structure B; and $R^{20}$ is a linking group having formula 67:

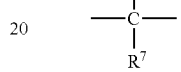

(Formula 67)

(in formula 67, $R^6$ and $R^7$ may be identical to or different from each other; are either hydrogen, a $C_{1-6}$ alkyl group, or $C_{6-11}$ aryl group; or $R^6$ and $R^7$ may be combined to become a $C_{4-10}$ alkylene group which may have one or more substituents, the $C_{4-10}$ alkylene group forming the following cyclic structure together with the carbon atom

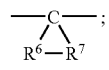

and a total number of carbons of $R^6$ and $R^7$ is 0 to 12).

(14) A polyester fiber according to item (13), wherein $R^1$ and $R^2$ of the flame retardant agent are combined to form the cyclic structure A and $R^3$ and $R^4$ of the flame retardant agent are combined to form the cyclic structure B.
(15) A polyester fiber according to item (13), wherein $R^1$ and $R^2$ of the flame retardant agent are combined to become an alkylene group represented by the following formula (II) and form the cyclic structure A, or $R^3$ and $R^4$ of the flame retardant agent are combined to become an alkylene group represented by the following formula (II) and form the cyclic structure B

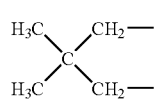

(II)

(16) A polyester fiber according to item (13), wherein $R^{20}$ of the flame retardant agent is either a methylene group, a —CH(CH$_3$)— group, or a —C(CH$_3$)$_2$— group.
(17) A polyester fiber according to item (13), wherein at least one of $R^3$ and $R^4$ is a $C_{6-15}$ aryl group when the flame retardant agent has the cyclic structure A, and at least one of $R^1$ and $R^2$ is a $C_{6-15}$ aryl group when the flame retardant agent has the cyclic structure B.
(18) A polyester fiber according to item (13), wherein a content of the flame retardant agent of the polyester fiber is 0.1 to 30% by weight with respect to the total weight of the polyester fiber including the flame retardant agent.

(19) A polyester fiber processed with a flame retardant agent, the flame retardant agent being formed of a compound represented by the following formula (III):

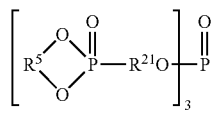

(III)

wherein, in formula (III), $R^5$ is a $C_{2-9}$ alkylene group, and $R^{21}$ is a linking group having formula 89:

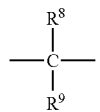

(Formula 89)

(in formula 89,
$R^8$ and $R^9$ may be identical to or different from each other; are either hydrogen, a $C_{1-6}$ alkyl group, or $C_{6-11}$ aryl group; or $R^8$ and $R^9$ may be combined to become a $C_{4-10}$ alkylene group which may have one or more substituents, the $C_{4-10}$ alkylene group forming the following cyclic structure together with the carbon atom

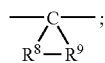

;

and
a total number of carbons of $R^8$ and $R^9$ is 0 to 12).

(20) A polyester fiber according to item (19), wherein $R^{21}$ of the flame retardant agent is either a methylene group, a —CH(CH$_3$)— group, or a —C(CH$_3$)$_2$— group.

(21) A polyester fiber according to item (19), wherein $R^5$ of the flame retardant agent is the following formula (IV).

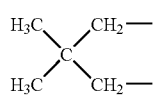

(IV)

(22) A polyester fiber according to item (19), wherein a content of the flame retardant agent of the polyester fiber is 0.1 to 30% by weight with respect to the total weight of the polyester fiber including the flame retardant agent.

(23) A method for flame-retarding a polyester fiber, comprising the step of processing the polyester fiber with a flame retardant agent according to item (11).

(24) A method for flame-retarding a polyester fiber, comprising the step of processing the polyester fiber with a flame retardant agent according to item (12).

(25) A flame retardant agent according to item (9), which is used for flame retardation of a polyurethane resin.

(26) A flame retardant agent according to item (10), which is used for flame retardation of a polyurethane resin.

(27) A flame retardant polyurethane resin composition, comprising (a) a flame retardant agent, (b) a polyol component, and (c) a polyisocyanate component, wherein the flame retardant agent is represented by the following formula (I):

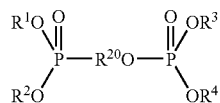

(I)

wherein, in formula (I),
$R^1$, $R^2$, $R^3$ and $R^4$ are identical to or different from each other, and are:
a $C_{2-8}$ alkyl group having a straight or branched chain,
a $C_{5-10}$ cycloalkyl group which may have one or more substituents, or
a $C_{6-15}$ aryl group which may have one or more substituents; or
$R^1$ and $R^2$ may be combined to become a $C_{2-9}$ alkylene group and form the following cyclic structure A together with the oxygen atoms and the phosphorus atom;

Cyclic structure A:

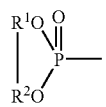

(in cyclic structure A, —$R^1$-$R^2$— is a $C_{2-9}$ alkylene group); or
$R^3$ and $R^4$ may be combined to become a $C_{2-9}$ alkylene group and form the following cyclic structure B together with the oxygen atoms and the phosphorus atom;

Cyclic structure B:

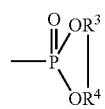

(in cyclic structure B, —$R^3$-$R^4$— is a $C_{2-9}$ alkylene group);
wherein:
the compound indispensably has at least one of cyclic structure A and cyclic structure B; and
$R^{20}$ is a linking group having formula 67:

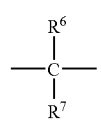

(Formula 67)

(in formula 67,
$R^6$ and $R^7$ may be identical to or different from each other; are either hydrogen, a $C_{1-6}$ alkyl group, or $C_{6-11}$ aryl group; or $R^6$ and $R^7$ may be combined to become a $C_{4-10}$ alkylene group which may have one or more substituents, the $C_{4-10}$ alkylene group forming the following cyclic structure together with the carbon atom

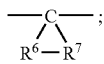

and a total number of carbons of $R^6$ and $R^7$ is 0 to 12).

(28) A composition according to item (27), further comprising (d) a catalyst, (e) a silicone foam stabilizer, and (f) a foaming agent.

(29) A composition according to item (27), wherein $R^1$ and $R^2$ of the flame retardant agent are combined to form the cyclic structure A and $R^3$ and $R^4$ of the flame retardant agent are combined to form the cyclic structure B.

(30) A composition according to item (27), wherein $R^1$ and $R^2$ of the flame retardant agent are combined to become an alkylene group represented by the following formula (II) and form the cyclic structure A, or $R^3$ and $R^4$ of the flame retardant agent are combined to become an alkylene group represented by the following formula (II) and form the cyclic structure B.

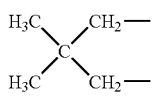
(II)

(31) A composition according to item (27), wherein $R^{20}$ of the flame retardant agent is either a methylene group, a —CH(CH$_3$)— group, or a —C(CH$_3$)$_2$— group.

(32) A composition according to item (27), wherein at least one of $R^3$ and $R^4$ is a $C_{6-15}$ aryl group when the flame retardant agent has the cyclic structure A, and at least one of $R^1$ and $R^2$ is a $C_{6-15}$ aryl group when the flame retardant agent has the cyclic structure B.

(33) A composition according to item (27), wherein the polyol component is selected from the group consisting of polyether polyol, polyester polyol, and polymer polyol.

(34) A composition according to item (27), wherein the polyisocyanate component is selected from the group consisting of tolylene diisocyanate (TDI) and diphenylmethane 4,4'-diisocyanate (MDI).

(35) A composition according to item (27), wherein a content of the flame retardant agent is 0.1 to 60 parts by weight with respect to 100 parts by weight of the polyol component.

(36) A composition according to item (27), further comprising, as an antioxidant, (g) a hydroquinone compound represented by the following general formula (VII) and/or trivalent organic phosphorus compound:

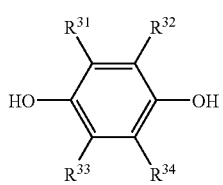
(VII)

(in the formula, $R^{31}$, $R^{32}$, $R^{33}$ and $R^{34}$ are each a hydrogen atom or a $C_{1-14}$ alkyl group).

(37) A flame retardant polyurethane resin composition, comprising (a) a flame retardant agent, (b) a polyol component, and (c) a polyisocyanate component, wherein the flame retardant agent is represented by the following formula (III):

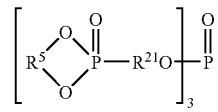
(III)

wherein, in formula (III), $R^5$ is a $C_{2-9}$ alkylene group, and $R^{21}$ is a linking group having formula 89:

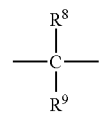
(Formula 89)

(in formula 89, $R^8$ and $R^9$ may be identical to or different from each other; are either hydrogen, a $C_{1-6}$ alkyl group, or $C_{6-11}$ aryl group; or $R^8$ and $R^9$ may be combined to become a $C_{4-10}$ alkylene group which may have one or more substituents, the $C_{4-10}$ alkylene group forming the following cyclic structure together with the carbon atom

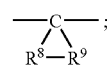

and a total number of carbons of $R^8$ and $R^9$ is 0 to 12).

(38) A composition according to item (37), further comprising (d) a catalyst, (e) a silicone foam stabilizer, and (f) a foaming agent.

(39) A composition according to item (37), wherein $R^{21}$ of the flame retardant agent is either a methylene group, a —CH(CH$_3$)— group, or a —C(CH$_3$)$_2$— group.

(40) A composition according to item (37), wherein $R^5$ of the flame retardant agent is the following formula (IV)

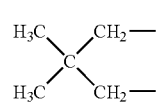
(IV)

(41) A composition according to item (37), wherein the polyol component is selected from the group consisting of polyether polyol, polyester polyol, and polymer polyol.

(42) A composition according to item (37), wherein the polyisocyanate component is selected from the group consisting of tolylene diisocyanate (TDI) and diphenylmethane 4,4'-diisocyanate (MDI).

(43) A composition according to item (37), wherein a content of the flame retardant agent is 0.1 to 60 parts by weight with respect to 100 parts by weight of the polyol component.

(44) A composition according to item (37), further comprising, as an antioxidant, (g) a hydroquinone compound represented by the following general formula (VII) and/or trivalent organic phosphorus compound:

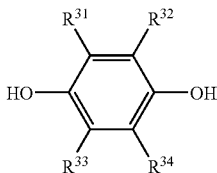

(VII)

(in the formula, $R^{31}$, $R^{32}$, $R^{33}$ and $R^{34}$ are each a hydrogen atom or a $C_{1-14}$ alkyl group).

(45) A molded product which is obtained by molding the composition according to item (27).
(46) A molded product which is obtained by molding the composition according to item (37).
(47) A method for molding a flame retardant polyurethane foam, comprising the step of foaming a composition according to item (27).
(48) A method for molding a flame retardant polyurethane foam, comprising the step of foaming a composition according to item (37).

Thus, the invention described herein makes possible the advantages of providing (i) a novel compound solving the above-described problems, specifically, a phosphate-phosphonate compound which is stable against water and heat, has a low volatility, has little influence on various physical properties of a product for which the phosphate-phosphonate compound is used as a material, is recyclable and imposes little load on environment, and does not contain a halogen atom such as chlorine or bromine; (ii) a flame retardant polyester fiber solving the above-described problems, specifically, a flame retardant polyester fiber which uses a specific organic phosphorus compound having a phosphate-phosphonate bond in one molecule, and thus is stable against water and heat and is durable against washing; and (iii) a flame retardant polyurethane resin composition solving the above-described problems, specifically, a flame retardant polyurethane resin composition which uses a specific organic phosphorus compound having a phosphate-phosphonate bond in one molecule, and thus is superb in flame retarding property and is not substantially influenced regarding various properties thereof by the phosphorus compound.

These and other advantages of the present invention will become apparent to those skilled in the art upon reading and understanding the following detailed description with reference to the accompanying figures.

BRIEF DESCRIPTION OF THE DRAWINGS

FIG. 4C shows a partially enlarged view of the $^1$H-NMR chart of phosphorus compound (2).
FIG. 5C shows a partially enlarged view of the $^{13}$C-NMR chart of phosphorus compound (2).
FIG. 7B shows a partially enlarged view of the $^1$H-NMR chart of phosphorus compound (3).
FIG. 9B shows a partially enlarged view of the GC-MS chart of phosphorus compound (3).
FIG. 13A shows $^1$H-NMR measurement data of phosphorus compound (5).

FIG. 14A shows $^{13}$C-NMR measurement data of phosphorus compound (5).

DESCRIPTION OF THE PREFERRED EMBODIMENTS

Figure 1A:
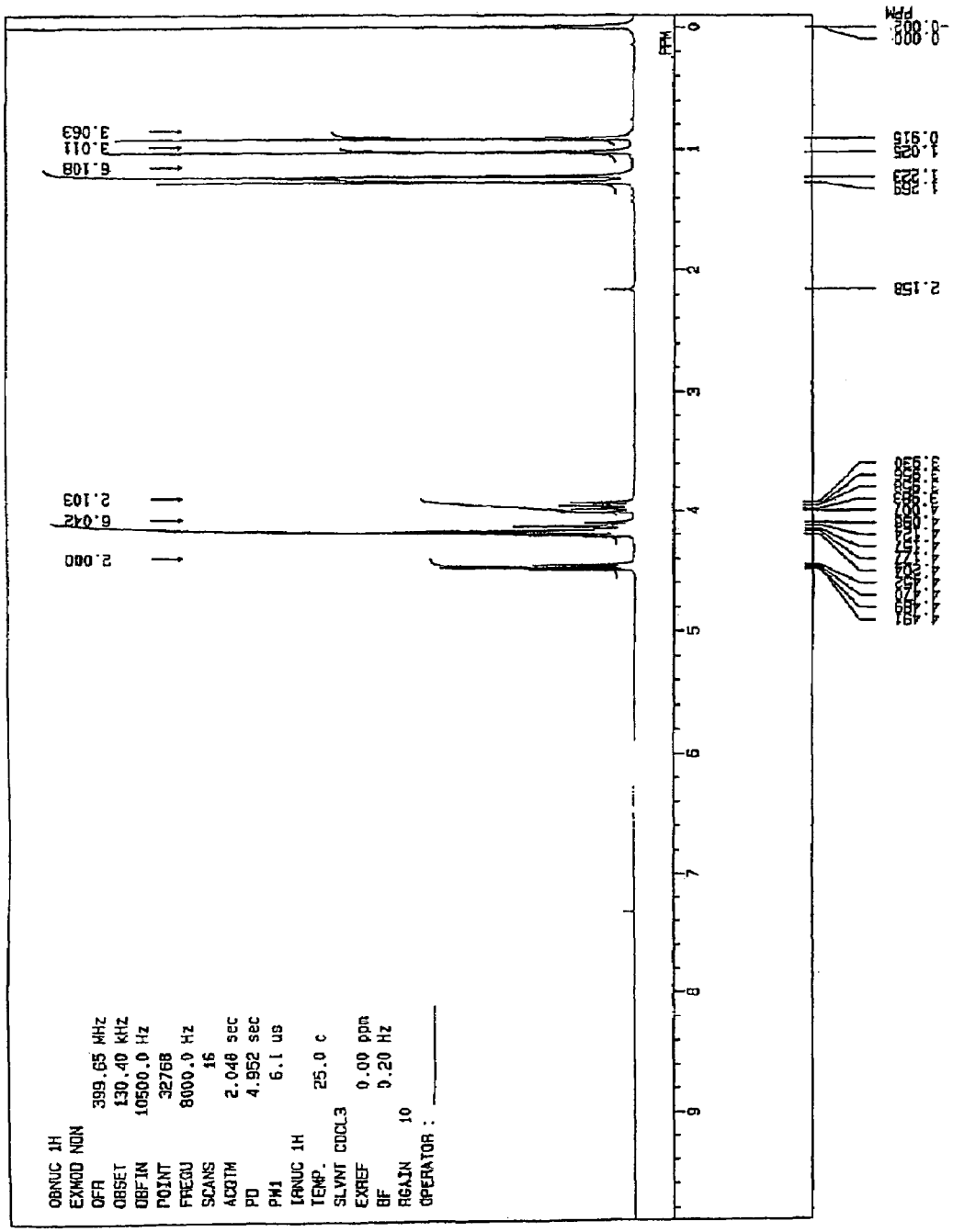
FIG. 1A shows a $^1$H-NMR chart of phosphorus compound (1).

Hereinafter, the present invention will be described by way of illustrative examples with reference to the accompanying drawings.

The present inventor synthesized a series of novel phosphorus compounds and characterized them by analysis. Thus, the present invention relates to a compound represented by the above general formula (I) and a compound represented by the above general formula (III). Hereinafter, the present invention will be described in detail.

(Compound (I) According to the Present Invention)

Compounds according to the present invention and compounds used as a flame retardant agent according to the present invention are generally represented by the above general formula (I).

($R^1$ Through $R^4$)

In formula (I), $R^1$ to $R^4$ are identical to or different from each other, and may each be either a $C_{2-8}$ alkyl group having a straight or branched chain, a $C_{5-10}$ cycloalkyl group which may have one or more substituents, or a $C_{6-15}$ aryl group which may have one or more substituents. Alternatively, when $R^1$ and $R^2$ are combined to form a cyclic structure, $R^1$ and $R^2$ may form a $C_{2-9}$ alkylene group. When $R^3$ and $R^4$ are combined to form a cyclic structure, $R^3$ and $R^4$ may form a $C_{2-9}$ alkylene group. At least one of a combination of $R^1$ and $R^2$ and a combination of $R^3$ and $R^4$ forms a cyclic structure together with the oxygen atoms and the phosphorus atom.

When either one of $R^1$ through $R^4$ is an alkyl group having a straight or branched chain, the alkyl group preferably has a carbon number of 2 through 5, more preferably has a carbon number of 3 through 5, and still more preferably has a carbon number of 4 through 5. When the carbon number is too small, it may be difficult to synthesize a compound according to the present invention, and the thermal resistance, water resistance, or the like of the compound may be lowered. When the carbon number is too large, the flame retarding property of a material containing the compound (for example, a polyurethane resin composition containing the phosphorus compound or a polyester fiber processed with the phosphorus compound) may be lowered.

When either one of $R^1$ through $R^4$ is a $C_{5-10}$ cycloalkyl group which may have one or more substituents, the substituent which the cycloalkyl group may have is, for example, a $C_{1-7}$ alkyl having a straight or branched chain (for example, methyl, ethyl, n-propyl, n-butyl, iso-butyl, sec-butyl, or tert-butyl). When the carbon number of $R^1$ through $R^4$ is too small, the thermal resistance, water resistance, or the like of the compound may be lowered. When the carbon number $R^1$ through $R^4$ is too large, the flame retarding property of a material containing the compound (for example a polyurethane resin composition containing the phosphorus compound or a polyester fiber processed with the phosphorus compound) may be lowered.

The number of members of the ring in the cycloalkyl group may be 3 through 10. A cycloalkyl group having a 5-through 7-membered ring is preferable, and a cycloalkyl group having a 6-membered ring is more preferable in terms of availability of raw material.

When either one of $R^1$ through $R^4$ is a $C_{6-15}$ aryl group, exemplary aryl groups include phenyl, 1-naphtyl, and 2-naphtyl. Phenyl is preferable since it does not lower the phosphorus content in the compound.

When either one of $R^1$ through $R^4$ is a $C_{6-15}$ aryl group which may have one or more substituents, the substituent which the aryl group may have is, for example, $C_{1-9}$ alkyl having a straight or branched chain. Examples of substituted aryl which may have such a substituent include 2-methylphenyl, 3-methylphenyl, 4-methylphenyl, 2,6-dimethylphenyl, 2,4-dimethylphenyl, 3,5-dimethylphenyl, and 2,6-di-tert-butyl-4-methylphenyl. When the carbon number of $R^1$ through $R^4$ is too small, the thermal resistance, water resistance, or the like of the compound may be lowered. When the carbon number $R^1$ through $R^4$ is too large, the flame retarding property of a material containing the compound (for example, a polyurethane resin composition containing the phosphorus compound or a polyester fiber processed with the phosphorus compound) may be lowered.

When $R^1$ and $R^2$ are combined to become a $C_{2-9}$ alkylene group and form cyclic structure A together with the oxygen atoms and the phosphorus atom, the linking group formed of $R^1$ and $R^2$ bonded to each other, —$R^1$-$R^2$— is preferably a $C_{2-6}$ alkylene group. The number of members of the ring of cyclic structure A is preferably 5 through 7, more preferably 5 or 6, and still more preferably 6. When the ring is too large or too small, the ring is likely to be unstable and as a result, an acid component (P—OH) generated by cleaving of the ring may undesirably exert an adverse effect on a material containing the compound (for example, a polyurethane resin composition containing the phosphorus compound or a polyester fiber processed with the phosphorus compound).

Cyclic structure A is especially preferably cyclic structure A1 represented by the following formula.

Cyclic structure A1:

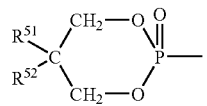

Here, $R^{51}$ and $R^{52}$ may be identical to or different from each other, and are either hydrogen or alkyl. A total carbon number of $R^{51}$ and $R^{52}$ is 0 through 6, and more preferably 0 through 4.

When $R^3$ and $R^4$ are combined to become a $C_{2-9}$ alkylene group and form cyclic structure B together with the oxygen atoms and the phosphorus atom, the linking group formed of $R^3$ and $R^4$ bonded to each other, —$R^3$-$R^4$— is preferably a $C_{2-6}$ alkylene group. The number of members of the ring of cyclic structure B is preferably 5 through 7, more preferably 5 or 6, and still more preferably 6. When the ring is too large or too small, the ring is likely to be unstable and as a result, an acid component (P—OH) generated by cleaving of the ring may undesirably exert an adverse effect on a material containing the compound (for example, a polyurethane resin composition containing the phosphorus compound or a polyester fiber processed with the phosphorus compound).

Cyclic structure B is especially preferably cyclic structure B1 represented by the following formula.

Cyclic structure B1:

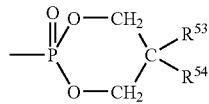

Here, $R^{53}$ and $R^{54}$ may be identical to or different from each other, and are either hydrogen or alkyl. A total carbon number of $R^{53}$ and $R^{54}$ is 0 through 6, and more preferably 0 through 4.

(Total Carbon Number of $R^1$ Through $R^4$)

The above-mentioned groups $R^1$ through $R^4$ may independently be any of various types of groups listed above. When the compound has both cyclic structures A and B, $R^1$ through $R^4$ are preferably selected such that the total carbon number of $R^1$ through $R^4$ is 6 or greater, and more preferably 10 or greater. When the compound has either cyclic structure A or B, $R^1$ through $R^4$ are preferably selected such that the total carbon number of $R^1$ through $R^4$ is 9 or greater, and more preferably 13 or greater. When the total carbon number of $R^1$ through $R^4$ is too small, the thermal resistance, water resistance, hydrolysis resistance or the like of the compound is likely to be lowered, which may undesirably exert an adverse effect on various physical properties of a material containing the phosphorus compound (for example, a polyurethane resin composition containing the phosphorus compound or a polyester fiber processed with the phosphorus compound). $R^1$ through $R^4$ are preferably selected such that the total carbon number is 25 or less, more preferably 21 or less, and still more preferably 17 or less. When the total carbon number of $R^1$ through $R^4$ is too large, the flame retarding property of a material containing the compound (for example, a polyurethane resin composition containing a phosphorus compound or a polyester fiber processed with a phosphorus compound) may be lowered.

(Preferable Combination of $R^1$ and $R^2$, and of $R^3$ and $R^4$)

In consideration of availability of raw material and ease of synthesis (synthesis methods will be described later), when $R^1$ and $R^2$ do not form cyclic structure A, $R^1$ and $R^2$ are preferably identical to each other. When $R^3$ and $R^4$ do not form cyclic structure B, $R^3$ and $R^4$ are preferably identical to each other. It is also preferable that $R^1$ and $R^2$ form a cyclic structure together with the oxygen atoms and the phosphorus atom, and further $R^3$ and $R^4$ form a cyclic structure together with the oxygen atoms and the phosphorus atom.

When all of $R^1$ through $R^4$ are each an alkyl group of $C_2$ or less, or when one or more of $R^1$ through $R^4$ is a methyl group, the bonding force of the portion is weakened. Therefore, decomposability of the compound against water is increased and hydrolysis is more likely to occur. Thus, the water resistance and thermal resistance of the compound are likely to be lowered. In the case where an acid component is generated by hydrolysis, the acid component may undesirably exert an adverse effect on the resin to which the compound is added as a flame retardant agent. When the compound has cyclic structure A or B, hydrolysis is relatively unlikely to occur even when the group which does not have a cyclic structure is an ethyl group, although the reason has not been found yet.

(Linked Group $R^{20}$)

$R^{20}$ is a linking group having formula 67.

(Formula 67)

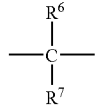

Here, $R^6$ and $R^7$ may be identical to or different from each other; are either hydrogen, a $C_{1-6}$ alkyl group, or $C_{6-11}$ aryl group; or $R^6$ and $R^7$ may be combined to become a $C_{4-10}$ alkylene group which may have one or more substituents, the $C_{4-10}$ alkylene group forming the following cyclic structure together with the carbon atom.

A sum of the carbon numbers of $R^6$ and $R^7$ is 0 through 12. When $R^6$ or $R^7$ is a $C_{6-11}$ aryl group, the $C_{6-11}$ aryl group is preferably phenyl which may be substituted with $C_{1-5}$ alkyl, and more preferably phenyl. Namely, $R^{20}$ is either a methylene group, a $C_{2-13}$ alkylene group having a branched chain, a $C_{5-11}$ alkylene group having a cyclic structure, or a $C_{7-12}$ aryl substituted alkylene group. Among them, a methylene group and a $C_{2-13}$ alkylene group having a branched chain are preferable; a methylene group and a $C_{2-7}$ alkylene group having a branched chain are more preferable; and a methylene group, a —CH(CH$_3$)— group, and a —C(CH$_3$)$_2$— group are still more preferable.

$R^{20}$ links two phosphorus atoms with one carbon atom and one oxygen atom. Namely, $R^{20}$ is selected such that the backbone has a form of P—C—O—P. Thus, $R^{20}$ is a —CH$_2$— or a substituted form thereof. Examples of $R^{20}$ include —CH$_2$—, —CH(CH$_3$)—, —C(CH$_3$)$_2$—, —CH(C$_2$H$_5$)—, —C(CH$_3$)(C$_2$H$_5$)—, and —C(CH$_3$)(CH$_2$CH(CH$_3$)$_2$)—. An example of $R^{20}$ having a cyclic structure is cyclic —C$_6$H$_{10}$—, i.e., cyclohexylene.

A $C_{7-12}$ aryl substituted alkylene group is a group which is obtained by substituting hydrogen of an alkylene group with aryl and has a total carbon number of 7 through 12. The carbon number of the alkylene moiety of the $C_{7-12}$ aryl substituted alkylene group is preferably 1 through 4, and more preferably 1 (methylene). An aryl moiety of the $C_{7-12}$ aryl substituted alkylene group may be any aryl, and is preferably phenyl. A specific example of a preferable $R^{20}$ is —CH(C$_6$H$_5$).

In terms of availability of raw material, preferable examples of $R^{20}$ include —CH$_2$—, —CH(CH$_3$)—, —C(CH$_3$)$_2$—, —C(CH$_3$)(C$_2$H$_5$)—, —C(CH$_3$)(CH$_2$CH(CH$_3$)$_2$)—, —CH(C$_6$H$_5$)—, and —C$_6$H$_{10}$— (i.e., cyclohexylene). Among them, —CH$_2$—, —CH(CH$_3$)—, —C(CH$_3$)$_2$— and —C(CH$_3$)(CH$_2$CH(CH$_3$)$_2$)— are more preferable; and —CH$_2$—, —CH(CH$_3$)—, and —C(CH$_3$)$_2$— are still more preferable.

(Compound (III) According to the Present Invention)

In another aspect of the invention, compounds represented by the above general formula (III) are provided.

In formula (III), $R^5$ is a $C_{2-9}$ alkylene group, and preferably a $C_{3-9}$ alkylene group. Similar linking groups to those described regarding —$R^1$-$R^2$— in cyclic structure A of the compounds of formula (I) are applicable as $R^5$.

The number of members of the ring in the cyclic structure in formula (III) is preferably 5 through 7, more preferably 5 or 6, and still more preferably 6.

Cyclic structure in formula (III) is especially preferably cyclic structure A2 represented by the following formula.

Cyclic structure A2:

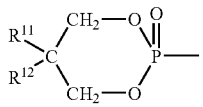

Here, $R^{11}$ and $R^{12}$ may be identical to or different from each other, and are either hydrogen or alkyl. A total carbon number of $R^{11}$ and $R^{12}$ is 0 through 6. A lower limit of the total carbon number is preferably 1, and more preferably 2. As the carbon number becomes greater, the compound tends to be more stable. An upper limit of the total carbon number of $R^{11}$ and $R^{12}$ is preferably 6, and more preferably 4. When the total carbon number is too large, the flame retarding property of a material containing the compound (for example, a polyurethane resin composition containing the phosphorus compound or a polyester fiber processed with the phosphorus compound) may be lowered.

In terms of availability of raw material, preferable examples of $R^5$ include —$(CH_2)_3$—, —$CH_2$—$CH(CH_3)$—$CH_2$—, —$CH_2$—$C(CH_3)_2$—$CH_2$—, and —$CH_2$—$C(C_2H_5)(C_4H_9)$—$CH_2$—, —$CH_2$—$C(CH_3)_2$—$CH_2$— and —$CH_2$—$C(C_2H_5)(C_4H_9)$—$CH_2$— are more preferable.

Generally when the moiety of $R^5$ does not have a cyclic structure, the phosphorus content of a finally obtained phosphorus compound is lowered and accordingly the flame retarding property of the compound is lowered. For example, it is not preferable to add the compound in an amount which is sufficient to provide an intended level of flame retarding property, since this may result in significant reduction in the physical properties of the flame retarded product.

$R^{21}$ is a linking group having formula 89.

(Formula 89)

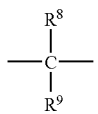

Here, $R^8$ and $R^9$ may be identical to or different from each other; are either hydrogen, a $C_{1-6}$ alkyl group, or $C_{6-11}$ aryl group; or $R^8$ and $R^9$ may be combined to become a $C_{4-10}$ alkylene group which may have one or more substituents, the $C_{4-10}$ alkylene group forming the following cyclic structure together with the carbon atom.

A sum of the carbon numbers of $R^8$ and $R^9$ is 0 through 12. When $R^8$ or $R^9$ is a $C_{6-11}$ aryl group, the $C_{6-11}$ aryl group is preferably phenyl which may be substituted with $C_{1-5}$ alkyl, and more preferably phenyl. Namely, $R^{21}$ is either a methylene group, a $C_{2-13}$ alkylene group having a branched chain, a $C_{5-11}$ alkylene group having a cyclic structure, or a $C_{7-12}$ aryl substituted alkylene group. Among them, a methylene group and a $C_{2-13}$ alkylene group having a branched chain are preferable; a methylene group and a $C_{2-7}$ alkylene group having a branched chain are more preferable; and a methylene group, a —$CH(CH_3)$— group, and a —$C(CH_3)_2$— group are still more preferable.

$R^{21}$ links two phosphorus atoms with one carbon atom and one oxygen atom. Namely, $R^{21}$ is selected such that the backbone has a form of P—C—O—P. Thus, $R^{21}$ is a —$CH_2$— or a substituted form thereof. Examples of $R^{21}$ include —$CH_2$—, —$CH(CH_3)$—, —$C(CH_3)_2$—, —$CH(C_2H_5)$—, —$C(CH_3)(C_2H_5)$—, and —$C(CH_3)(CH_2CH(CH_3)_2)$—. An example of $R^{21}$ having a cyclic structure is cyclic —$C_6H_{10}$—, i.e., cyclohexylene.

A $C_{7-12}$ aryl substituted alkylene group is a group which is obtained by substituting hydrogen of an alkylene group with aryl and has a total carbon number of 7 through 12. The carbon number of the alkylene moiety of the $C_{7-12}$ aryl substituted alkylene group is preferably 1 through 4, and more preferably 1 (methylene). An aryl moiety of the $C_{7-12}$ aryl substituted alkylene group may be any aryl, and is preferably phenyl. A specific example of a preferable $R^{21}$ is —$CH(C_6H_5)$.

In terms of availability of raw material, preferable examples of $R^{21}$ include —$CH_2$—, —$CH(CH_3)$—, —$C(CH_3)_2$—, —$C(CH_3)(C_2H_5)$—, —$C(CH_3)(CH_2CH(CH_3)_2)$—, —$CH(C_6H_5)$—, and —$C_6H_{10}$— (i.e., cyclohexylene). Among them, —$CH_2$—, —$CH(CH_3)$—, —$C(CH_3)_2$— and —$C(CH_3)(CH_2CH(CH_3)_2)$— are more preferable; and —$CH_2$—, —$CH(CH_3)$—, and —$C(CH_3)_2$— are still more preferable.

(Method for Synthesizing a Compound)

A compound represented by formula (I) or (III) can be produced by appropriately combining processes conventionally known as synthesis methods of phosphorus compounds, especially a synthesis method of a phosphate, and a synthesis method of a phosphite.

(1. Synthesis Method of a Phosphite)

A phosphite can be synthesized using, for example, phosphorus trihalide and an alcohol or phenol as materials.

When phosphorus trihalide and an alcohol are used, 1 mol of phosphorus trihalide ($PX_3$) and about 3 mol of alcohol ($R^aOH$) are reacted. A phosphite is obtained in accordance with the following reaction expression.

$3R^aOH+PX_3 \rightarrow O=PH(-OR^a)_2+R^aX+2HX$

When phosphorus trihalide and a phenol ($R^bOH$) are used, 1 mol of phosphorus trihalide and about 3 mol of phenol ($R^bOH$) are reacted and then the reaction product is reacted with 1 mol of water. A phosphite is obtained in accordance with the following reaction expression.

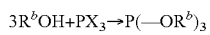

$3R^bOH+PX_3 \rightarrow P(-OR^b)_3$

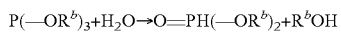

$P(-OR^b)_3+H_2O \rightarrow O=PH(-OR^b)_2+R^bOH$

Alternatively, 1 mol of phosphorus trihalide may be reacted with about 1 mol of diol ($HOR^cOH$) and about 1 mol of water simultaneously.

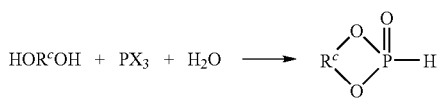

Exemplary phosphorus trihalides usable for the above reactions include phosphorus trichloride and phosphorus tribromide. In terms of availability and cost, phosphorus trichloride is preferable.

Exemplary alcohols usable for the above reactions include ethanol, n-propanol, iso-propanol, n-butanol, iso-butanol, sec-butanol, n-pentanol, n-hexanol, cyclohexanol, n-octanol, and 2-ethylhexanol. n-butanol and sec-butanol are preferable since they are highly hydrolysis resistant, i.e., highly stable, and allow the phosphorus content of a finally obtained phosphorus compound to be relatively high. Ethanol, n-propanol, and iso-propanol are also preferable since they allow the phosphorus content of a finally obtained phosphorus compound to be high and are relatively highly hydrolysis resistant. 2-ethylhexanol is also preferable since it is stable and low in volatility although the phosphorus content of a finally obtained phosphorus compound is relatively low when 2-ethylhexanol is used.

Exemplary phenols usable for the above reactions include phenol, cresol, xylenol, and naphtol. Phenol is preferable since it allows the phosphorus content of a finally obtained phosphorus compound to be high.

Exemplary diols usable for the above reactions include ethylene glycol, 1,2-propanediol, 1,3-propanediol, 1,2-butanediol, 1,3-butanediol, 2,2-diethyl-1,3-propanediol, 2,2-dimethyl-1,3-propanediol (neopentylglycol), 2-butyl-2-ethyl-1,3-propanediol, 1,2-hexanediol, and 1,3-hexanediol. 1,3-propanediol, 1,3-butanediol, neopentylglycol, 2-butyl-2-ethyl-1,3-propanediol, and 1,3-hexanediol are preferable since they provide a chemically stable 6-membered ring. Neopentylglycol is more preferable.

In the above reactions, a solvent which is not related to the reaction may optionally be used. For example, when neopentylglycol, which is a diol, is used as a starting material, a solvent can be effectively used as follows. Neopentylglycol, which is solid at room temperature, is dissolved or dispersed by a solvent, and thus the reaction proceeds smoothly. Usable solvents which are not related to the reaction include, for example, benzene, toluene, xylene, chlorobenzene, 1,4-dioxane, tetrahydrofuran, and 1,2-dichloroethane.

The above reactions are generally performed as follows. An alcohol, diol or phenol, and optionally water and/or solvent are first prepared. Then, phosphorus trihalide is added thereto, and the generated hydrogen halide is discharged to the outside of the system.

(2. Synthesis Method of a Phosphonate)

A phosphonate containing an alcoholic hydroxyl group is obtained by reacting the phosphite obtained by the above reaction with an aldehyde or a ketone in the presence of, for example, a basic catalyst.

Exemplary basic catalysts usable for the above reactions include, for example, amines including triethylamine, tributylamine, pyridine, lutidine, picoline, and 1,8-diazabicyclo (5,4,0) undecene-7 (DBU); and alkaline metals and metal-containing bases including metal sodium, metal potassium, sodium hydride, and sodium alcoxide. Triethylamine is preferable since it can be easily removed after the reaction.

Exemplary aldehydes usable for the above reactions include paraformaldehyde, formaldehyde, acetaldehyde, and benzaldehyde. Paraformaldehyde and formaldehyde are preferable since they are low cost and allow the phosphorus content of a finally obtained phosphorus compound to be high. Some of the phosphonates obtained using formaldehyde have a structure which is liable to hydrolysis with water. Therefore, when an aqueous solution of formaldehyde (formalin) is used, care should be taken such that hydrolysis does not occur to the resultant phosphonate.

Exemplary ketones usable for the above reactions include acetone, methyl ethyl ketone (MEK), methyl isobutyl ketone (MIBK), cyclopentanone, cyclohexanone, and methylcyclohexanone. Acetone is preferable since it allows the phosphorus content of a finally obtained phosphorus compound to be high.

In the above reactions, a solvent which is not related to the reaction may optionally be used. Usable solvents which are not related to the reaction include, for example, benzene, toluene, xylene, chlorobenzene, and 1,2-dichloroethane.

(3. Synthesis Method of a Phosphate-phosphonate Compound)

A compound represented by formula (I) is obtained, for example, by reacting the phosphonate obtained by the above reaction with a di-substituted phosphorohalidate in the presence of a hydrogen halide capturing agent and optionally a catalyst.

A compound represented by formula (III) is obtained, for example, by reacting the phosphonate obtained by the above reaction with phosphorus oxyhalide in the presence of a hydrogen halide capturing agent and optionally a catalyst.

Exemplary hydrogen halide capturing agents usable for the above reactions include triethylamine, tributylamine, and pyridine. Exemplary catalysts usable for the above reaction include Lewis acid-based catalysts including magnesium chloride and aluminum chloride; and amine-based catalysts including 4-(dimethylamino) pyridine.

Exemplary di-substituted phosphorohalidates usable for the above reactions include diaryl phosphorohalidates including diphenyl phosphorohalidate and dicresyl phosphorohalidate; dialkyl phosphorohalidates including dipropyl phosphorohalidate and dibutyl phosphorohalidate; and cyclic phosphorohalidates including neopentylene phosphorohalidate. Methods for producing these di-substituted phosphorohalidates are described in Japanese Laid-Open Publication No. 2000-239286, and these phosphorohalidates can be synthesized by such methods.

Exemplary phosphorus oxyhalides which are usable for the above reaction include phosphorus oxychloride and phosphorus oxybromide. Phosphorus oxychloride is preferable since it is low cost.

As an additional specific example, an exemplary method for producing a phosphate-phosphonate compound which is represented by formula (VI) will be described.

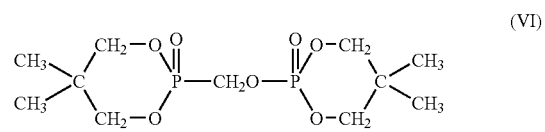

(VI)

The reaction is mainly in accordance with the following formula.

Step (1):

CH₃-C(CH₃)(CH₂-OH)(CH₂-OH) + PCl₃ + H₂O → cyclic-[CH₃-C(CH₃)(CH₂-O)(CH₂-O)]P(=O)-H + 3HCl

Step (2):

cyclic-[CH₃-C(CH₃)(CH₂-O)(CH₂-O)]P(=O)-H + HCHO → cyclic-[CH₃-C(CH₃)(CH₂-O)(CH₂-O)]P(=O)-CH₂OH

Step (3):

cyclic-[CH₃-C(CH₃)(CH₂-O)(CH₂-O)]P(=O)-CH₂OH +

Cl-P(=O)[O-CH₂-C(CH₃)(CH₃)-CH₂-O] → cyclic-[CH₃-C(CH₃)(CH₂-O)(CH₂-O)]P(=O)-CH₂O-P(=O)[O-CH₂-C(CH₃)(CH₃)-CH₂-O] + HCl The compounds represented by formula (I) specifically include the following compounds other than those represented by the general formula (VI). The following compounds can be produced by a similar method to that of the above-described method.

The compounds according to the present invention are not limited to the following compounds.

Compound 12:

Compound 13:

Compound 14:

Compound 15:

Compound 16:

Compound 17:

Compound 18:

Compound 19:

Compound 20:

Compound 21:

Compound 22:

Compound 23:

Compound 24:

-continued
Compound 25:
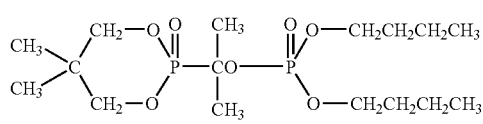
Compound 26:
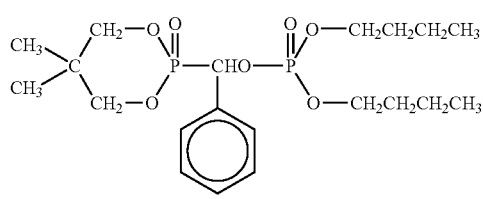
Compound 27:
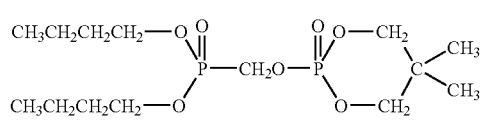
Compound 28:
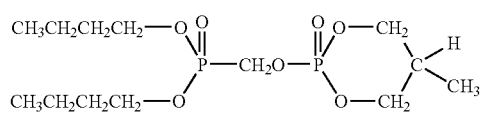
Compound 29:
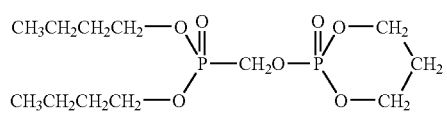
Compound 30:
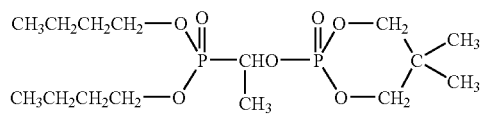
Compound 31:
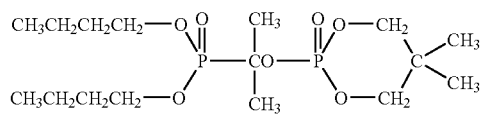
Compound 32:
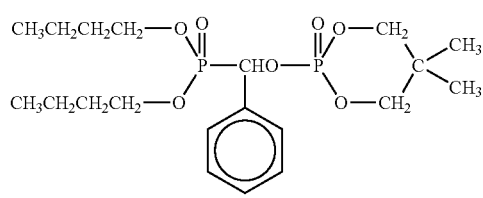
Compound 33:
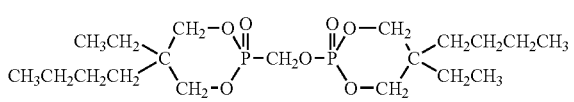
Compound 34:
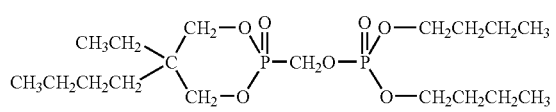
-continued
Compound 35:
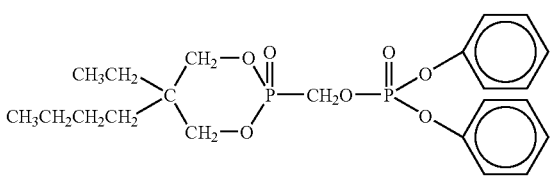
Compound 36:
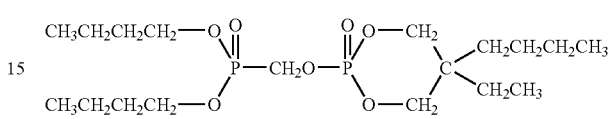
Compound 37:
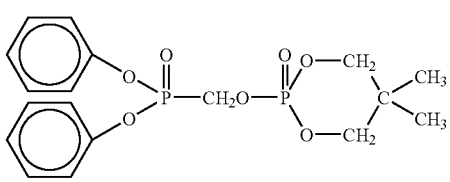
Specific examples of the compounds usable as a flame retardant agent according to the present invention further include the following compounds.
Compound 38:
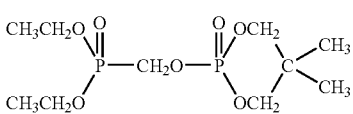
Compound 39:
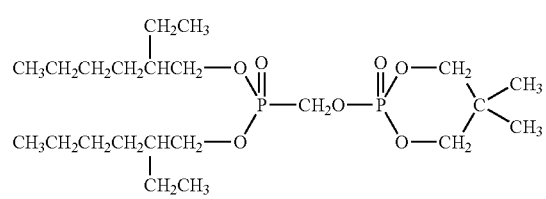
Compound 40:
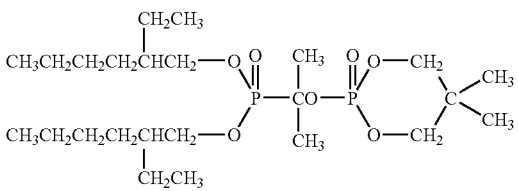
Compound 41:
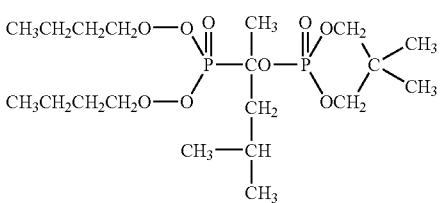

Compound 42:

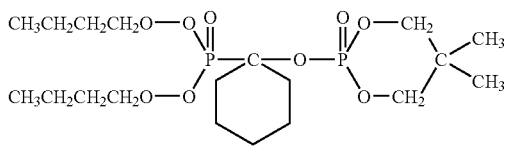

The compounds represented by formula (III) specifically include the following compounds. The following compounds can be produced by a similar method to that of the above-described method.

The compounds according to the present invention are not limited to the following compounds.

Compound 43:

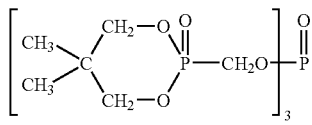

Compound 44:

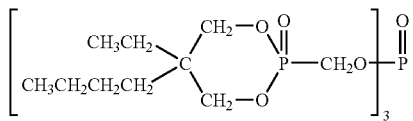

Compound 45:

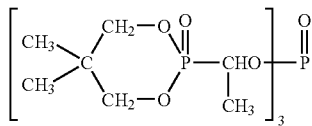

Compound 46:

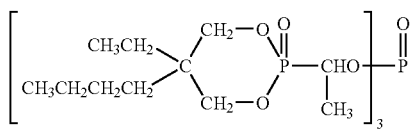

Phosphate-phosphonate compounds according to the present invention are useful as various types of flame retardant agents, for example, as various types of flame retardant agents for resins. Resins may be synthetic resins or natural resins. Phosphate-phosphonate compounds according to the present invention are especially useful for synthetic resins. Resins may be thermoplastic resins or thermosetting resins. More specifically, phosphate-phosphonate compounds according to the present invention are very useful as flame retardant agents for thermoplastic resins including polycarbonate, ABS resins, and PPE; thermosetting resins including polyurethane resins, epoxy resins and phenol resins; and resins and fibers of polyester including polyethylene terephthalate and polybutylene terephthalate.

(Flame Retardant Agent for Polyester)

As flame retardant agents for a polyester according to the present invention, the compounds represented by formula (I) are usable. The details thereof (for example, the specific examples and production methods thereof) are as provided in this specification regarding the corresponding compounds.

Also, as flame retardant agents for a polyester according to the present invention, the compounds represented by formula (III) are usable. The details thereof (for example, the specific examples and production methods thereof) are as provided in this specification regarding the corresponding compounds.

These flame retardant agents for a polyester are especially effective for a polyester fiber. For example, polyester fiber can be provided with a superb flame retarding property by fixing the flame retardant agent to the surface of the polyester fiber.

When a flame retardant agent for a polyester according to the present invention is used, the amount of a phosphorus compound to be fixed to the polyester fiber is preferably 0.1% by weight or greater with respect to the total weight of the phosphorus compound and the polyester fiber, more preferably 0.3% by weight or greater, and especially preferably 0.5% by weight or greater. The amount of a phosphorus compound is preferably 30% by weight or less with respect to the total weight of the phosphorus compound and the polyester fiber, more preferably 10% by weight or less, and especially preferably 5% by weight or less. When the phosphorus compound content is too small, it is difficult to provide the polyester fiber with a sufficient level of flame retarding property. When the phosphorus compound content is too large, it is difficult to provide the effect of enhancing the level of the flame retarding property in accordance with the increase in the amount of the phosphorus compound, and bleeding-out is likely to occur to the surface of the fiber. When bleeding-out occurs, the flame retardant agent component generated on the surface of the fiber easily causes undesirable combustion of the fiber.

(Polyester Fiber)

For the present invention, conventionally known types of polyester fibers are usable with no specific limitation. Specific examples of usable polyester materials include polyethylene terephthalate, polytrimethylene terephthalate, polybutylene terephthalate, polyethylene naphthalate, polytrimethylene naphthalate, polybutylene naphthalate, isophthalic acid modified polyethylene terephthalate, and isophthalic acid modified polybutylene terephthalate. Polyethylene terephthalate is preferable. The cross-sectional shape of the polyester fiber may be any shape; for example, may be circular or may have an abnormal shape. A circular cross-section is preferable.

There is no specific limitation on the diameter of the filament of the polyester fiber. A flame retardant agent according to the present invention may be applicable to a polyester fiber having any diameter of filament. A flame retardant agent of the present invention is preferably usable to a polyester fiber of, for example, 0.001 to 3000 D (denier; grams per 9000 m), and more preferably usable to a polyester fiber of 0.01 to 200 D.

The polyester fiber is usable in any form. Examples of usable forms include woven fabrics, knitted fabrics, nonwoven fabrics, strings, ropes, threads, tow, top, hank, and knitted woven fabrics.

A flame retardant agent according to the present invention may be usable for a mixture of a polyester fiber and other types of fiber. For example, a flame retardant agent according to the present invention may be applied to a mixture of any of the above-described polyester fibers and other types of fiber (e.g., blended yarn woven fabrics or union cloth with natural fibers, regenerated fibers, semi-synthetic fibers synthetic fibers) or to union fabric.

There is no specific limitation on the uses of the fiber. A flame retardant agent according to the present invention may be applicable to, for example, various types of fabric products including clothing, industrial products, and fishing nets.

(Method for Producing a Flame Retardation Processing Agent for a Polyester Fiber)

A flame retardant agent for a polyester fiber according to the present invention is fixed to the polyester fiber by various known techniques. For example, a flame retardant agent for a polyester fiber according to the present invention can be fixed to the polyester fiber as follows. A solvent or the like is optionally added to a flame retardant agent according to the present invention to make the flame retardant agent a liquid material, and this liquid material is put into contact with the polyester fiber. Then, the solvent or the like is optionally removed by a drying step or the like. Thus, the flame retardant agent for a polyester fiber can be fixed to the polyester fiber.

In the present invention, a preferable flame retardation processing agent which is produced in order to provide the polyester fiber with a flame retarding property is usually obtained by dissolving, emulsifying or dispersing a phosphorus compound in water, or by dissolving or dispersing a phosphorus compound in an organic solvent. A phosphorus compound can be dispersed in water by various conventionally known techniques, for example, by mixing and stirring the phosphorus compound, a surfactant such as an anionic surfactant, a nonionic surfactant or the like, and an organic solvent, and gradually adding hot water to emulsify or disperse the phosphorus compound. As the surfactant, any conventionally known surfactant is usable with no specific limitation.

Specifically, exemplary anionic surfactants include carboxylates including fatty acid soap; sulfates including higher alcohol sulfate, higher alkyl polyalkylene glycol ether sulfate, sulfated oil, sulfated fatty acid ester, sulfated fatty acid, and sulfated olefin; sulfonates including alkylbenzenesulfonate, alkylnaphthalenesulfonate, formalin condensates of naphthalenesulfonate or the like, α-olefinsulfonate, paraffinsulfonate, Igepon T-type (a compound obtained by reaction of oleic acid chloride and N-methyltaurine), and sulfosuccinic acid diester salt; and phosphates including higher alcohol phosphate.

Specifically, exemplary nonionic surfactants include polyalkyleneglycol type surfactants including higher alcohol alkylene oxide adducts, alkylphenol alkylene oxide adducts, styrenated alkylphenol alkylene oxide adducts, styrenated phenol alkylene oxide adducts, fatty acid alkylene oxide adducts, polyvalent alcohol fatty acid ester alkylene oxide adducts, higher alkylamine alkylene oxide adducts, fatty acid amide alkylene oxide adducts, alkylene oxide adducts of fats and oils, and polypropyleneglycol ethylene oxide adducts; and polyvalent alcohol type surfactants including fatty acid esters of glycerol, fatty acid esters of pentaerythritol, fatty acid esters of sorbitol and sorbitan, fatty acid esters of saccharose, alkylethers of polyvalent alcohol, and fatty acid amides of alkanolamines.

For dispersions, dispersion stabilizers such as polyvinyl alcohols, methyl cellulose, hydroxymethyl cellulose, xanthan gum, starch glue, and the like are usable.

As for the amount of the dispersant stabilizer, 0.05 parts by weight or greater with respect to 100 parts by weight of the flame retardation processing agent is preferable, 0.1 parts by weight or greater is more preferable. 5 parts by weight or less with respect to 100 parts by weight of the flame retardation processing agent is preferable, and 3 parts by weight or less is more preferable. When the amount of the dispersant stabilizer is too small, aggregation or sedimentation of the phosphorus compound may undesirably occur. When the amount of the dispersant stabilizer is too large, the viscosity of the dispersion is increased and as a result, it is difficult for the flame retardation processing agent to penetrate deep into the fiber. This may lower the level of the flame retarding property of the post-processing polyester fiber.

Specifically, exemplary organic solvents include aromatic hydrocarbons including toluene, xylene, and alkylnaphthalene; alcohols including methanol, ethanol, isopropanol, and ethylene glycol; ketones including acetone, and methyl ethyl ketone; ethers including dioxane, and ethylcellosolve; amides including dimethylformamide; sulfoxides including dimethylsulfoxide; and halogen-based hydrocarbons including methylene chloride, and chloroform. These can be used independently, or a combination of two or more of these can be used.

A flame retardation processing agent in the form of an emulsified or dispersed aqueous liquid can be obtained by an emulsification device or a dispersion device conventionally used for producing an emulsified or dispersed flame retardation processing agent, for example, a homogenizer, a colloid mill, a ball mill, a sand grinder, or the like.

When ruggedness against light or the like is required in addition to the flame retarding property, ultraviolet absorption agents including benzotriazole-based and benzophenone-based agents, and other conventionally used processing agents for a fiber may be used together with the flame retardation processing agent to such a degree that the flame retarding property is not spoiled. Exemplary processing agents for a fiber include antistatic agent, water and oil repellents, soil resistant agents, hard finishing agents, texture (feel) adjusting agents, softeners, antibacterial agents, water absorbing agents, and slip preventing agents. These agents may be attached or adsorbed to the polyester fiber in advance. These agents may be adsorbed to the fiber when the fiber is processed to be flame retardant.

(Method for Flame-retardation Processing of a Polyester Fiber)

According to the present invention, a flame retarding agent can be applied to a polyester fiber by an arbitrary method. Preferably, the flame retarding agent is applied after the polyester fiber is formed. Specifically, for example, a flame retardation processing agent is provided to the fiber (flame retardation processing agent providing step), and the fiber is heated to be flame retardant (heat treatment step). More specifically, it is especially preferable to use one of the following three methods (method 1, method 2, and method 3).

(Method 1)

According to method 1, a flame retardation processing agent is provided to polyester fiber in the flame retardation processing agent providing step, and then the polyester fiber provided with the flame retardation processing agent is heat-treated at 100 to 220° C. in the heat treatment step. To method 1, a dry heating system or a wet heating system such as a spray-dry-cure system, a pad-dry-steam system, a pad-steam system, a pad-dry-cure system or the like is usable.

Specifically, the polyester fiber is first sprayed or padded with a processing liquid containing a flame retardation processing agent or a diluted liquid thereof. The fiber is dried, and then is heat-treated at atmospheric pressure at a temperature of preferably 100 to 220° C., and more preferably 160 to 190° C. for, for example, several tens of seconds to several minutes.

When the temperature is too low, it is likely that the non-crystalline area in molecules of the polyester fiber cannot be easily loosened or expanded sufficiently to receive the molecules or particles of the phosphorus compound existing in the flame retardation processing agent. As a result, the flame retarding property of the post-processing polyester fiber may be undesirably lowered. When the temperature is too high, the flame retardation processing agent can be fixed to the polyester fiber more strongly. However, with method 1, when the heat treating temperature is too high, the strength of the polyester fiber may be lowered or the polyester fiber may be thermally denatured, although the degree of such undesirable changes rely on the heat-treating time.

By heat-treating the polyester fiber at the above-mentioned preferable temperature range, the phosphorus compound existing in the flame retardation processing agent is fixed to the non-crystalline area in the molecules of the polyester fiber stably and in a larger amount even at atmospheric pressure. Accordingly, the polyester fiber can be provided with a sufficient level of flame retarding property and washing durability.

(Method 2)

According to method 2, while polyester fiber is immersed in a processing liquid containing a flame retardation processing agent or a diluted liquid thereof so as to provide the polyester fiber with the flame retardation processing agent in the flame retardation processing agent providing step, the processing liquid is heat-treated at a high temperature and atmospheric pressure or a high temperature and a high pressure (for example, 90 to 150° C.; atmospheric pressure to 0.4 MPa) in the heat treatment step. Namely, the flame retardation processing agent providing step and the heat treatment step are performed concurrently.

Specifically, in the state where the polyester fiber is immersed in a flame retardation processing agent using a package dyeing device such as a liquid flow dyeing device, a beam dyeing device, a cheese dyeing device or the like, the flame retardation processing agent is heat-treated, preferably at a high temperature and atmospheric pressure or a high temperature and a high pressure (90 to 150° C.; atmospheric pressure to 0.4 MPa) and more preferably at a high temperature and a high pressure (110 to 140° C.; 0.05 to 0.3 MPa), for several minutes to several tens of minutes. Thus, the flame retardation processing agent can be fixed to the polyester fiber.

When the temperature is too low, it is likely that the non-crystalline area in molecules of the polyester fiber cannot be easily loosened or expanded sufficiently to receive the molecules or particles of the phosphorus compound existing in the flame retardation processing agent. As a result, the flame retarding property of the post-processing polyester fiber may be undesirably lowered. When the heat treating temperature is too high, the strength of the polyester fiber may be lowered or the polyester fiber may be thermally denatured, although the degree of such undesirable changes rely on the heating time.

By performing heat-treating step under the above-mentioned preferable conditions, the phosphorus compound existing in the flame retardation processing agent is fixed to the non-crystalline area in the molecules of the polyester fiber stably and in a larger amount, like with method 1. Accordingly, the polyester fiber can be provided with a sufficient level of flame retarding property and washing durability. Before the polyester fiber is immersed, the flame retardation processing agent may be heated in advance to a temperature in the above-mentioned preferable range. The polyester fiber may be immersed in such a heated solution. In this case also, the excellent effect of fixing the flame retardation processing agent can be provided.

(Method 3)

According to method 3, a polyester fiber is immersed in a processing liquid containing a flame retardation processing agent and a carrier or a diluted liquid thereof so as to provide the polyester fiber with the flame retardation processing agent in the flame retardation processing agent providing step; and the flame retardation processing liquid is heated and thus the polyester fiber is heat-treated at a high temperature and an atmospheric pressure or at a high temperature and a high pressure (for example, 80 to 130° C.; atmospheric pressure to 0.2 MPa) in the heat treatment step. The carrier is a substance for swelling the polyester fiber so as to promote the flame retardation processing agent to be fixed into the array of molecules of the polyester fiber in a superb state.

As the carrier, carriers used in conventional carrier dyeing are usable. Specifically, exemplary carriers include chlorobenzene-based, aromatic ester-based, methylnaphthalene-based, diphenyl-based, benzoic acid-based, and orthophenylphenol-based compounds. These compounds may be used independently, or a combination of two or more of these can be used.

According to this method, the carrier which is emulsified or dispersed in the flame retardation processing agent is adsorbed to the polyester fiber, so that the flame retardation processing agent is promoted to be fixed into the array of molecules of the polyester fiber in a superb state. As a result, even under milder conditions of heat treatment, for example, at 80 to 130° C. and atmospheric pressure to 0.0.2 MPa, the phosphorus compound, in an amount which is sufficient to allow the flame retardant agent to provide the effect of flame retardation, can be fixed to the inside of the polyester fiber stably.

Since the heat treating conditions are thus mild, the thermal influences of the heat treatment step on the polyester fiber (thermal load, thermal hysteresis, etc.) are alleviated. Therefore, the strength reduction and thermal denaturing of the polyester fiber by the heat treatment step can be sufficiently prevented. Further, in this method, the flame retardation processing agent providing step and the heat treatment step may be performed concurrently, or the processing liquid may be heated to the above-described preferable temperature before the polyester fiber is immersed in the processing liquid, like with aforementioned method 2.

An amount of the carrier is preferably 0.1 to 10% o.w.f. (i.e., "on the weight of fiber") with respect to the weight of the polyester fiber to be processed, and more preferably 1.0 to 5.0% o.w.f. When the content of the carrier is too small, the flame retardation processing agent tends not to be sufficiently promoted to be fixed to the polyester fiber. As a result, the flame retarding property of the post-processing polyester fiber may be lowered. When the content of the carrier is too large, the carrier tends not to be emulsified or dispersed in the processing solution.

Further, in order to well emulsify or disperse the carriers in the processing liquid, a surfactant may be appropriately added to the processing liquid. Exemplary surfactants include castor oil sulfated oil, alkylbenzenesulfonate, dialkylsulfosuccinate, polyoxyethylene (POE) castor oil ether, and POE alkylphenylether.

The immersing and heat treatment processing (the flame retardation processing agent providing step and the heat treatment step) for fixing the phosphorus compound existing in the flame retardation processing agent to the polyester fiber may be performed before, concurrently with, or after dyeing of the polyester fiber. It is preferable to perform the immersing and heat treatment processing concurrently with the dyeing in order to reduce the number of steps and work stages to enhance the working efficiency.

In each of methods 1 through 3, it is preferable to perform soaping processing of the polyester fiber by a usual technique after the heat treatment step, so as to remove the phosphorus compound which is not strongly fixed to the polyester fiber but is merely loosely attached to the surface of the polyester fiber.

As the washing liquid for the soaping processing, usual anionic, nonionic, ampholytic surfactants and detergents containing these surfactants are usable.

When a high level of washing durability is not required of the polyester fiber, it is not necessary that the phosphorus compound existing in the flame retardation processing agent be strongly fixed to the surface of the polyester fiber, and the phosphorus compound can merely be loosely attached to the surface of the fiber. In this case, the heat treatment step can be substantially omitted. Even in a state where the phosphorus compound is loosely attached to the surface of the polyester fiber, the polyester fiber can be provided with a flame retarding property.

(Flame Retardant Agent for a Polyurethane Resin)

The above-described phosphorus compounds have excellent performance as flame retardant agents for a polyurethane resin.

As flame retardant agents for a polyurethane resin according to the present invention, the compounds represented by formula (I) are usable. The details thereof (for example, the specific examples and production methods thereof) are as provided in this specification regarding the corresponding compounds.

Also, as flame retardant agents for a polyurethane resin according to the present invention, the compounds represented by formula (III) are usable. The details thereof (for example, the specific examples and production methods thereof) are as provided in this specification regarding the corresponding compounds.

These flame retardant agents for a polyurethane resin are especially useful for a polyurethane foam.

The amount of a phosphorus compound mentioned above when used as a flame retardant agent for a polyurethane resin may be appropriately determined in accordance with the required degree of flame retarding property. When the amount is too small, it is likely that a sufficient flame retarding effect is not obtained. When the amount is too large, the phosphorus compound may undesirably have an adverse effect on the physical properties of the obtained resin composition. The amount of the phosphorus compound is preferably 0.1 parts by weight or greater with respect to 100 parts by weight of the polyol component in the polyurethane resin, more preferably 1 part by weight or greater, and still more preferably 5 parts by weight or greater. The amount of the phosphorus compound is preferably 60 parts by weight or less with respect to 100 parts by weight of the polyol component in the polyurethane resin, more preferably 40 parts by weight or less, and still more preferably 30 parts by weight or less.

(Polyol Component)

As the polyol component for a polyurethane resin composition according to the present invention, various types of polyols known as polyols for polyurethane resins are usable. Specific examples includes polyether polyols, polyester polyols, and polymer polyols. Any type of polyol generally used as a material of polyurethane is usable with no specific limitation. Polyols containing about 2 to 15 hydroxyl groups per molecule is preferable, and polyol containing about 2 to 8 hydroxyl groups per molecule is more preferable. The molecular weight of the polyol is preferably about 100 to 20000, and more preferably about 250 to 6500. When the molecular weight of polyol is in this range, the activity and viscosity suitable for forming urethane foam are easily obtained. When the molecular weight of polyol is too large or too small, superb urethane foam is not easily obtained.

For example, polyether polyols are obtained by adding an alkylene oxide such as ethylene oxide, propylene oxide or the like to a glycol such as ethylene glycol, propylene glycol or the like; triols such as glycerin, trimethylol propane or the like; polyfunctional polyols such as pentaerythritol, sorbitol, saccharose or the like; or amine compounds such as ammonia, triethanolamine, ethylenediamine, diethylenetriamine, aminoethylpiperazine, aniline or the like. The addition may be performed randomly or in a block. Specifically, exemplary usable polyether polyol products include Diol-700 of bifunctional polypropyleneglycol type (hydroxyl value: 0.160.0 KOHmg/g; produced by Mitsui Takeda Chemicals, Inc.), MN-3050 ONE of trifunctional polypropyleneglycol type (hydroxyl value: 56.0 KOHmg/g; produced by Mitsui Takeda Chemicals, Inc.), Sannix FA-311S of polyfunctional polypropyleneglycol type (hydroxyl value: 42.0 KOHmg/g; produced by Sanyo Chemical Industries, Ltd.), and SU-464 of polyfunctional polypropyleneglycol type (hydroxyl value: 460 KOHmg/g; produced by Mitsui Takeda Chemicals, Inc.).

Polyester polyol is a compound which is obtained by polycondensation of a polyfunctional carboxylic acid and a polyfunctional hydroxyl compound, and has hydroxyl groups at termini. Examples of polyester polyols include adipic acid-based polyester, phthalic acid-based polyester, azelaic acid polyester, sebacic acid polyester, and polycaprolactone polyester. Specifically, exemplary usable polyester polyol products include ES-30 and ES-40 of phthalic acid-based polyester type (produced by Mitsui Takeda Chemicals, Inc.), ODX2, 460 of azelaic acid and sebacic acid polyester type which are long chain dibasic acids (produced by Dainippon Ink and Chemicals, Inc.), and PMAZ (produced by Kuraray Co., Ltd.).

Polymer polyol can be obtained by mixing a polyether polyol and an ethylenic unsaturated monomer, optionally adding a chain transfer agent, a dispersion stabilizer or the like, and radical-polymerizing the ethylenic unsaturated monomer in the presence of a radical initiator. Exemplary ethylenic unsaturated monomers include cyano group-containing monomers including acrylonitrile, and methacrylonitrile; (meth)acrylic esters including methyl(meth)acrylate, butyl(meth)acrylate, stearyl(meth)acrylate, hydroxyethyl (meth)acrylate, dimethylaminoethyl(meth)acrylate, and dimethylaminopropyl(meth)acrylate; carboxyl group-containing monomers including acrylic acid, methacrylic acid, itaconic acid, maleic acid, and fumaric acid; anhydride-containing monomers including maleic anhydride, and itaconic anhydride; hydrocarbon compounds including butadiene, isoprene, and 1,4-pentadiene; aromatic hydrocarbon compounds including styrene, α-methylstyrene, phenylstyrene, and chlorostyrene; halogen-containing monomers including vinyl chloride, and vinylidene chloride; vinyl ethers including vinyl ethyl ether, and vinyl butyl ether; vinyl ketones including vinyl ethyl ketone; vinyl esters including vinyl acetate; acrylamide-type monomers including acrylamide, N,N-dimethylacrylamide, N-isopropylamide, N,N-dimethylaminopropylacrylamide, and methylenebisacrylamide; and methacrylamide-type monomers including N,N-dimethylmethacryloyl amide. These ethylenic unsaturated monomers may be used independently, or a mixture of two or more of these may be used. Specifically, exemplary ethylenic unsaturated monomer products include POP-90/20 (hydroxyl value: 36.0 KOHmg/g; produced by Mitsui Takeda Chemicals, Inc.), Sannix FL-555 (hydroxyl value: 30.0 KOHmg/g; produced by Sanyo Chemical Industries, Ltd.).

The above-mentioned polyols may be used independently, or a mixture of two or more of these may be used, in accordance with the properties required of the polyurethane foam to be formed.

(Polyisocyanate)

Polyisocyanate is a compound having two or more isocyanate groups in the molecule. For polyurethane resin compositions according to the present invention, any conventionally known polyisocyanate usable for polyurethane resins may be used. Usable polyisocyanate compounds include, for example, aromatic polyisocyanate, aliphatic polyisocyanate, and alicyclic polyisocyanate. Modified polyisocyanate obtained by modifying these polyisocyanates may be used. A mixture of two or more types of polyisocyanates may be optionally used.

Usable exemplary polyisocyanate compounds include tolylene diisocyanate, diphenylmethane diisocyanate, polymethylenepolyphenylene polyisocyanate (crude MDI), xylylene diisocyanate, isophorone diisocyanate, and hexamethylene diisocyanate. Modified polyisocyanates obtained by modifying the aforementioned polyisocyanates, for example, carbodiimide-modified polyisocyanates, biuret-modified polyisocyanates, dimers, trimers of the above and the like are usable. Terminal isocyanate group prepolymers and the like obtained from these polyisocyantes and active hydrogen compounds may also be used. Specifically, exemplary polyisocyanate compound products include Cosmonate T-80 (produced by Mitsui Takeda Chemicals, Inc.), Cosmonate T-65 (produced by Mitsui Takeda Chemicals, Inc.), Cosmonate T-100 (produced by Mitsui Takeda Chemicals, Inc.), Cosmonate M-200 (produced by Mitsui Takeda Chemicals, Inc.), Cosmonate LL (produced by Mitsui Takeda Chemicals, Inc.), and Cosmonate PM-80 (produced by Mitsui Takeda Chemicals, Inc.).

For the polyurethane resin compositions according to the present invention, it is especially preferable to use tolylene diisocyanate (TDI) having isomers such as 2,4-tolylene diisocyanate, 2,6-tolylene diisocyanate, and the like and/or diphenylmethane 4,4'-diisocyanate (MDI). These diisocyanates may be used independently, or a mixture of two or more of these may be used.

The amount of the polyisocyanate component is not specifically limited, and any amount of polyisocyanate component may be used as long as polyurethane is formed by reaction of the polyisocyanate component and the polyol. Accordingly, the amount may be appropriately determined so as to allow the urethane synthesis reaction to proceed in a superb manner, in consideration of the total molar number of the isocyanate group in the polyisocyanate component, the total molar number of the hydroxyl group in the polyol, and the molar number of water in the foaming agent. Regarding the determination of the amount, the term "isocyanate index" is often used. The term "isocyanate index" means the ratio of polyisocyanate with respect to the amount of polyisocyanate stoichiometrically necessary for reaction with an active hydrogen-containing compound such as polyol or water (the stoichiometrically necessary amount of polyisocyanate being 100). For flexible polyurethane foam, the amount of polyisocyanate represented by an isocyanate index is preferably about 90 to 120, more preferably about 95 to 115, and still more preferably about 100 to 115. For rigid polyurethane foam, polyisocyanate is usually used in an amount represented by an isocyanate index of about 100 to 110. For polyisocyanurate foam (PIR), the amount of polyisocyanate represented by an isocyanate index is preferably about 180 to 300, and more preferably about 220 to 260. When the amount of polyisocyanate is too large or too small, it is likely to be difficult to obtain a polyurethane foam having superb physical properties.

(Catalyst)

For the polyurethane resin compositions according to the present invention, a catalyst is optionally added. Various types of conventionally known catalysts for promoting a reaction for synthesizing polyurethane are usable with no specific limitation. Usable catalysts are roughly classified into amine catalysts and metal catalysts. Exemplary amine catalysts include triethylenediamine, dimethylethanolamine, and N-ethylmorpholine. Representative metal catalysts are organic metal compounds encompassing various metals, for example, tin, copper, zinc, cobalt, and nickel. Especially, tin catalysts including stannous octate and dibutyltindilaurate are preferably used. Organic metal catalysts are preferably used for producing flexible polyurethane slab foam.

The amount of an amine catalyst to be used is preferably about 0.05 to 1.0 part by weight with respect to 100 parts by weight of the polyol component. The amount of an organic metal catalyst relies on the degree of activity. In the case of stannous octate, for example, the amount is about 0.01 to 0.8 parts by weight with respect to 100 parts by weight of the polyol component.

For the urethane resin compositions according to the present invention, an organic metal catalyst is not indispensable. Accordingly, addition of a catalyst is not necessary in the case where a sufficient urethane synthesis reaction can be performed without a catalyst. For example, an organic metal catalyst is not generally used for producing rigid polyurethane foam.

(Silicone Foam Stabilizer)

A silicone foam stabilizer is generally used for the urethane resin compositions according to the present invention. For producing flame retardant flexible or rigid polyurethane foam, use of a silicone foam stabilizer facilitates mixture and emulsification of starting materials and dispersion of incorporated gas. In addition, use of a silicone foam stabilizer provides the effects of, for example, preventing aggregation of foam and stabilizing cell films. Thus, foam having higher characteristics can be provided.

Exemplary silicone foam stabilizers usable for the present invention include a block copolymer of dimethylpolysiloxane and polyether. The molecular structure of the block copolymer which is available is in the form of a straight chain, a branched chain, a pendant, or the like. Especially, branched chain- or pendant-type copolymers are often used. For the present invention, various silicone foam stabilizers to be used conventionally used for flexible or rigid polyurethane foam can be appropriately selected and used, with no specific limitation.

The amount of a silicone foam stabilizer to be used is preferably 0.2 parts by weight or greater with respect to 100 parts by weight of the polyol component, and more preferably 0.5 parts by weight or greater. When the amount of silicone foam stabilizer is too small, it is difficult to obtain the effect which should be provided by addition of the silicone foam stabilizer. The amount of a silicone foam stabilizer to be used is preferably 5 parts by weight or less with respect to 100 parts by weight of the polyol component, and more preferably 2 parts by weight or less.

(Foaming Agent)

For producing flexible or rigid polyurethane foam, a foaming agent is usually used. It is very advantageous to use a foaming agent, since when it is not used, it is likely to be difficult to sufficiently foam polyurethane. For the polyurethane resin compositions according to the present invention, known foaming agents used for usual polyurethane foams are usable as a foaming agent. Exemplary foaming agents include water, flon, dichloromethane, n-pentane, and isopentane. These foaming agents may be used independently, or a mixture of two or more of these may be used. Industrially, it is very advantageous to use water for obtaining polyurethane foam. It is preferable to determine whether to use water independently or to use a mixture of water and other foaming agents, depending on the density or other physical properties required of the foam to be produced.

There is no limitation on the amount of a foaming agent which is used for producing polyurethane foam. In the case where water is used as a foaming agent, the amount of water is preferably 0.1 parts by weight or greater with respect to 100 parts by weight of the polyol component, and more preferably 1.0 part by weight or greater. The amount of water is preferably 10 parts by weight or less with respect to 100 parts by weight of the polyol component, and more preferably 6 parts by weight or less. Optionally, a foaming agent other than water may be added at a ratio of 1.0 to 30 parts by weight depending on the density or other physical properties required of the foam to be produced. When the amount of the foaming agent is too small, it is difficult to sufficiently foam polyurethane. When the amount of the foaming agent is too large, the physical properties of the foam may undesirably be lowered.

(Antioxidants)

In the polyurethane resin compositions according to the present invention, an antioxidant may optionally be contained in an amount effective to prevent oxidation. Exemplary antioxidants include hydroquinone compounds and trivalent organic phosphoric acid compounds. A hydroquinone compound is generally represented by formula (VII).

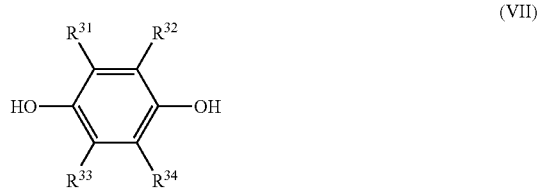

(VII)

(In the formula, $R^{31}$, $R^{32}$, $R^{33}$ and $R^{34}$ are each a hydrogen atom or an alkyl group having a carbon number of 1 through 14.)

Specifically, exemplary hydroquinone compounds include hydroquinone, 2,5-di-tert-butylhydroquinone, 2,5-di-tert-amylhydroquinone, 2,5-dioctylhydroquinone, tert-amylhydroquinone, tert-butylhydroquinone, and octylhydroquinone. 2,5-di-tert-butylhydroquinone and 2,5-di-tert-amylhydroquinone are especially preferable for their high thermal resistance.

Specifically, exemplary trivalent organic phosphorus compounds include triphenyl phosphate, tris(nonylphenyl) phosphate, diphenylisodecyl phosphate, tris(2,4-di-tert-butylphenyl) pentaerythritol diphosphite, and tetrakis-(2,4-di-tert-butylphenyl)-4,4-diphenylene phosphonite.

An antioxidant can be used as follows. An antioxidant is added to the polyol before mixed with polyisocyanate or added to a flame retardant agent (organic phosphorus compound), and then mixed uniformly. The amount of an antioxidant is preferably 0.1 to 5 parts by weight with respect to 100 parts by weight of a polyurethane resin composition, and more preferably 0.2 to 2 parts by weight. When the amount of the antioxidant is in this range, an effective anti-oxidation effect is provided. When long-term stability is not required, an antioxidant is not necessary.

(Other Components)

To the polyurethane resin compositions according to the present invention, additives may optionally be added as other components in such a range that no adverse influence is exerted on the resultant resin composition. The additives which can be added include, for example, other flame retardant agents such as melamine and the like, flame-retarding adjuvants, colorants, crosslinking agents, antioxidants, ultraviolet absorbers, hydrolysis prevention agents, and fillers. There is no specific limitation on the type and amount of these additives. Additives usually used may be used in an amount of usual ranges.

(Method for Mixing Compositions)

There is no limitation on the method for mixing, or the order of mixing, the components of the polyurethane resin compositions. The components can be mixed by any method in any order. According to a generally preferable method, the components other than polyisocyanate are stirred and mixed, then polyisocyanate is added just before foaming, and the mixture is foamed.

(Other Resin Product Uses)

In this specification, a method of using a flame retardant agent according to the present invention is described in detail especially regarding polyester fiber and polyurethane foam. The reason is that the effects of the flame retardant agent according to the present invention are highly advantageous in these uses. However, the uses of the flame retardant agent according to the present invention are not limited to these, and the flame retardant agent is usable for polyester in forms other than fiber and also for polyurethane in forms other than foam. The flame retardant agent according to the present invention is also usable for thermoplastic resins other than polyester and polyurethane (for example, polyolefin) and thermosetting resins.

EXAMPLES

The present invention will be described by way of specific test examples and comparative test examples. The present invention is not limited by these examples.

Synthesis Example 1

Synthesis of Phosphorus Compound (1)

(Synthesis of Material 1)

A 1-liter four-neck flask equipped with a stirrer, a thermometer, a dripping device, a hydrochloric acid recovering device and a reflux tube was filled with 208.0 g (2 mol) of neopentylglycol and 135 g of toluene. While the mixed solution was stirred, 307.0 g (2 mol) of phosphorus oxychloride was added thereto at 50° C. over 1 hour. After the termination of the addition, the temperature was raised from 50° C. to 70° C. over 2 hours to cause a reaction. 125.6 g of the generated hydrogen chloride was recovered. After that, the pressure was lowered at 70° C. to 33 kPa over 1 hour, thereby removing the remaining hydrogen chloride gas generated as a by-product. Then, the resultant substance was recrystallized, thereby obtaining neopentylene phosphorochloridate (material 1) as a reaction product. Material 1 had a purity measured by GPC (gel permeation chromatography) of 100% by area, and an amount of 221.4 g (yield: 60%). Material 1 had a melting point of 105.0° C. and exhibited the state of white crystals.

(Synthesis of Intermediate 1)

A 1-liter four-neck flask equipped with a stirrer, a thermometer, a dripping device, a hydrochloric acid recovering device and a reflux tube was filled with 208.0 g (2 mol) of neopentylglycol, 36.0 g (2 mol) of water, and 200 g of toluene. While the mixed solution was stirred, 274.6 g (2 mol) of phosphorus trichloride was added thereto at 40° C. over 2 hours. After the termination of addition, the temperature was raised to 120° C. over 1 hour. Then, the substances were reacted at the same temperature (120° C.) for 30 minutes. 214.2 g of the generated hydrogen chloride was recovered. After that, the pressure was lowered at 60° C. at 53 kPa over 2 hours, thereby removing the remaining hydrogen chloride gas generated as a by-product. While the temperature was maintained at 60° C., the pressure was gradually lowered. Toluene was recovered until the pressure was finally lowered to 2.0 kPa. Thus, 311.4 g of a reaction product was obtained. The reaction product had a purity measured by GPC (gel permeation chromatography) of 95.6% by area. The obtained reaction product was distilled at 127° C. and 0.27 kPa, thereby obtaining neopentylene phosphate (intermediate 1) having a purity of 100% and an amount of 241.2 g (yield: 80.4%). Intermediate 1 had a melting point of 56.0° C. and exhibited the state of white crystals.

(Synthesis of Intermediate 2)

A fresh 2-liter four-neck flask equipped with a stirrer, a thermometer, a dripping device, and a reflux tube was filled with 31.9 g (1 mol) of 94% paraformaldehyde, 90 g of 1,2-dichloroethane, and 3.0 g (0.03 mol) of triethylamine. While the mixed solution was stirred, a mixed solution of 150.1 g (1 mol) of intermediate 1 and 90 g of 1,2-dichloroethane was added thereto at 60° C. over 2 hours. After that, the substances were reacted at the same temperature (60° C.) for 1 hour, thereby obtaining a solution containing neopentylene (hydroxymethyl) phosphonate (intermediate 2) as a main component. A purity measured by GPC (gel permeation chromatography) excluding the solvent and triethylamine was 95.8% by area. The pure yield in the solution was 96.0%. Triethylamine used as a catalyst and 1,2-dichloroethane used as a solvent were not recovered since they were to be used for the next step.

In order to examine the physical properties of intermediate 2, a part of the solution containing intermediate 2 as a main component was sampled, and the solvent and triethylamine were removed in the same manner as described in the above section "Synthesis of intermediate 1". Intermediate 2 was found to have a melting point of 116.0° C. and exhibit the state of white crystals.

(Synthesis of Phosphorus Compound (1))

The flask accommodating the post-reaction solution containing intermediate 2 was filled with 121.4 g (1.2 mol) of triethylamine, 1.85 g (0.015 mol) of 4-(dimethylamino) pyridine, and 420 g of 1,2-dichloroethane. While the mixed solution was stirred, a mixed solution of 177.1 g (0.96 mol) of material 1 and 450 g of 1,2-dichloroethane was added thereto at 20° C. over 2 hours. After that, the substances were reacted at the same temperature (20° C.) for 8 hours. The obtained post-reaction solution was neutralized at room temperature using an aqueous solution of hydrochloric acid in an amount corresponding to the excess amount of triethylamine. The resultant solution was kept still so as to be separated into different layers. Then, the organic layer was neutralized using an aqueous solution of sodium hydrogen carbonate. The organic layer was then washed with water twice. The obtained organic layer was dried by anhydrous magnesium sulfate. Toluene was added to the filtrate, and recrystallization was performed. Thus, 171.4 g of phosphorus compound (1) was obtained. Phosphorus compound (1) had a purity measured by GPC (gel permeation chromatography) of 100% by area. The yield was 54.4%.

The overall yield with respect to phosphorus trichloride was:

(intermediate 1)80.4%×(intermediate 2)96.0%×(phosphorus compound 1)54.4%=42.0%.

Figure 1B:
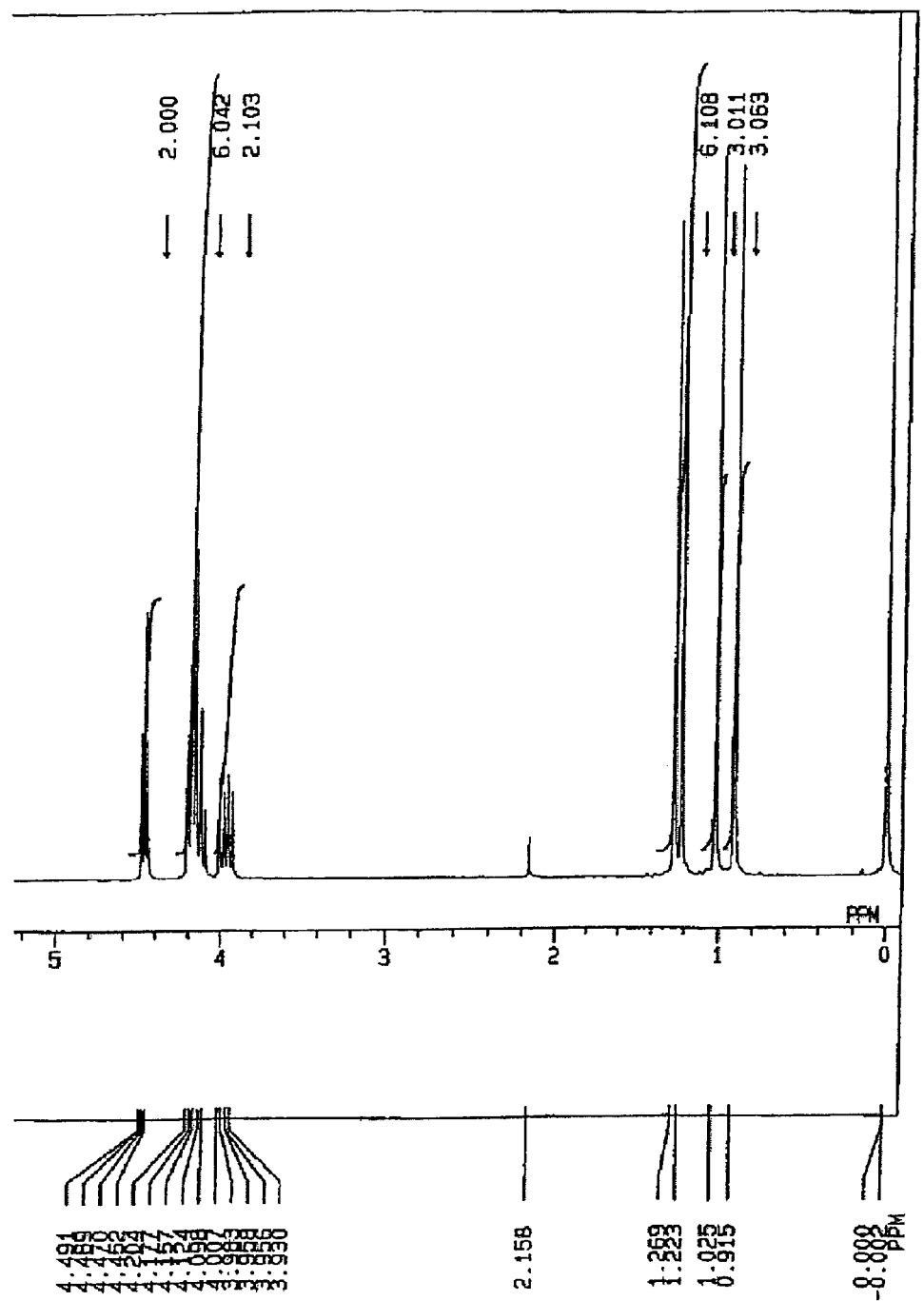
FIG. 1B shows a partially enlarged view of the $^1$H-NMR chart of phosphorus compound (1).
Figure 2A:
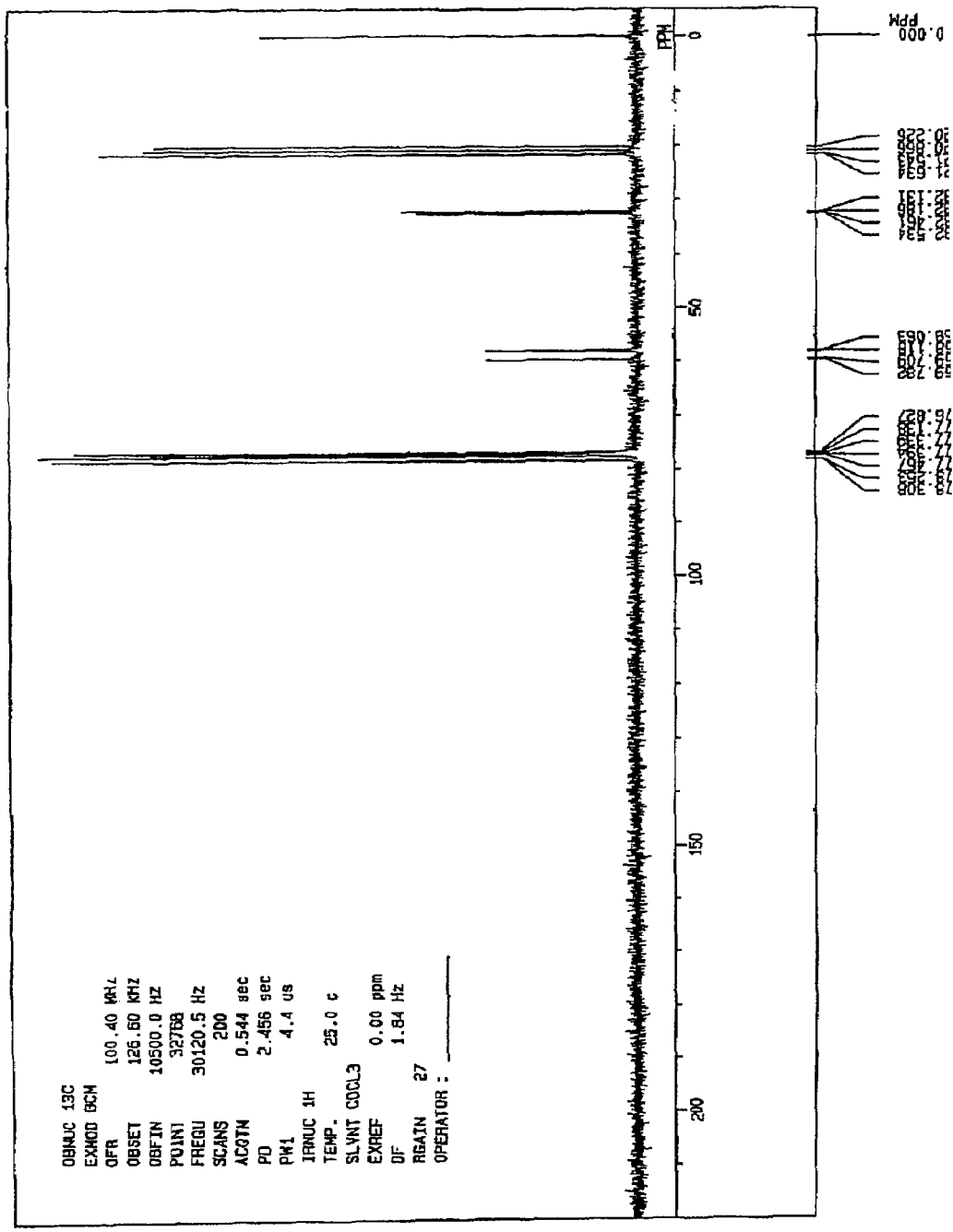
FIG. 2A shows a $^{13}$C-NMR chart of phosphorus compound (1).
Figure 2B:
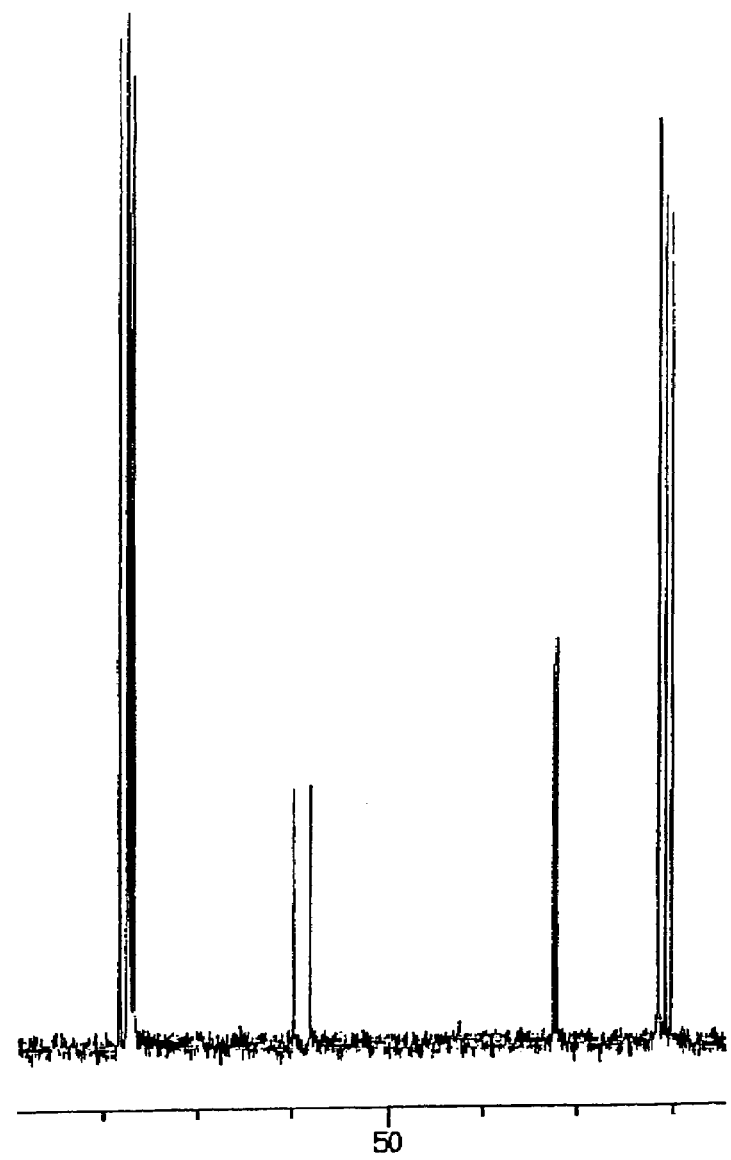
FIG. 2B shows a partially enlarged view of the $^{13}$C-NMR chart of phosphorus compound (1).
Figure 2B:
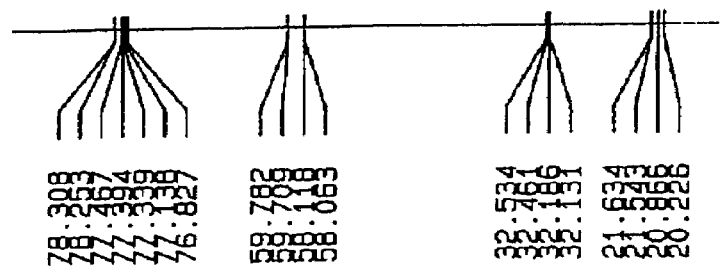
Figure 3A:
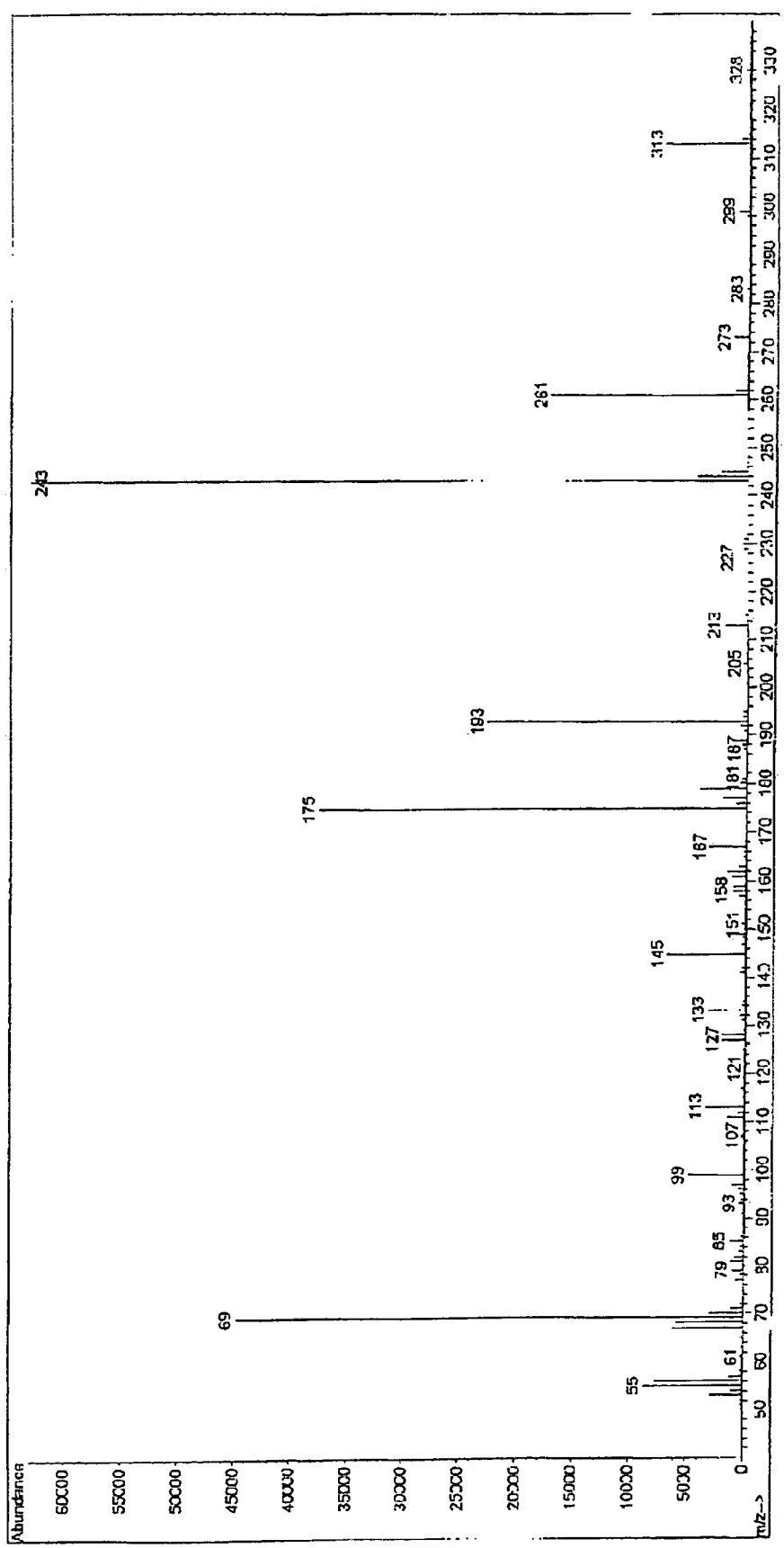
FIG. 3A shows a GC-MS chart of phosphorus compound (1).
Figure 3B:
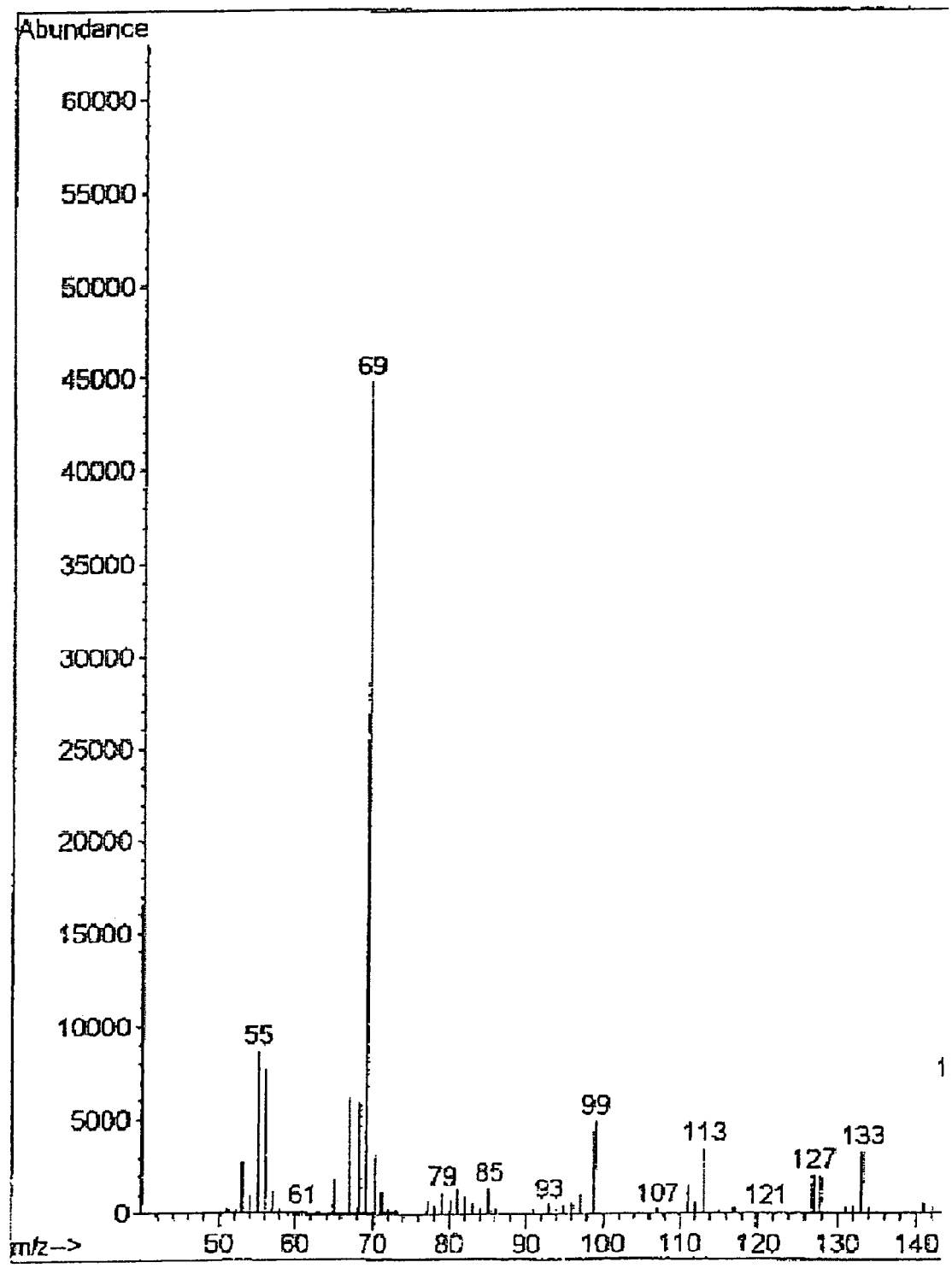
FIG. 3B shows a partially enlarged view of the GC-MS chart of phosphorus compound (1).
Figure 3C:
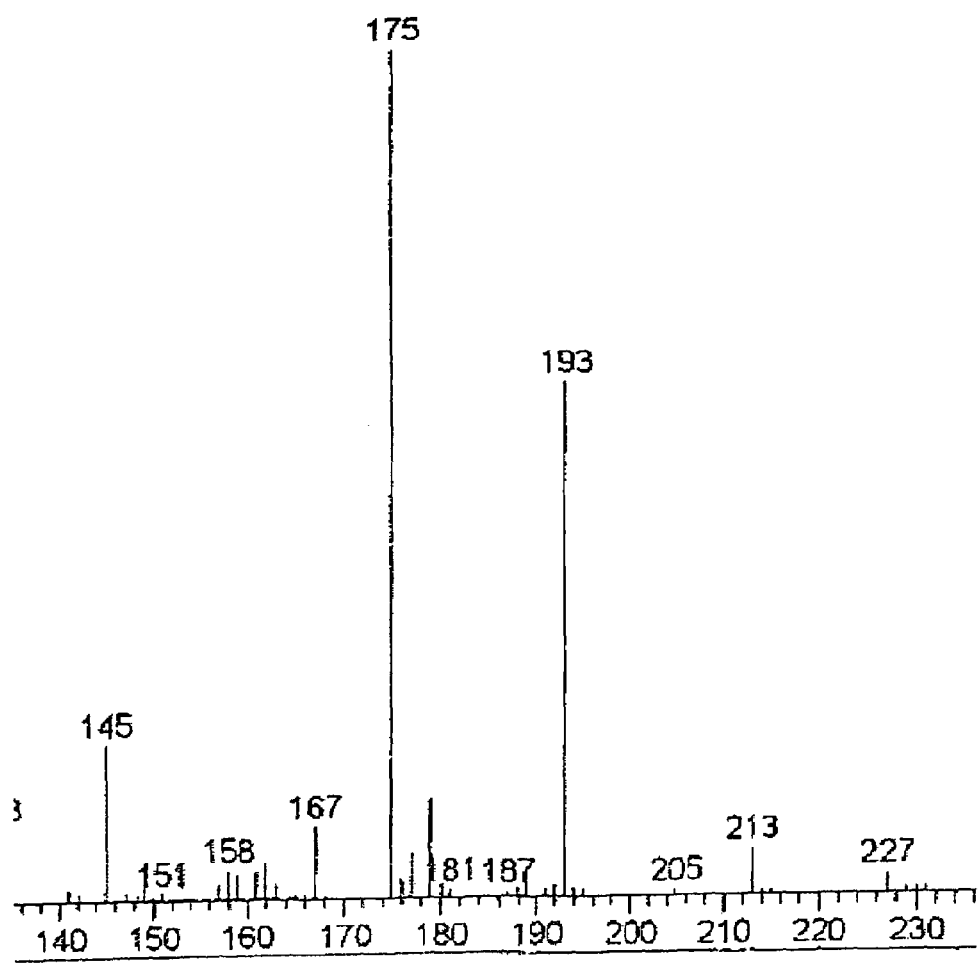
FIG. 3C shows a partially enlarged view of the GC-MS chart of phosphorus compound (1).
Figure 3D:
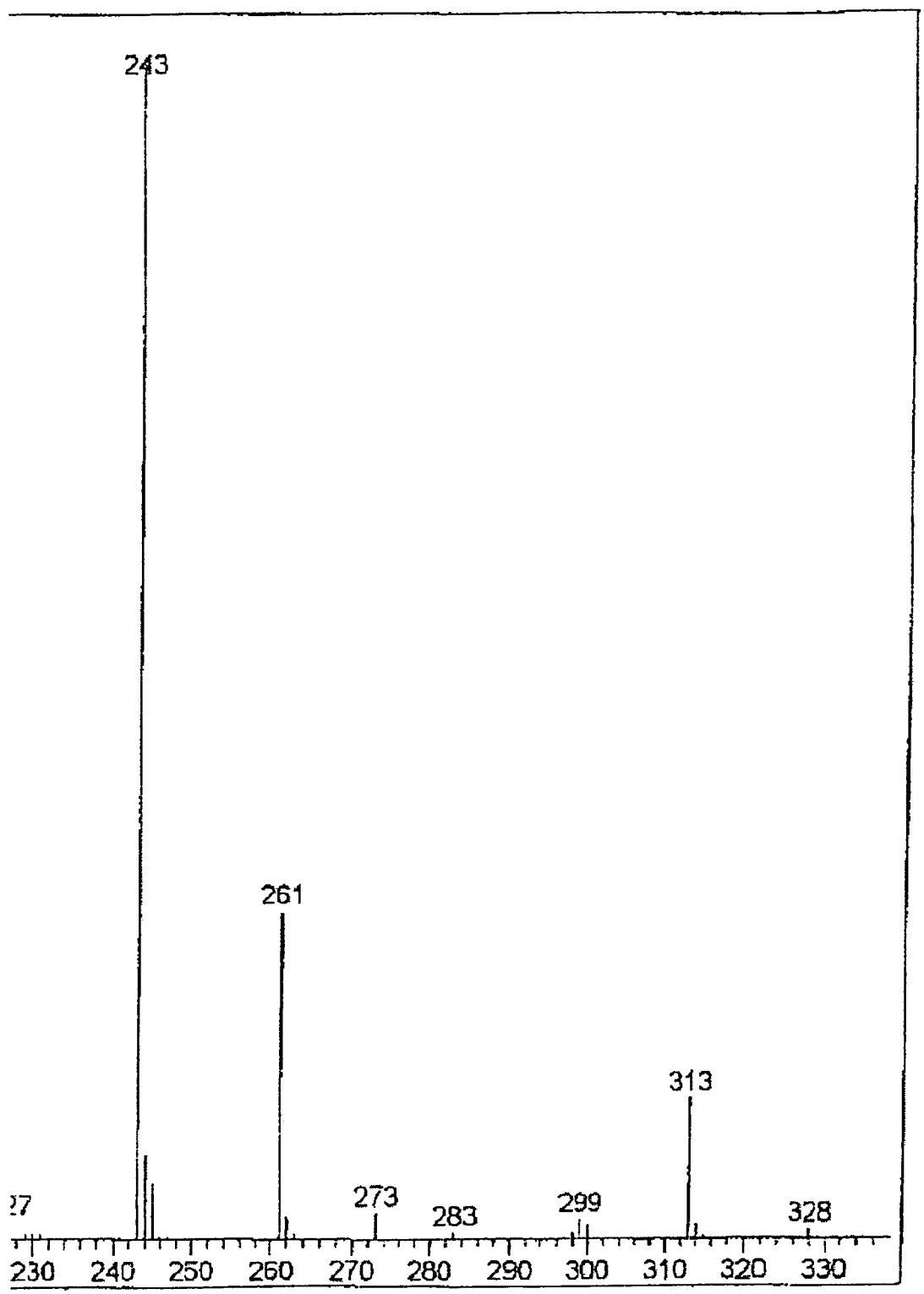
FIG. 3D shows a partially enlarged view of the GC-MS chart of phosphorus compound (1).

The obtained product had a melting point of 152.0° C. and exhibited the state of white crystals. Table 1 shows the elemental analysis results and the quantization value of phosphorus measured using a UV spectroscope. The measured values substantially matched the theoretical values. Regarding FT-IR, the infrared absorption area was quantitated numerically as shown below. $^1$H-NMR, $^{13}$C-NMR, and GC-MS chart are respectively shown in FIGS. 1A and 1B, FIGS. 2A and 2B, and FIGS. 3A through 3D. From the above results, the obtained product was confirmed to be a compound represented by the following chemical formula.

TABLE 1

| | Measured value (%) | Theoretical value (%) |
|---|---|---|
| Carbon | 40.2 | 40.3 |
| Hydrogen | 6.6 | 6.7 |
| Phosphorus | 18.9 | 18.9 |

IR(KBr): 2976, 1482, 1378, 1334, 1288, 1084, 1048, 1002, 983, 955, 922, 863, 830, 818, 624, 615, 528, 498, and 466 cm$^{-1}$.

Compound VI:

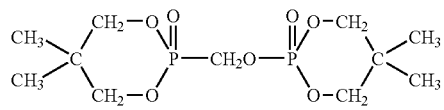

Synthesis Example 2

Synthesis of Phosphorus Compound (2)

The flask accommodating the post-reaction solution containing intermediate 2 in synthesis example 1 was filled with 121.4 g (1.2 mol) of triethylamine and 420 g of 1,2-dichloroethane. While the mixed solution was stirred, 257.8 g (0.96 mol) of diphenyl phosphorochloridate (DPC; produced by Daihachi Chemical Industry Co., Ltd.) was added thereto at 20° C. over 1 hour. After that, the substances were reacted at the same temperature (20° C.) for 3 hours. The obtained post-reaction solution was neutralized at room temperature using an aqueous solution of hydrochloric acid in an amount corresponding to the excess amount of triethylamine. The resultant solution was kept still so as to be separated into different layers. Then, the organic layer was neutralized using an aqueous solution of sodium hydrogen carbonate. The organic layer was then washed with water twice. The obtained organic layer was dried by anhydrous magnesium sulfate. The solvent and water were removed by distillation. Thus, 251.0 g of phosphorus compound (2) was obtained. Phosphorus compound (2) had a purity measured by GPC (gel permeation chromatography) of 93.0% by area. The yield was 63.5%.

The overall yield with respect to phosphorus trichloride was:

(intermediate 1)80.4%×(intermediate 2)96.0%×(phosphorus compound 2)63.5%=49.0%.

Figure 4A:
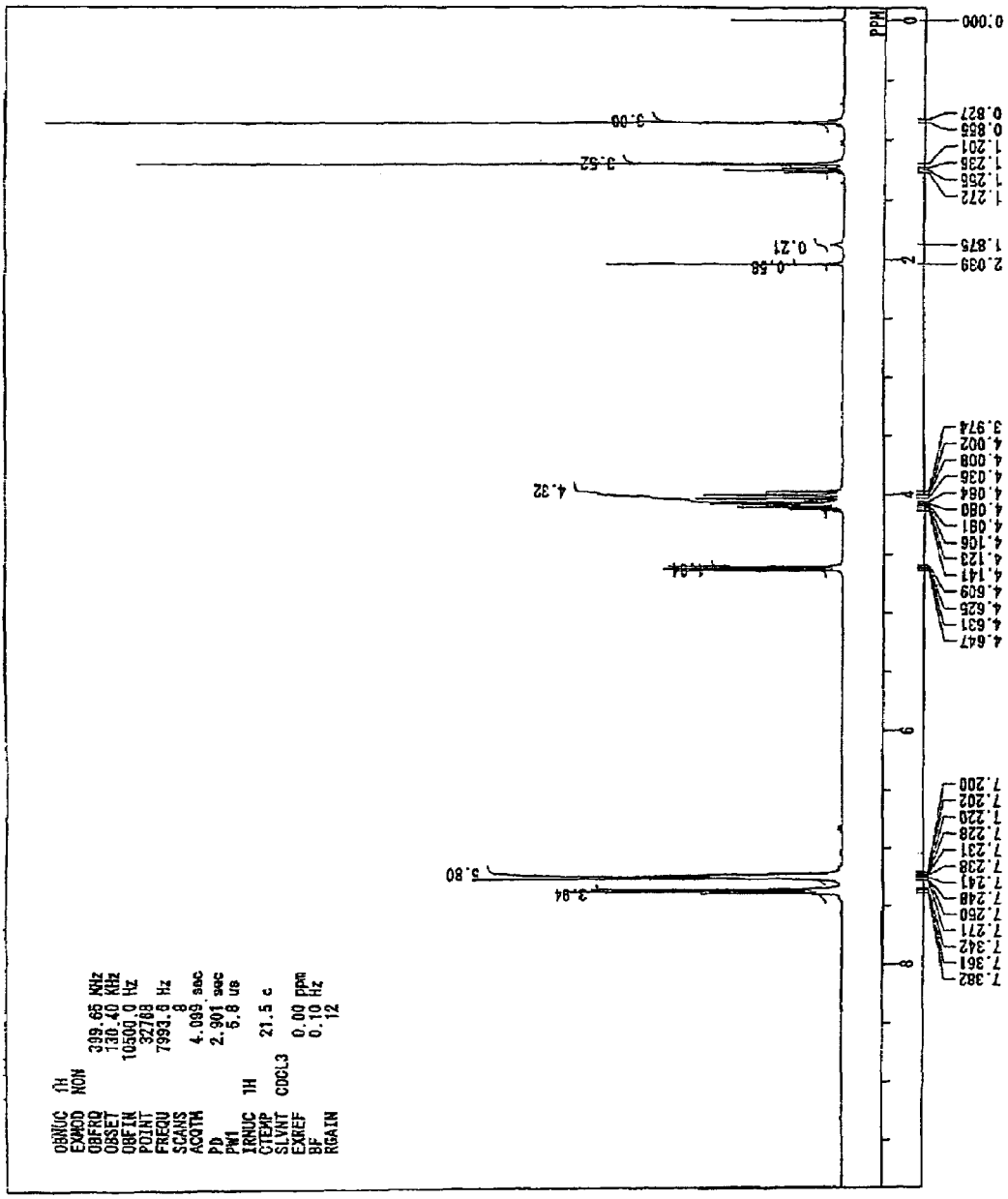
FIG. 4A shows a $^1$H-NMR chart of phosphorus compound (2).
Figure 4B:
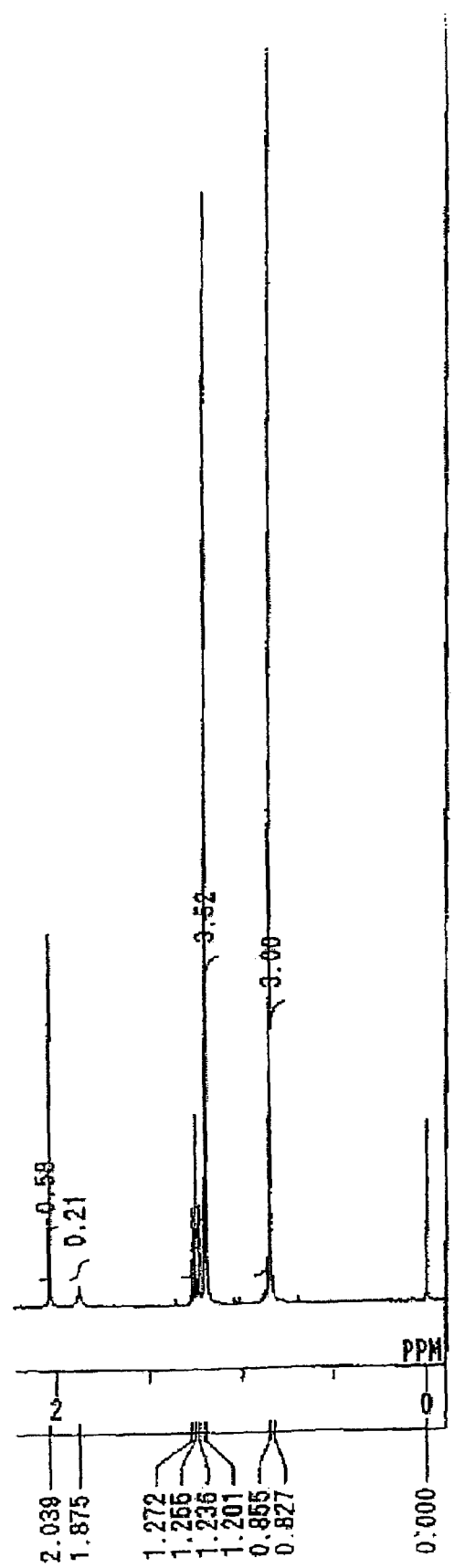
FIG. 4B shows a partially enlarged view of the $^1$H-NMR chart of phosphorus compound (2).
Figure 4D:
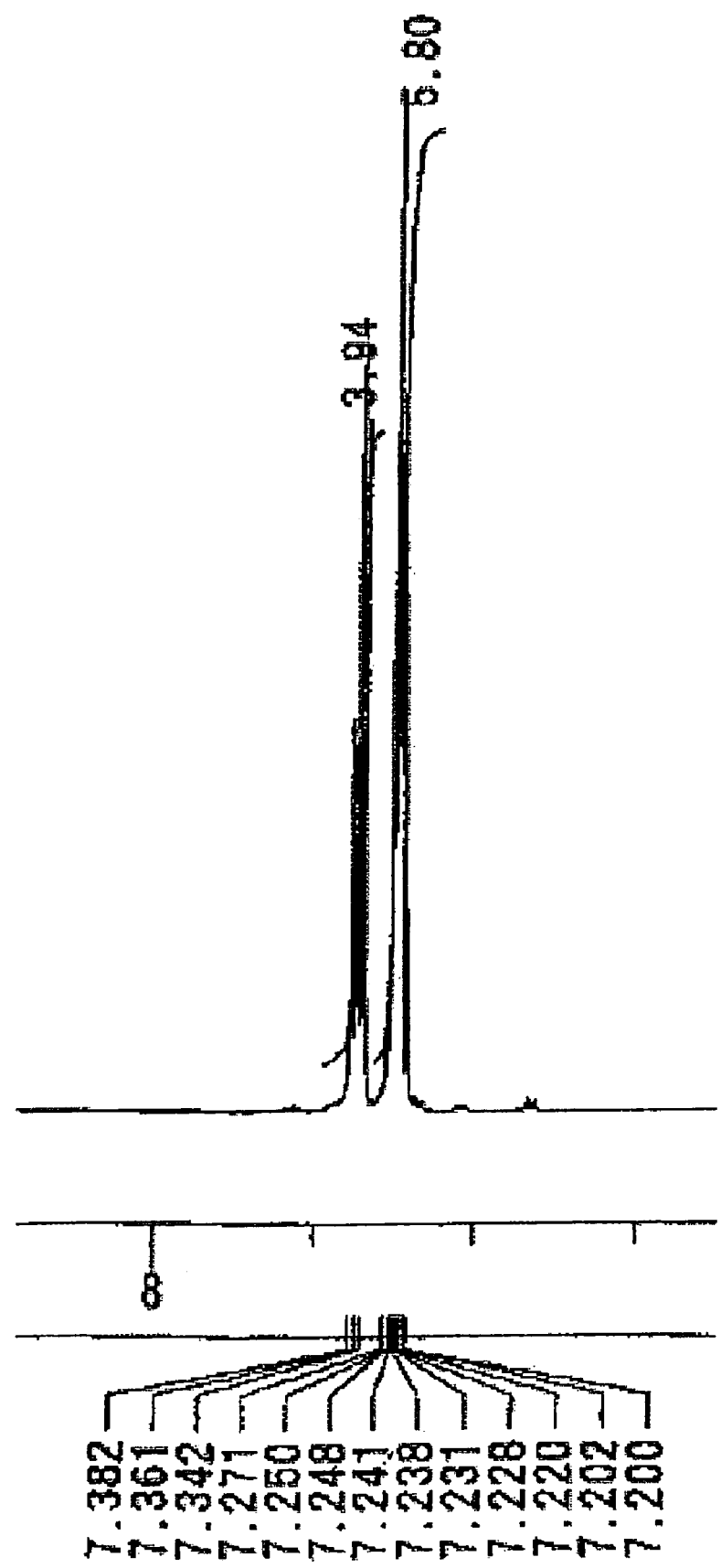
FIG. 4D shows a partially enlarged view of the $^1$H-NMR chart of phosphorus compound (2).
Figure 5A:
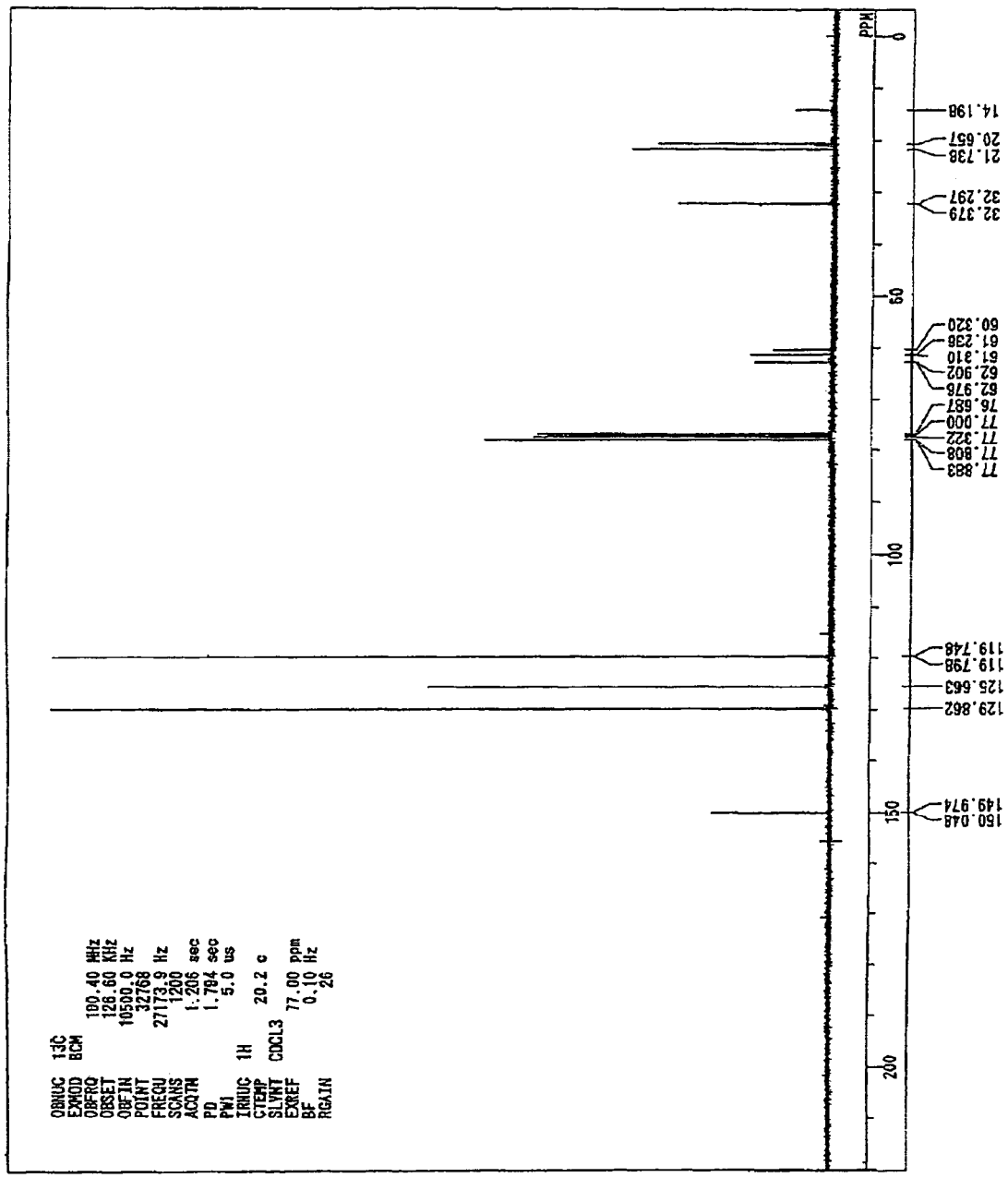
FIG. 5A shows a $^{13}$C-NMR chart of phosphorus compound (2).
Figure 5B:
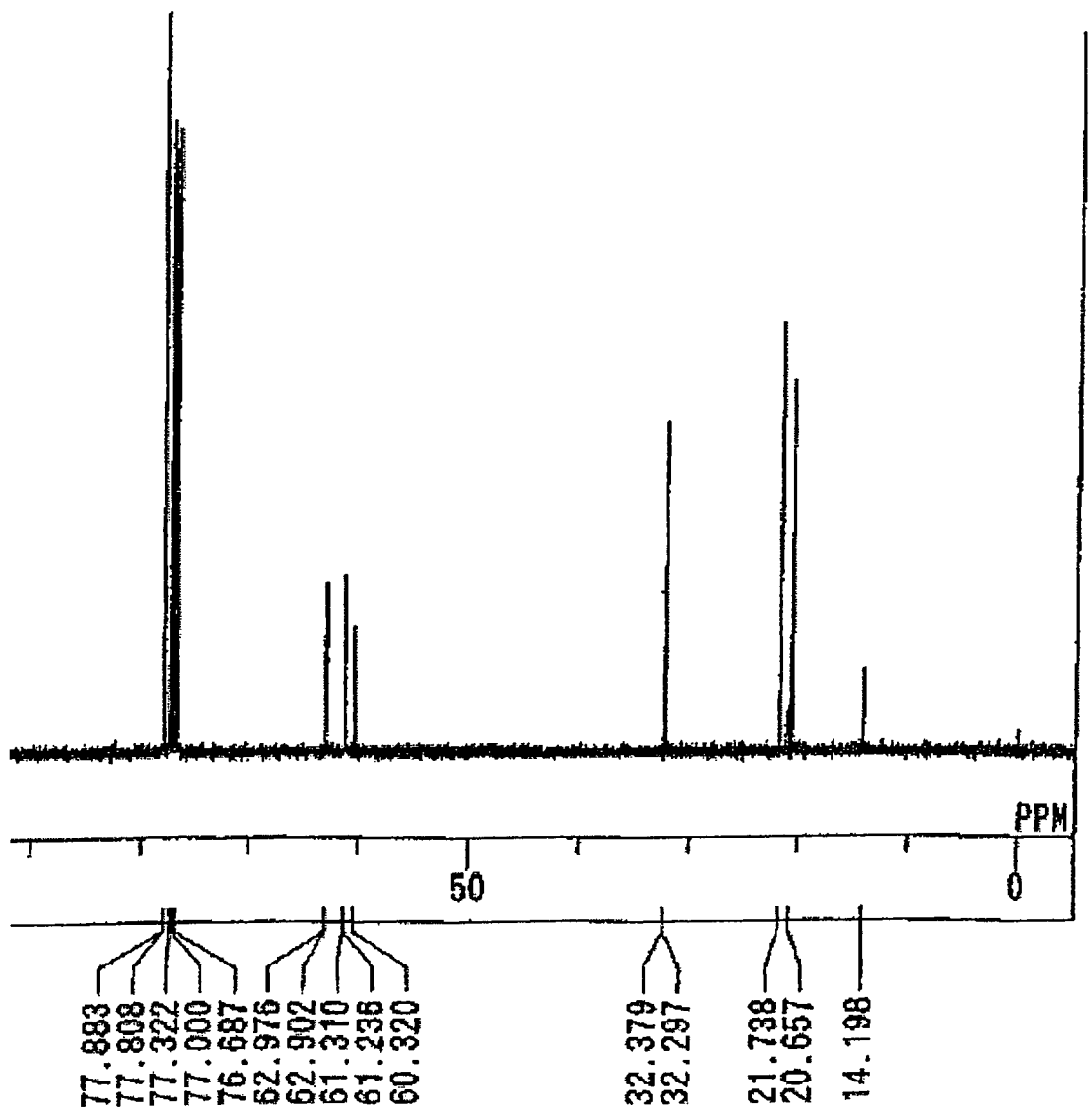
FIG. 5B shows a partially enlarged view of the $^{13}$C-NMR chart of phosphorus compound (2).
Figure 6A:
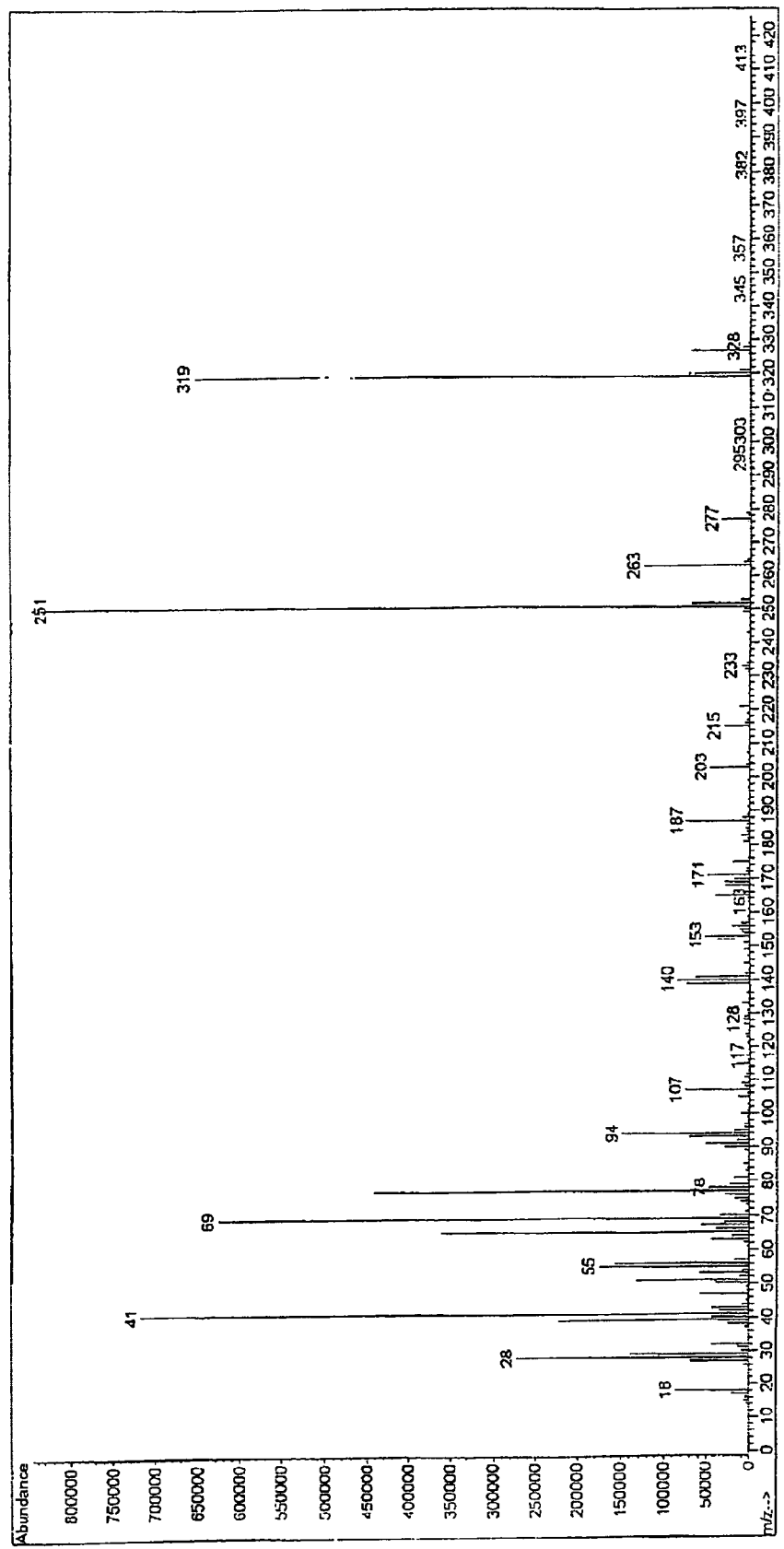
FIG. 6A shows a GC-MS chart of phosphorus compound (2).
Figure 6B:
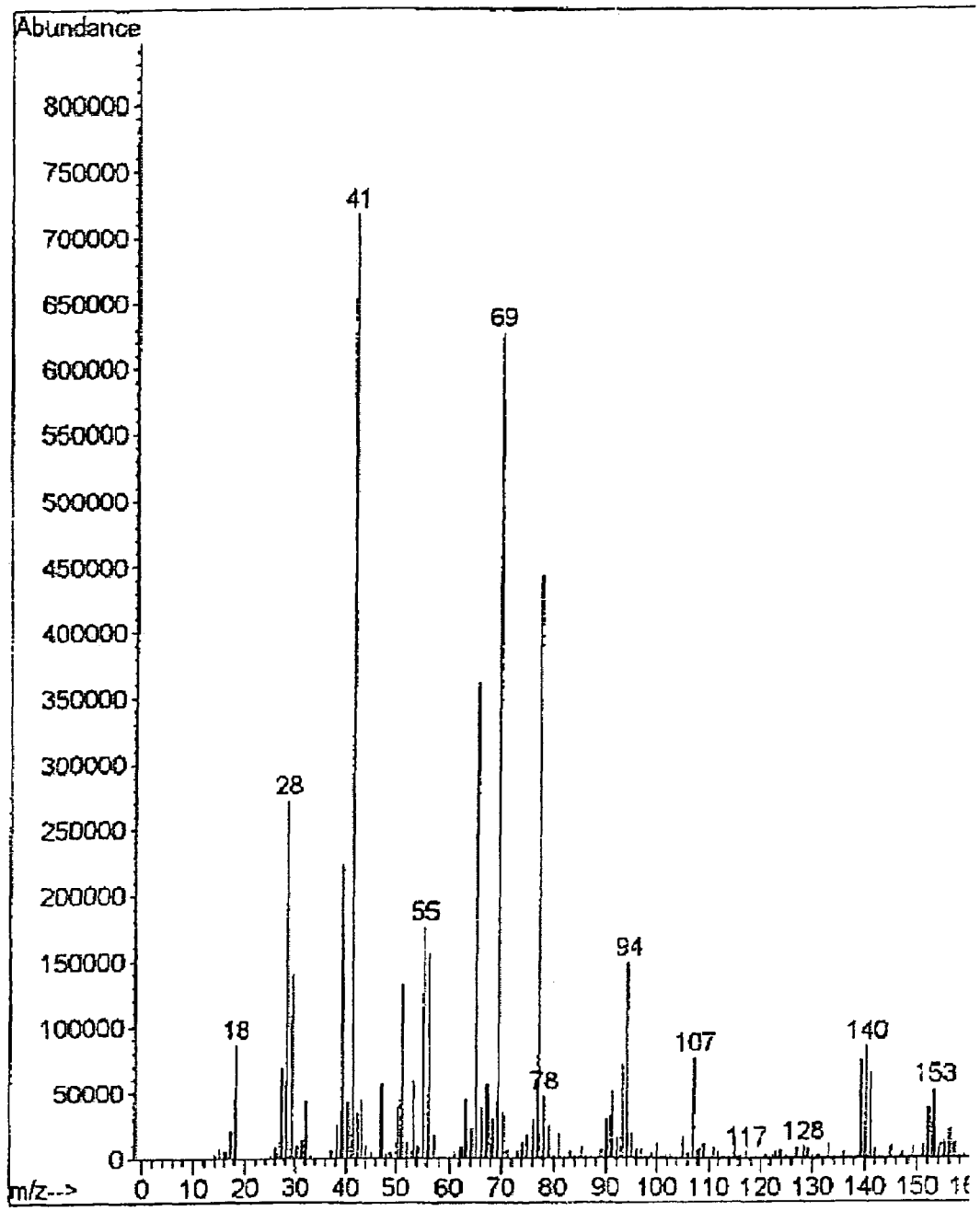
FIG. 6B shows a partially enlarged view of the GC-MS chart of phosphorus compound (2).
Figure 6C:
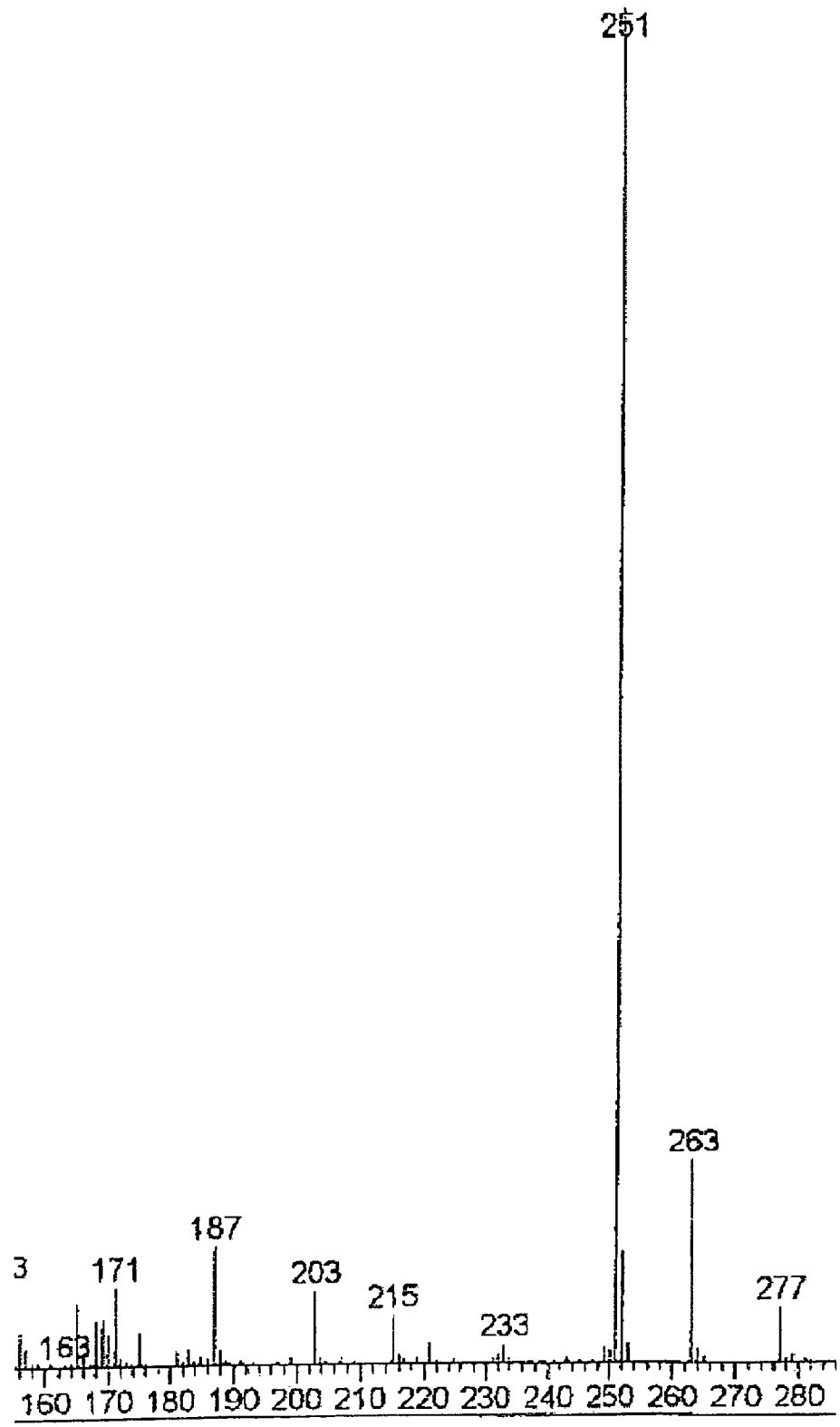
FIG. 6C shows a partially enlarged view of the GC-MS chart of phosphorus compound (2).
Figure 6D:
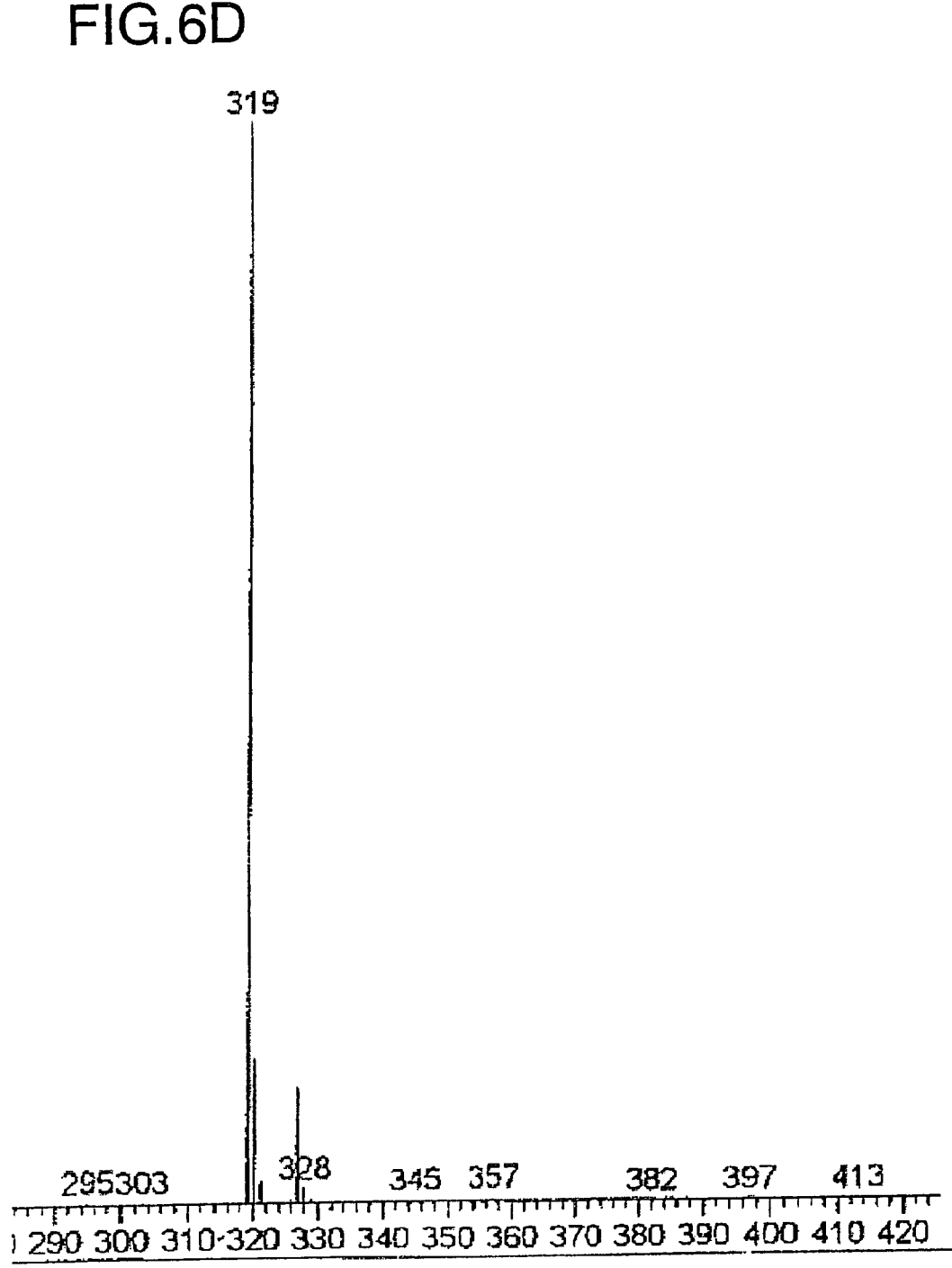
FIG. 6D shows a partially enlarged view of the GC-MS chart of phosphorus compound (2).

The obtained product exhibited the state of a pale yellow transparent liquid at room temperature. Table 2 shows the elemental analysis results and the quantization value of phosphorus measured using a UV spectroscope. The measured values substantially matched the theoretical values. Regarding FT-IR, the infrared absorption area was quantitated numerically as shown below. $^1$H-NMR, $^{13}$C-NMR, and GC-MS chart are respectively shown in FIGS. 4A through 4D, FIGS. 5A through 5C, and FIGS. 6A through 6D. From the above results, the obtained product was confirmed to be a compound represented by the following chemical formula.

TABLE 2

|  | Measured value (%) | Theoretical value (%) |
| --- | --- | --- |
| Carbon | 52.3 | 52.4 |
| Hydrogen | 5.2 | 5.3 |
| Phosphorus | 15.1 | 15.1 |

IR: 3072, 2976, 2900, 1594, 1491, 1376, 1293, 1219, 1190, 1165, 1085, 1053, 1011, 960, 838, 774, 691, and 618 cm$^{-1}$.

Compound 20:

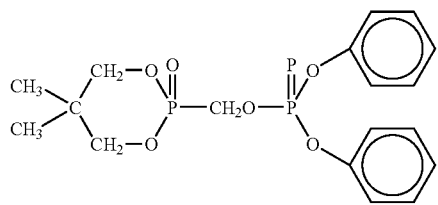

Synthesis Example 3

Synthesis of Phosphorus Compound (3)

(Synthesis of Intermediate 3)

A 2-liter four-neck flask equipped with a stirrer, a thermometer, a dripping device, a hydrochloric acid recovering device and a reflux tube was filled with 275.0 g (2 mol) of phosphorus trichloride and 400 g of n-butyl chloride. While the mixed solution was stirred, 444.0 g (6 mol) of n-butanol was added thereto from room temperature over 30 minutes. The temperature was finally raised to 70° C. After that, the pressure was gradually lowered to about 33 kPa at 60° C. The remaining by-products, hydrogen chloride gas and n-butyl chloride, were removed. The resultant substance was distilled at 90° C. and a low pressure of 0.67 kPa, thereby obtaining 343.8 g of dibutyl phosphite (intermediate 3). Intermediate 3 had a purity measured by GPC (gel permeation chromatography) of 100% by area. The yield was 88.6%. Intermediate 3 exhibited the state of a colorless transparent liquid at room temperature.

(Synthesis of Intermediate 4)

A fresh 2-liter four-neck flask equipped with a stirrer, a thermometer, a dripping device, and a reflux tube was filled with 31.9 g (1 mol) of 94% paraformaldehyde, 90 g of toluene, and 20.2 g (0.2 mol) of triethylamine. While the mixed solution was stirred, a mixed solution of 194.0 g (1 mol) of intermediate 3 and 90 g of toluene was added at 60° C. over 2 hours. After that, the substances were reacted at the same temperature (60° C.) for 1 hour, thereby obtaining a solution containing dibutyl (hydroxymethyl) phosphonate (intermediate 4) as a main component. A purity measured by GPC (gel permeation chromatography) excluding the solvent and triethylamine was 93.2% by area. The pure yield in the solution was 89.1%. Triethylamine used as a catalyst and toluene used as a solvent were not recovered since they were to be used for the next step.

In order to examine the physical properties of intermediate 4, a part of the solution containing intermediate 4 as a main component was sampled, and the solvent and triethylamine were removed in the same manner as described in the above section "Synthesis of intermediate 1". Intermediate 4 was found to exhibit the state of a color less transparent liquid.

The flask accommodating the post-reaction solution containing intermediate 4 was filled with 121.4 g (1.2 mol) of triethylamine and 1.85 g (0.015 mol) of 4-(dimethylamino) pyridine. While the mixed solution was stirred, a mixed solution of 164.2 g (0.89 mol) of material 1 and 450 g of toluene was added thereto at 20° C. over 2 hours. After that, the substances were reacted at the same temperature (20° C.) for 8 hours. The obtained post-reaction solution was neutralized at room temperature using an aqueous solution of hydrochloric acid in an amount corresponding to the excess amount of triethylamine. The resultant solution was kept still so as to be separated into different layers. Then, the organic layer was neutralized using an aqueous solution of sodium hydrogen carbonate. The organic layer was then washed with water twice. The obtained organic layer was dried by anhydrous magnesium sulfate. The solvent and water were removed by distillation, thereby obtaining 311.2 g of phosphorus compound (3). Phosphorus compound (3) had a purity measured by GPC (gel permeation chromatography) of 95.1% by area. The yield was 94.0%.

The overall yield with respect to phosphorus trichloride was:

(intermediate 3)88.6%×(intermediate 4)89.1%×(phosphorus compound 3)94.0%=74.2%.

Figure 7A:
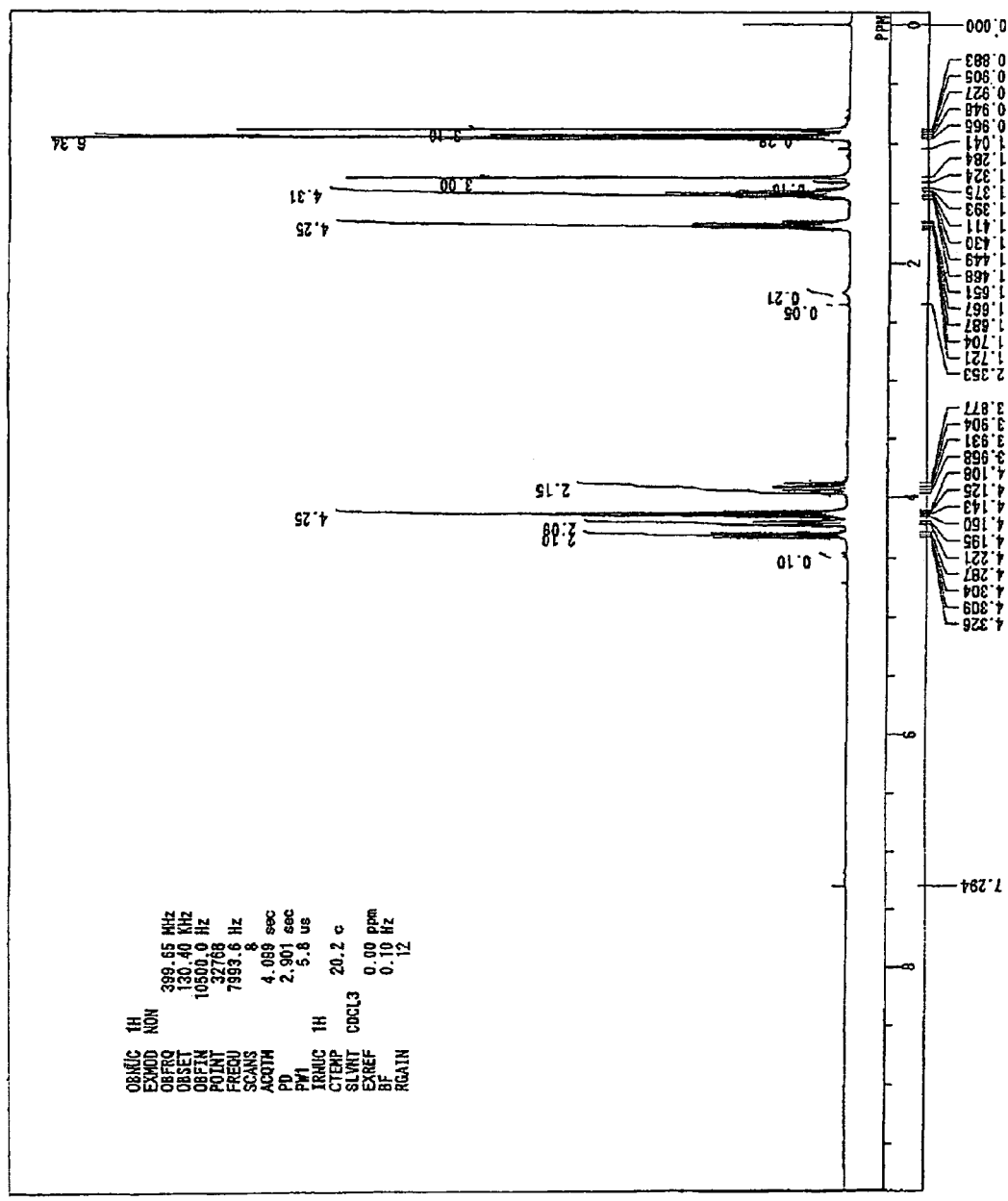
FIG. 7A shows a $^1$H-NMR chart of phosphorus compound (3).
Figure 7C:
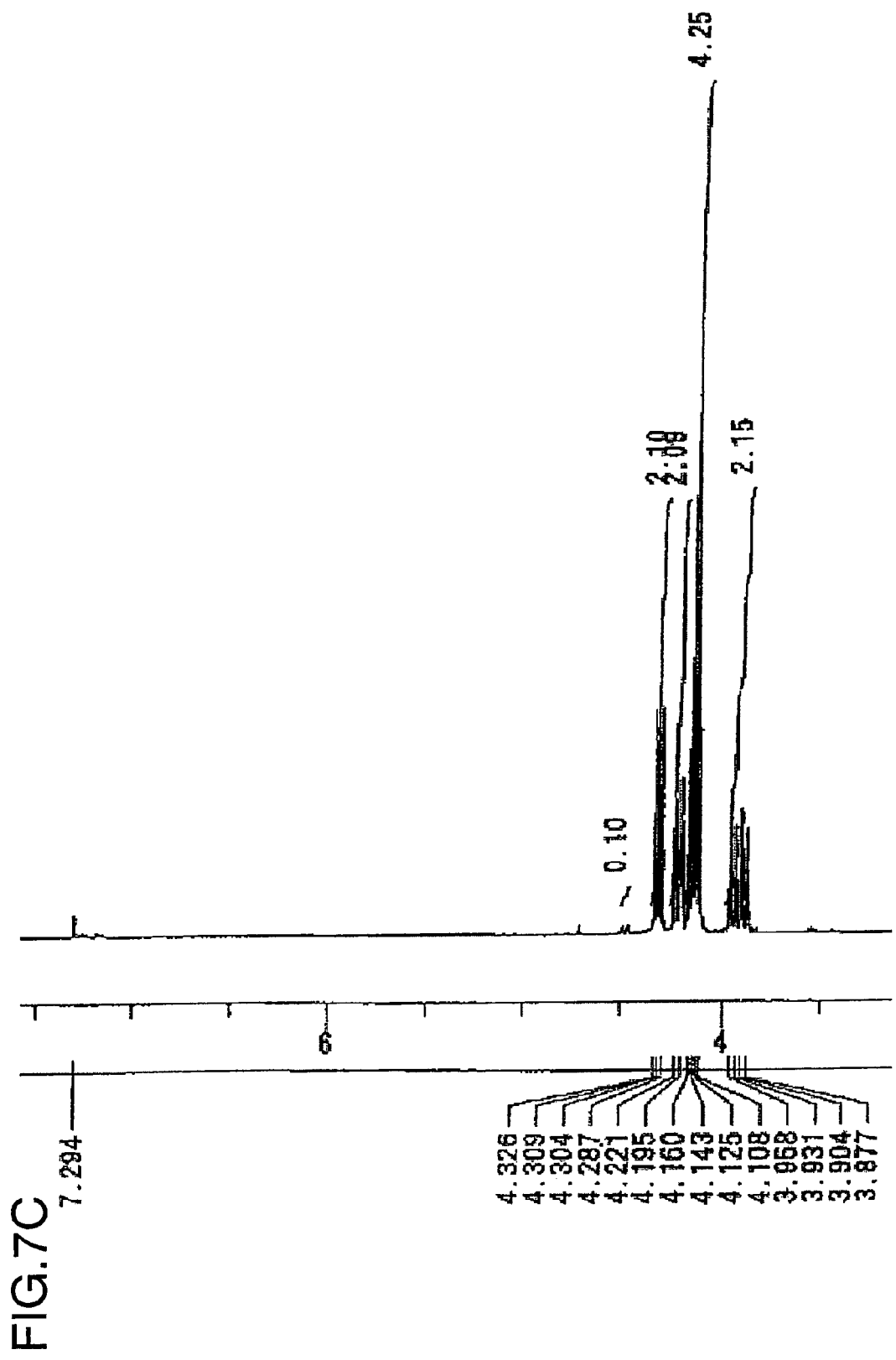
FIG. 7C shows a partially enlarged view of the $^1$H-NMR chart of phosphorus compound (3).
Figure 8A:
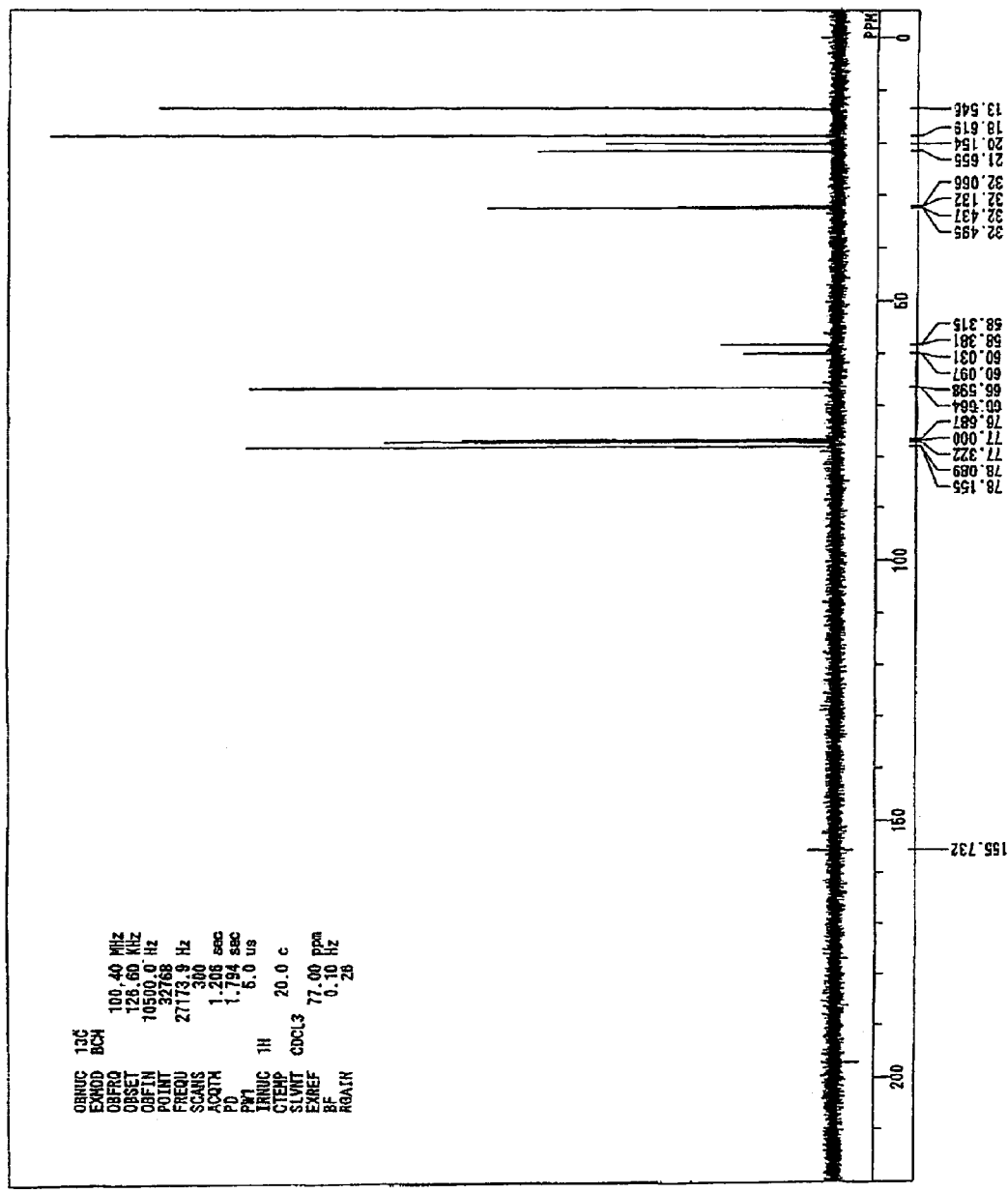
FIG. 8A shows a $^{13}$C-NMR chart of phosphorus compound (3).
Figure 8B:
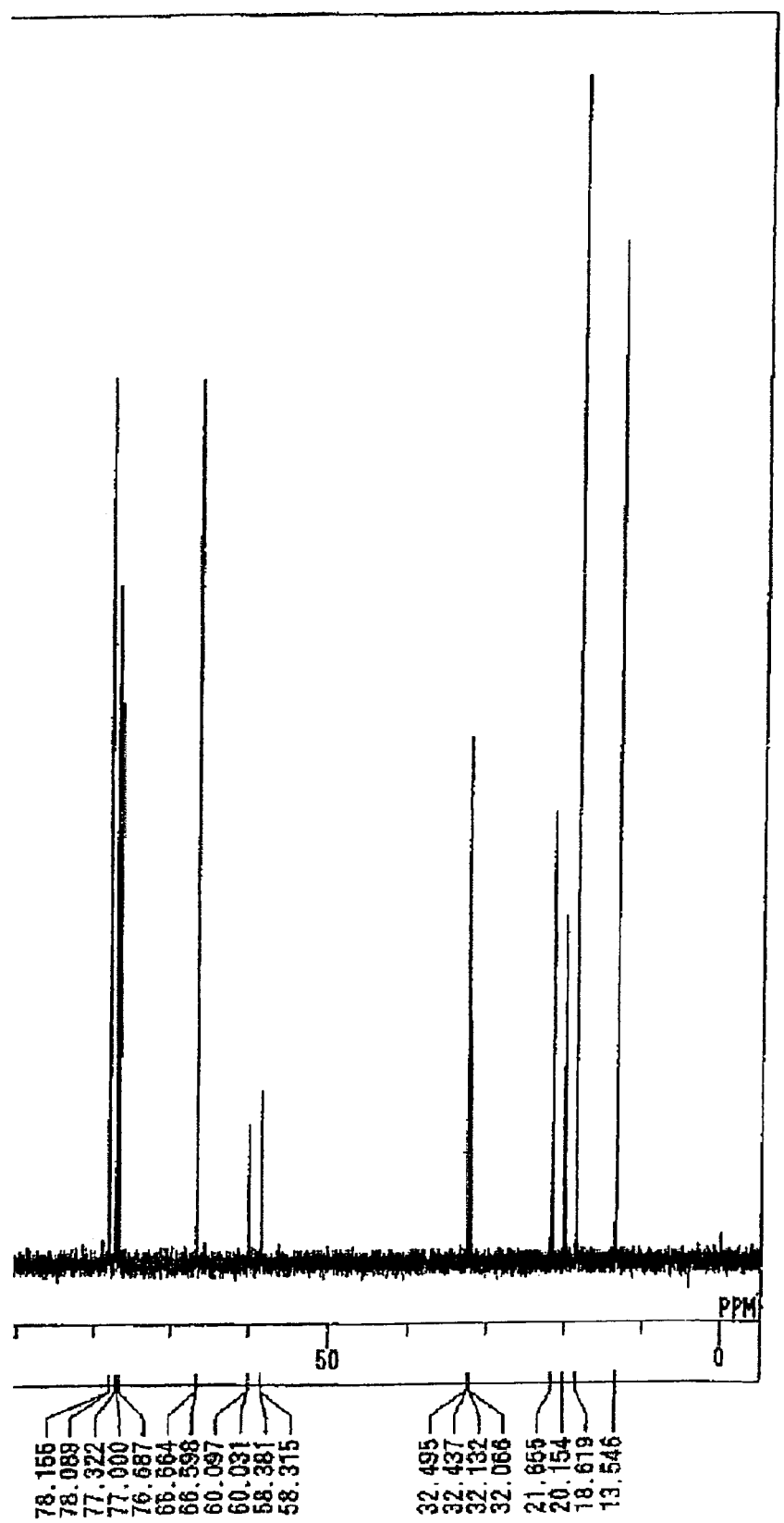
FIG. 8B shows a partially enlarged view of the $^{13}$C-NMR chart of phosphorus compound (3).
Figure 8C:
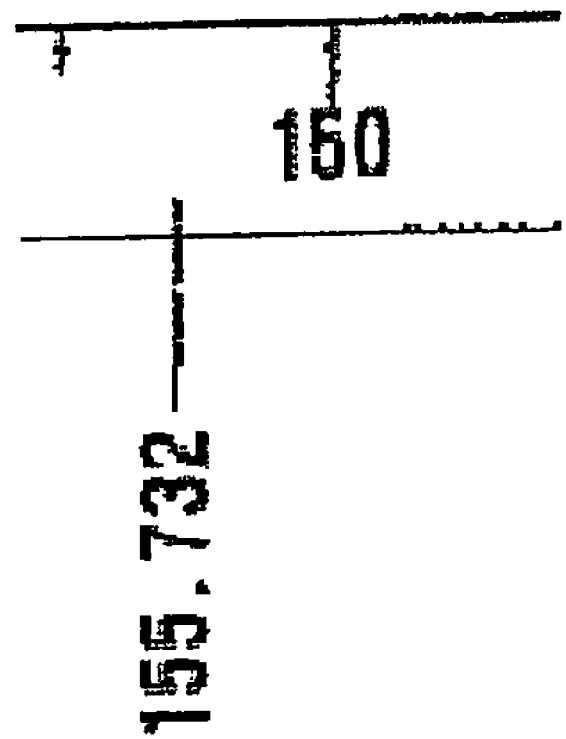
FIG. 8C shows a partially enlarged view of the $^{13}$C-NMR chart of phosphorus compound (3).
Figure 9A:
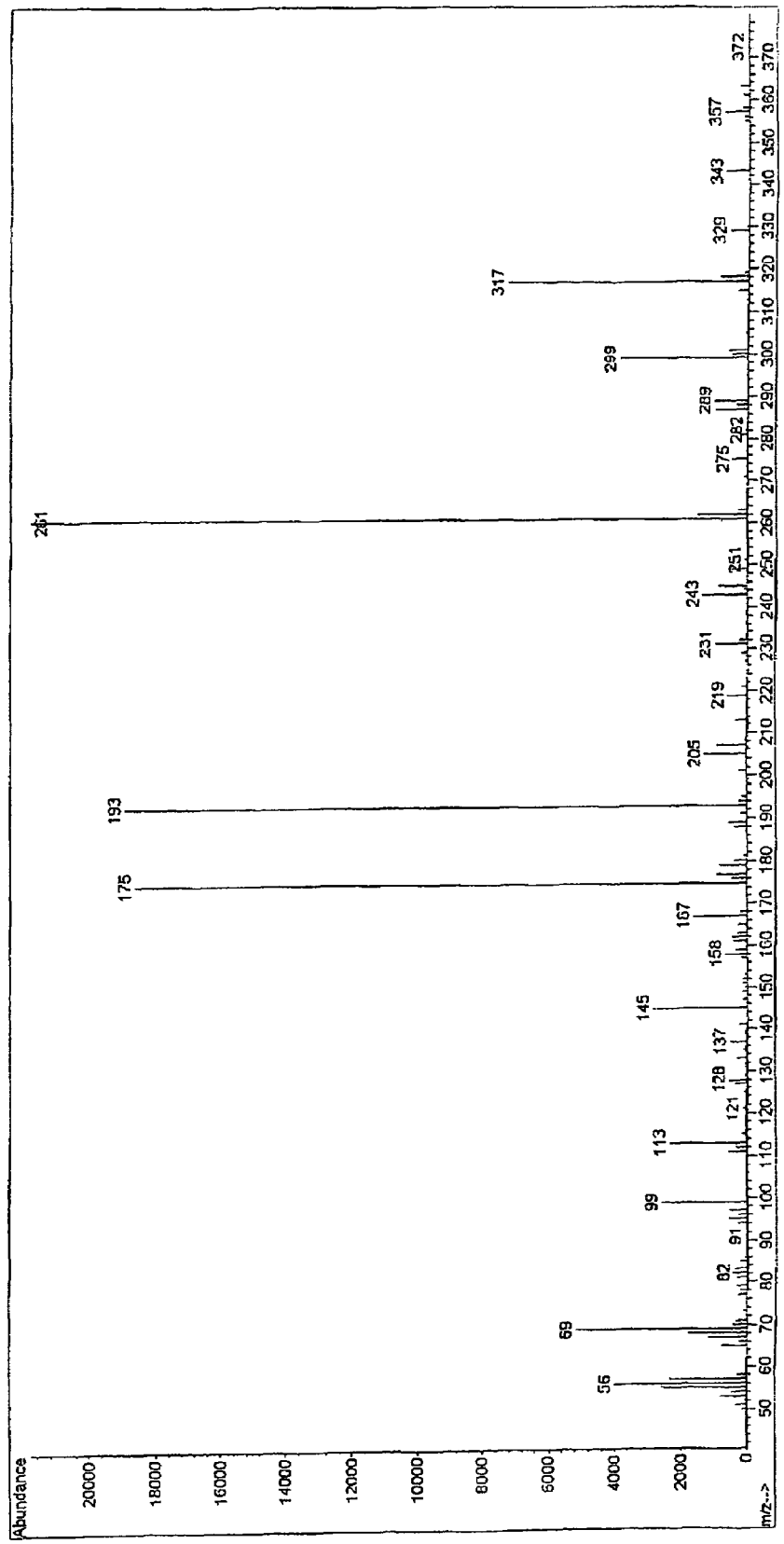
FIG. 9A shows a GC-MS chart of phosphorus compound (3).
Figure 9C:
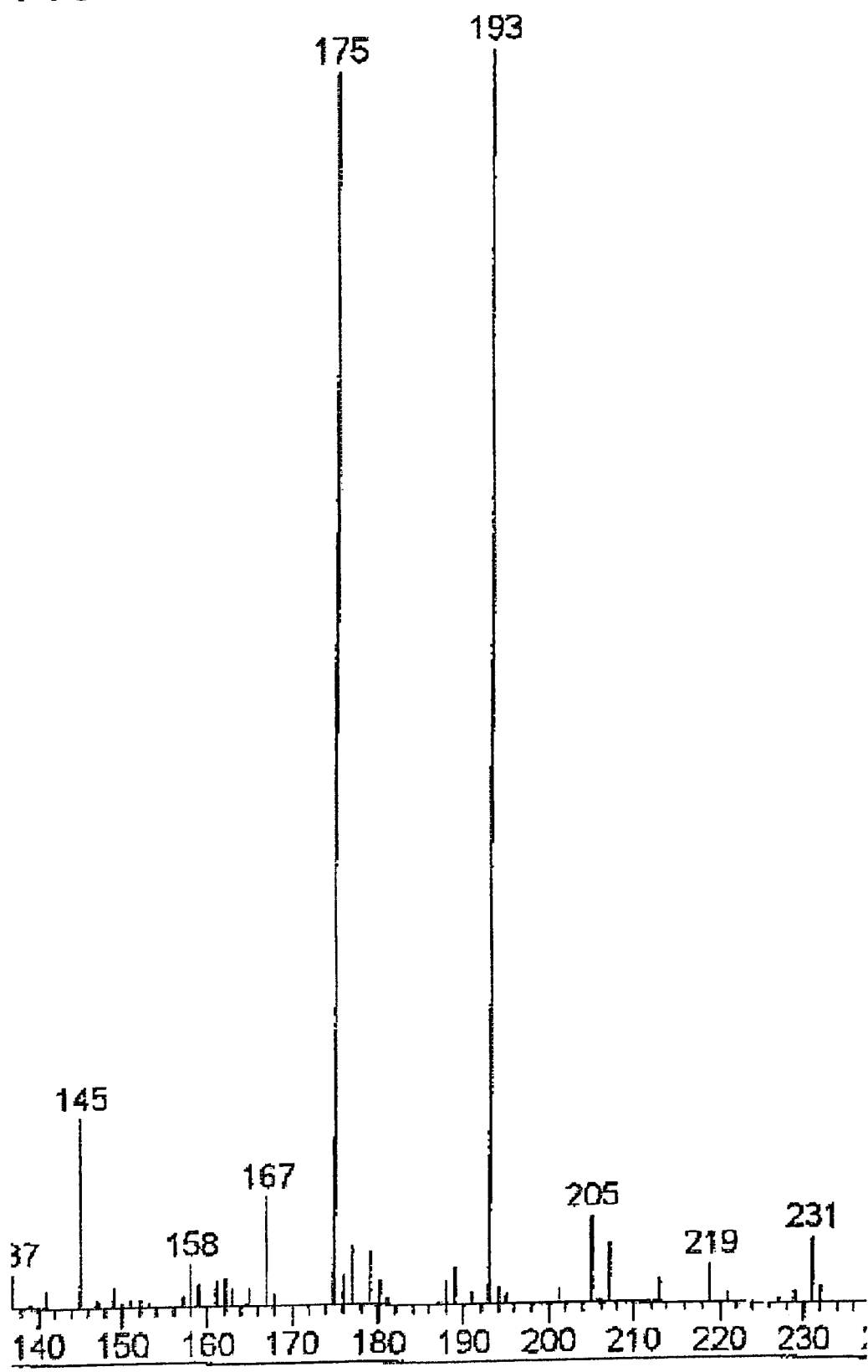
FIG. 9C shows a partially enlarged view of the GC-MS chart of phosphorus compound (3).
Figure 9D:
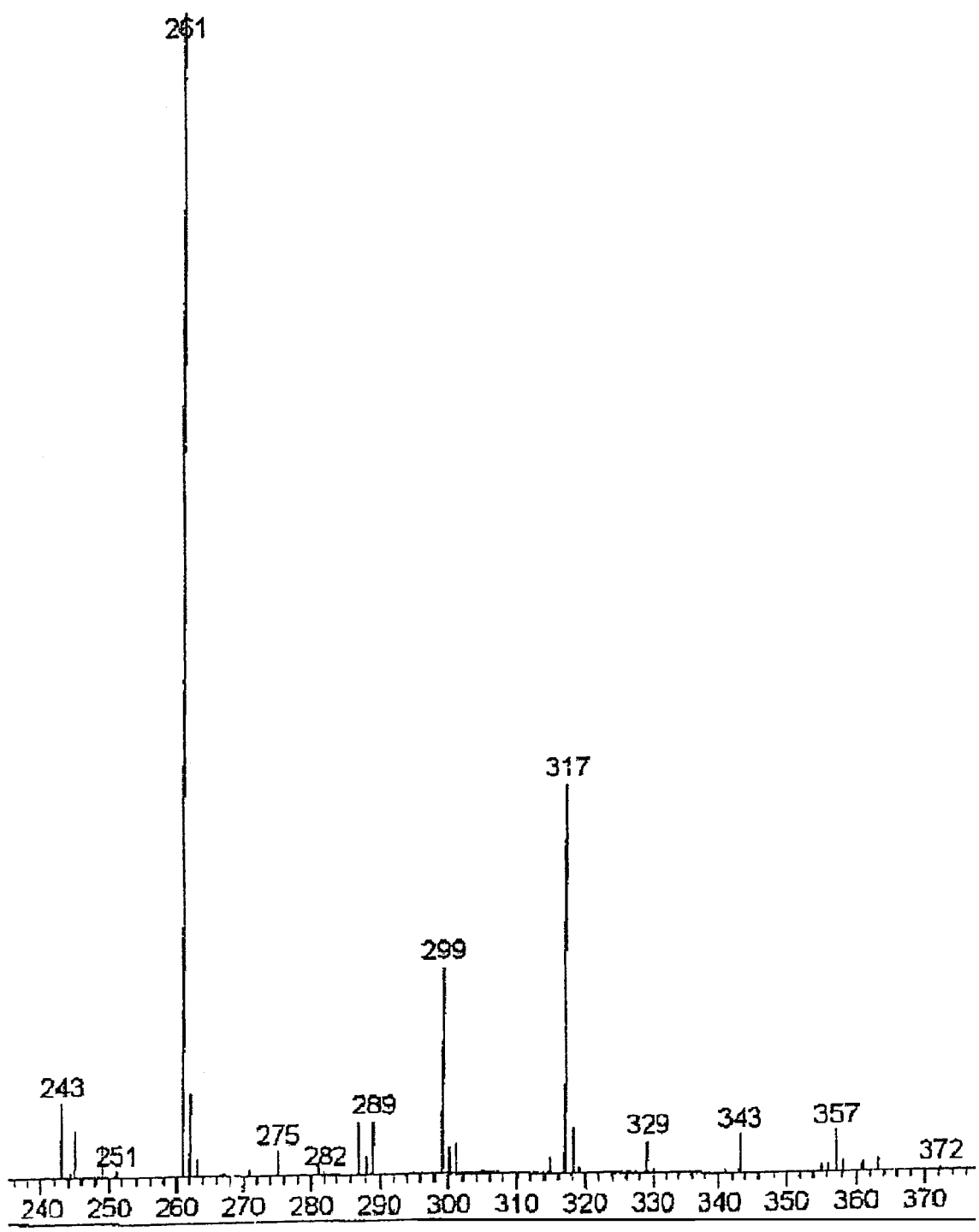
FIG. 9D shows a partially enlarged view of the GC-MS chart of phosphorus compound (3).

The obtained product exhibited the state of a colorless transparent liquid at room temperature. Table 3 shows the elemental analysis results and the quantization value of phosphorus measured using a UV spectroscope. The measured values substantially matched the theoretical values. Regarding FT-IR, the infrared absorption area was quantitated numerically as shown below. $^1$H-NMR, $^{13}$C-NMR, and GC-MS chart are respectively shown in FIGS. 7A through 7C, FIGS. 8A through 8C, and FIGS. 9A through 9D. From the above results, the obtained product was confirmed to be a compound represented by the following chemical formula.

TABLE 3

|  | Measured value (%) | Theoretical value (%) |
| --- | --- | --- |
| Carbon | 45.4 | 45.2 |
| Hydrogen | 8.2 | 8.1 |
| Phosphorus | 16.6 | 16.7 |

IR: 2976, 1475, 1379, 1306, 1264, 1056, 1011, 918, 858, and 627 cm$^{-1}$.

Compound 27:

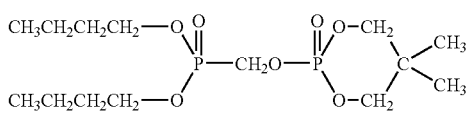

Compound 43:

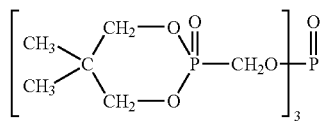

Synthesis Example 4

Synthesis of Phosphorus Compound (4)

A 2-liter four-neck flask equipped with a stirrer, a thermometer, a dripping device, a hydrochloric acid recovering device, and a reflux tube was filled with 302.4 g (1.68 mol) of intermediate 2 in synthesis example 1, 1 kg of 1,2-dichloroethane, 1.02 g (0.008 mol) of 4-(dimethylamino) pyridine, and 202.4 g (2.0 mol) of triethylamine. While the mixed solution was stirred, 86.0 g (0.56 mol) of phosphorus oxychloride was added thereto at room temperature over 60 minutes. After that, the substances were stirred and reacted at the same temperature for 8 hours, thereby completing the reaction. The obtained solution was neutralized at room temperature using an aqueous solution of hydrochloric acid in an amount corresponding to the excess amount of triethylamine. The resultant solution was kept still so as to be separated into different layers. Further, the organic layer was washed with water once. The obtained organic layer was dried by anhydrous magnesium sulfate. The solvent was removed from the filtrate by distillation, thereby obtaining 180.1 g of phosphorus compound (4). Phosphorus compound (4) had a purity measured by GPC (gel permeation chromatography) of 97.5% by area. The yield was 55.1%.

The overall yield with respect to phosphorus trichloride was:

(intermediate 1)80.4%×(intermediate 2)96.0%×(phosphorus compound 4)55.1%=42.5%.

Figure 10A:
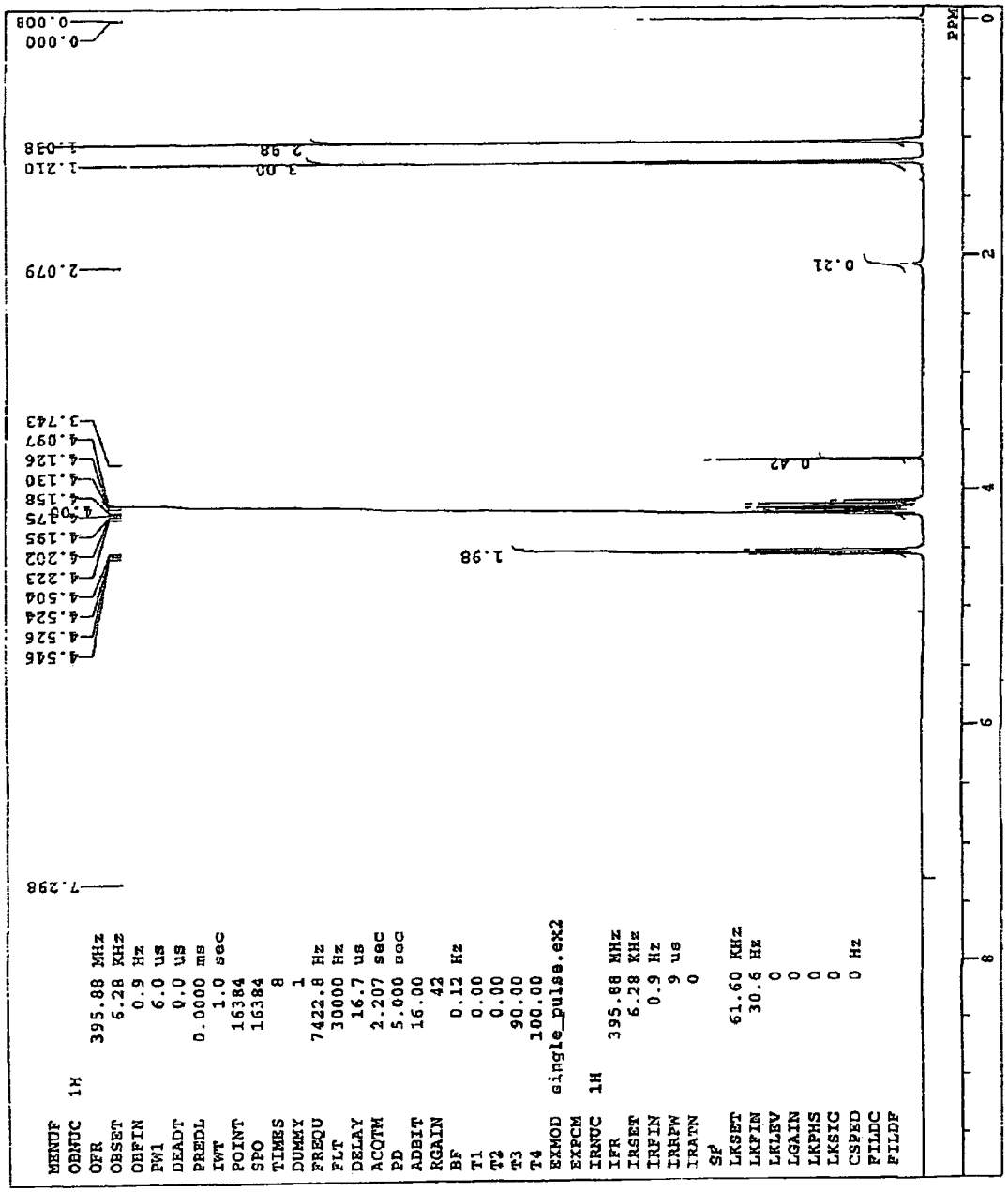
FIG. 10A shows a $^1$H-NMR chart of phosphorus compound (4).
Figure 10B:
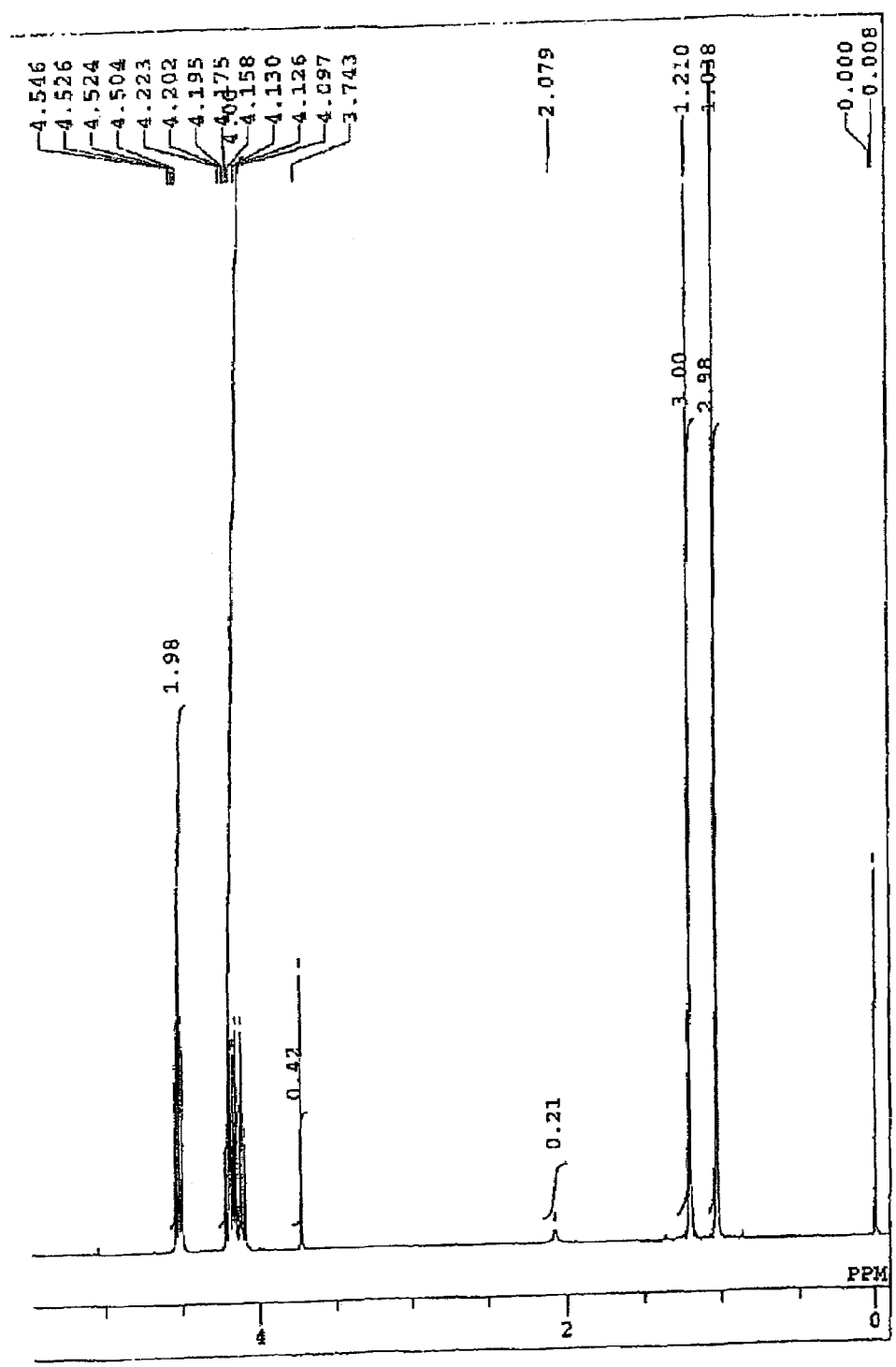
FIG. 10B shows a partially enlarged view of the $^1$H-NMR chart of phosphorus compound (4).
Figure 10C:
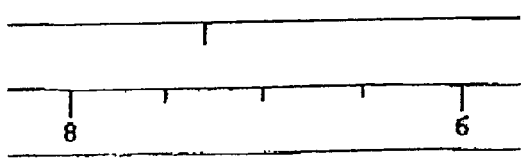
FIG. 10C shows a partially enlarged view of the $^1$H-NMR chart of phosphorus compound (4).
Figure 11A:
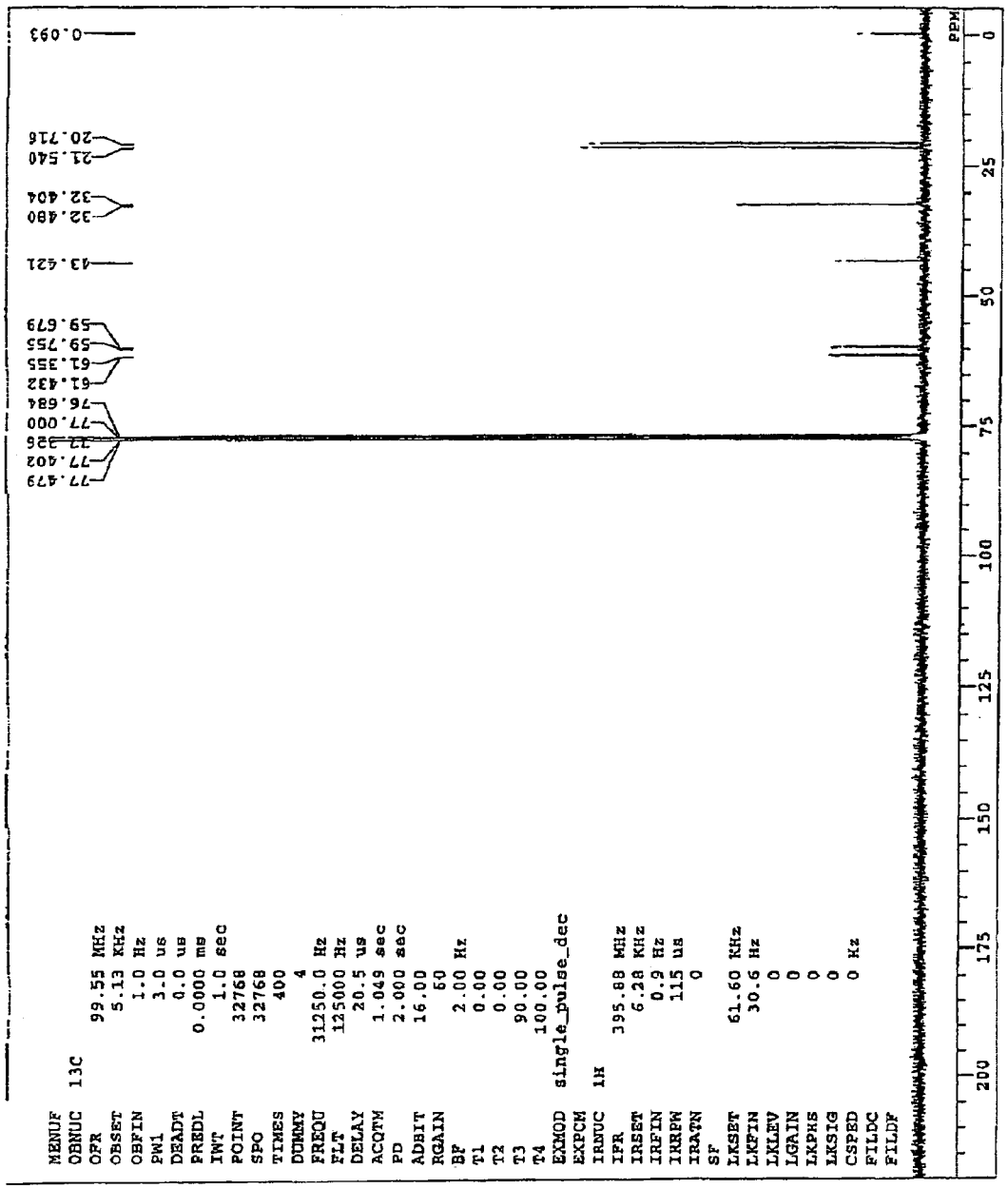
FIG. 11A shows a $^{13}$C-NMR chart of phosphorus compound (4).
Figure 11B:
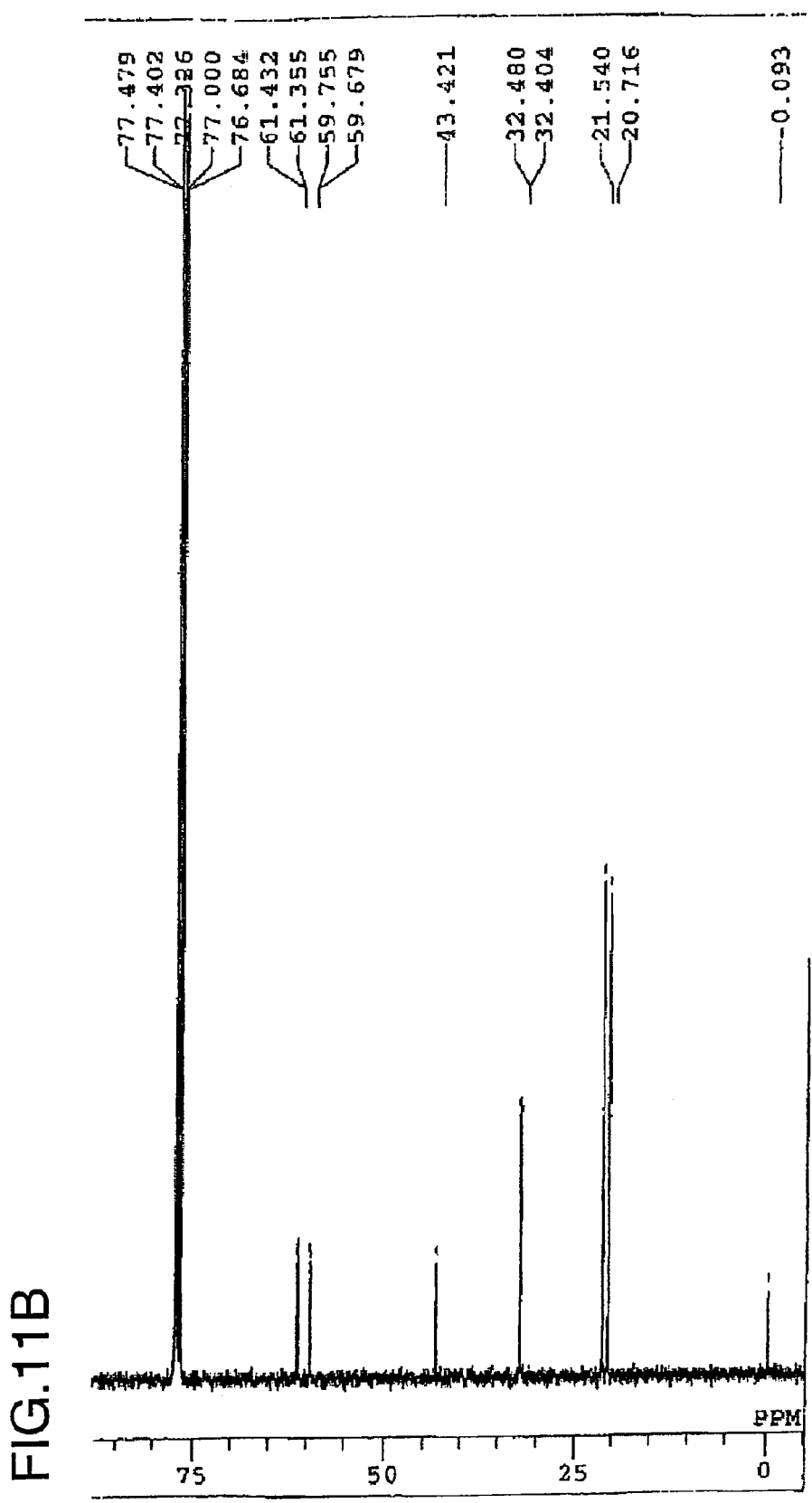
FIG. 11B shows a partially enlarged view of the $^{13}$C-NMR chart of phosphorus compound (4).
Figure 12A:
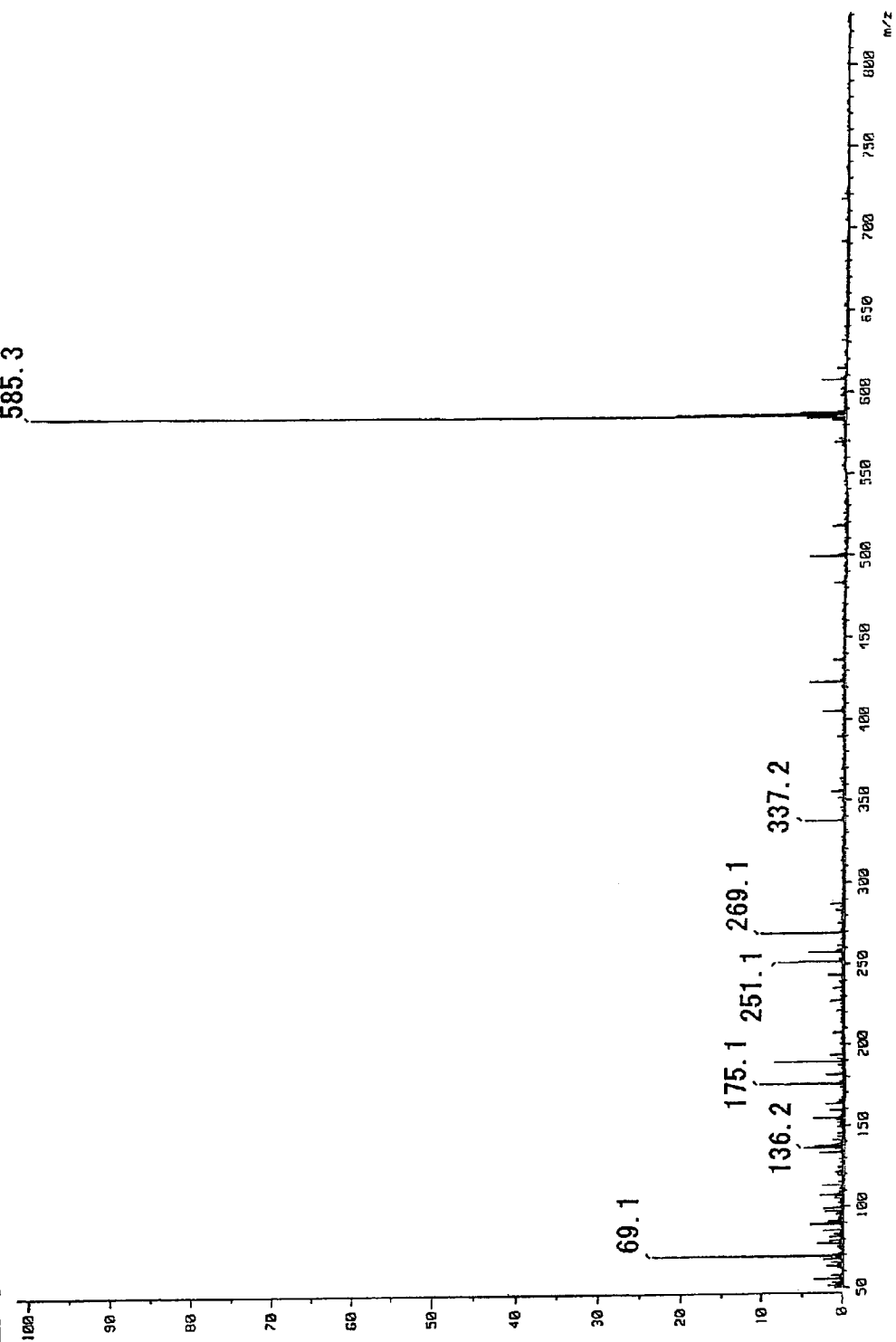
FIG. 12A shows a GC-MS chart of phosphorus compound (4).
Figure 12B:
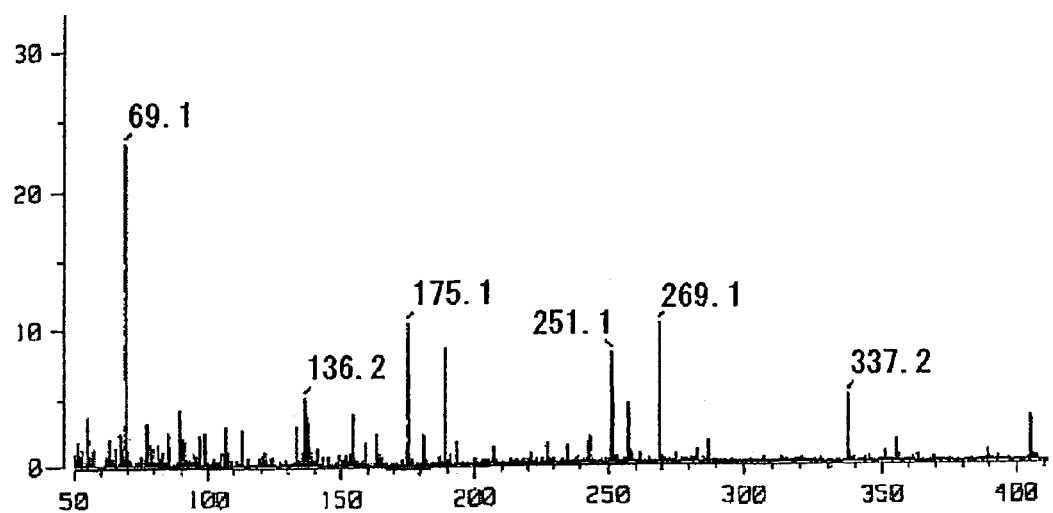
FIG. 12B shows a partially enlarged view of the GC-MS chart of phosphorus compound (4).
Figure 12C:
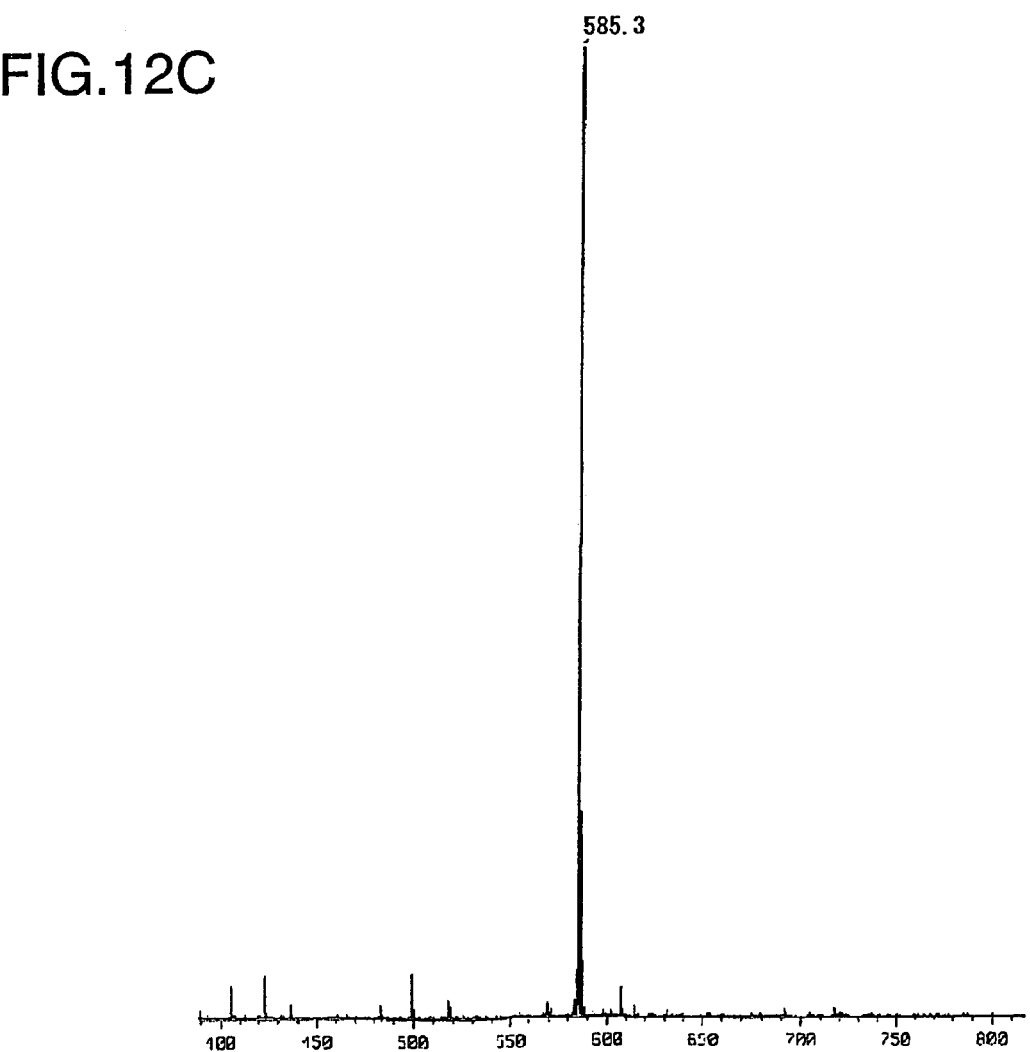
FIG. 12C shows a partially enlarged view of the GC-MS chart of phosphorus compound (4).

The obtained product had a melting point of 151.0° C. and exhibited the state of white crystals. Table 4 shows the elemental analysis results and the quantization value of phosphorus measured using a UV spectroscope. The measured values substantially matched the theoretical values. Regarding FT-IR, the infrared absorption area was quantitated numerically as shown below. $^1$H-NMR, $^{13}$C-NMR, and GC-MS chart are respectively shown in FIGS. 10A through 10C, FIGS. 11A and 11B, and FIGS. 12A through 12C. From the above results, the obtained product was confirmed to be a compound represented by the following chemical formula.

TABLE 4

|  | Measured value (%) | Theoretical value (%) |
| --- | --- | --- |
| Carbon | 36.5 | 37.0 |
| Hydrogen | 6.2 | 6.2 |
| Phosphorus | 21.0 | 21.2 |

IR(KBr): 2976, 2912, 1478; 1437, 1411, 1376, 1290, 1248, 1053, 1008, 979, 950, 925, 877, 864, 819, 614, and 477 cm$^{-1}$.

Synthesis Example 5

Synthesis was performed in substantially the same manner as in synthesis example 1 except that 1 mol of acetaldehyde was used instead of 1 mol of paraformaldehyde as a material of intermediate 2. As a result, a compound having a structure in which the linking group between a phosphorus atom and a phosphorus atom, (—CH$_2$—O—), of phosphorus compound (1) is substituted with (—CH(CH$_3$)—O—) was obtained at a good yield.

Synthesis Example 6

Synthesis was performed in substantially the same manner as in synthesis example 2 except that 1 mol of acetaldehyde was used instead of 1 mol of paraformaldehyde as a material of intermediate 2. As a result, a compound having a structure in which the linking group between a phosphorus atom and a phosphorus atom, (—CH$_2$—O—), of phosphorus compound (2) is substituted with (—CH(CH$_3$)—O—) was obtained at a good yield.

Synthesis Example 7

Synthesis was performed in substantially the same manner as in synthesis example 3 except that 1 mol of acetaldehyde was used instead of 1 mol of paraformaldehyde as a material of intermediate 4. As a result, a compound having a structure in which the linking group between a phosphorus atom and a phosphorus atom, (—CH$_2$—O—), of phosphorus compound (3) is substituted with (—CH(CH$_3$)—O—) was obtained at a good yield.

Synthesis Example 8

Synthesis was performed in substantially the same manner as in synthesis example 4 except that 1 mol of acetaldehyde was used instead of 1 mol of paraformaldehyde as a material of intermediate 2. As a result, a compound having a structure in which the linking group between a phosphorus atom and a phosphorus atom, (—CH$_2$—O—), of phosphorus compound (4) is substituted with (—CH(CH$_3$)—O—) was obtained at a good yield.

Synthesis Example 9

Synthesis of Phosphorus Compound (5)

(Synthesis of Intermediate 5)

A 2-liter four-neck flask equipped with a stirrer, a thermometer, a dripping device, a hydrochloric acid recovering device and a reflux tube was filled with 643.5 g (4.95 mol) of 2-ethylhexanol. While the liquid was stirred, 206.3 g (1.50 mol) of phosphorus trichloride was added thereto at 20° C. over 2 hours. 33.2 g of the generated by-product, hydrogen chloride, was recovered. After that, the temperature was gradually raised and the pressure was gradually lowered until the temperature was finally raised to 148° C. and the pressure was finally lowered to 2.0 kPa. The remaining by-products, hydrogen chloride gas and 2-ethyhexyl chloride, were removed. The resultant substance was distilled at 150° C. and a low pressure of 0.7 kPa, thereby obtaining 393.9 g of bis(2-ethylhexyl) phosphate (intermediate 5). Intermediate 5 had a purity measured by GPC (gel permeation chromatography) of 100% by area. The yield was 85.8%. Intermediate 5 exhibited the state of a colorless transparent liquid at room temperature.

(Synthesis of Intermediate 6)

A fresh 2-liter four-neck flask equipped with a stirrer, a thermometer, a dripping device, and a reflux tube was filled with 63.8 g (1.1 mol) of acetone, 90 g of 1,2-dichloroethane, and 5.4 g (0.1 mol) of sodium methoxide. While the mixed solution was stirred, 306.0 g (1.0 mol) of intermediate 5 was added thereto at 50° C. over 2 hours. After that, the substances were reacted at the same temperature (50° C.) for 1 hour, thereby obtaining a solution containing bis(2-ethylhexyl) dimethylhydroxymethyl phosphonate (intermediate 6) as a main component. A purity measured by GPC (gel permeation chromatography) excluding the solvent and sodium methoxide was 93.0% by area. The pure yield in the solution was 67.0%. 1,2-dichloroethane used as a solvent was not recovered since it was to be used in the next step. Sodium methoxide used as a catalyst was not recovered at this stage since it can be removed at the neutralization treatment in the next step.

In order to examine the physical properties of intermediate 6, a part of the solution containing intermediate 6 as a main component was sampled, and the solvent and the catalyst were removed in the same manner as described in the above section "Synthesis of intermediate 1". Intermediate 6 was found to exhibit the state of a colorless transparent liquid at room temperature.

(Synthesis of Phosphorus Compound (5))

The flask accommodating the post-reaction solution containing intermediate 6 was filled with 80.8 g (0.8 mol) of triethylamine, 4.1 g (0.034 mol) of 4-(dimethylamino) pyridine, and 420 g of 1,2-dichloroethane. While the mixed solution was stirred, a mixed solution of 123.6 g (0.67 mol) of material 1 and 450 g of 1,2-dichloroethane was added thereto at 20° C. over 2 hours. After that, the substances were reacted at the same temperature (20° C.) for 8 hours. The obtained post-reaction solution was neutralized at room temperature using an aqueous solution of hydrochloric acid in an amount corresponding to the excess amount of triethylamine and the amount of sodium methoxide used for synthesizing intermediate 6. The resultant solution was kept still so as to be separated into different layers. Then, the organic layer was neutralized using an aqueous solution of sodium hydrogen carbonate. The organic layer was then washed with water twice. The obtained organic layer was dried by anhydrous magnesium sulfate. The solvent and water were removed by distillation, thereby obtaining 212.9 g of phosphorus compound (5). Phosphorus compound (5) had a purity measured by GPC (gel permeation chromatography) of 82.0% by area. The yield was 62.1%.

The overall yield with respect to phosphorus trichloride was:

(intermediate 5)85.8%×(intermediate 6)67.0%×(phosphorus compound 5)62.1%=35.7%.

Figure 13B:
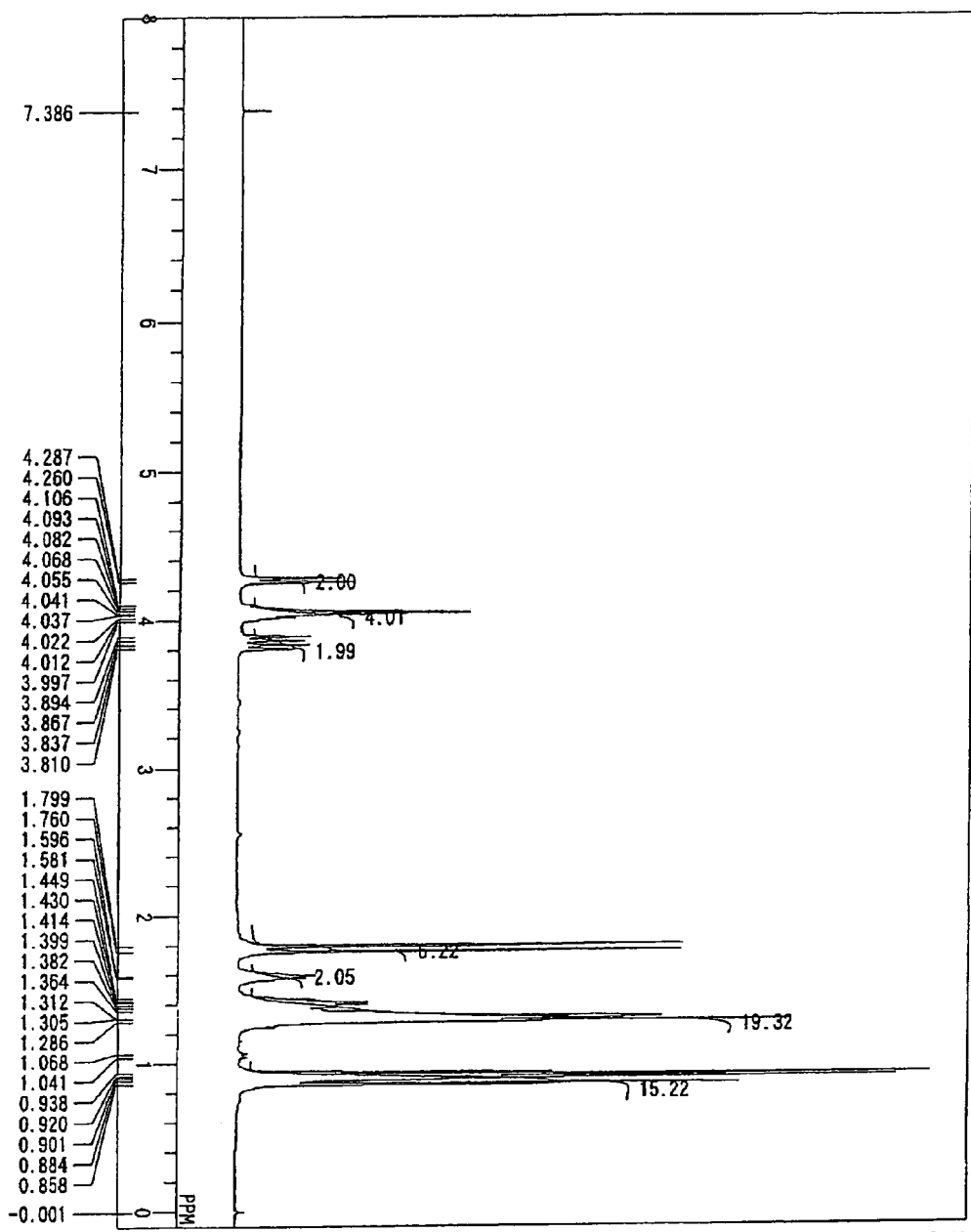
FIG. 13B shows a $^1$H-NMR chart of phosphorus compound (5).
Figure 13C:
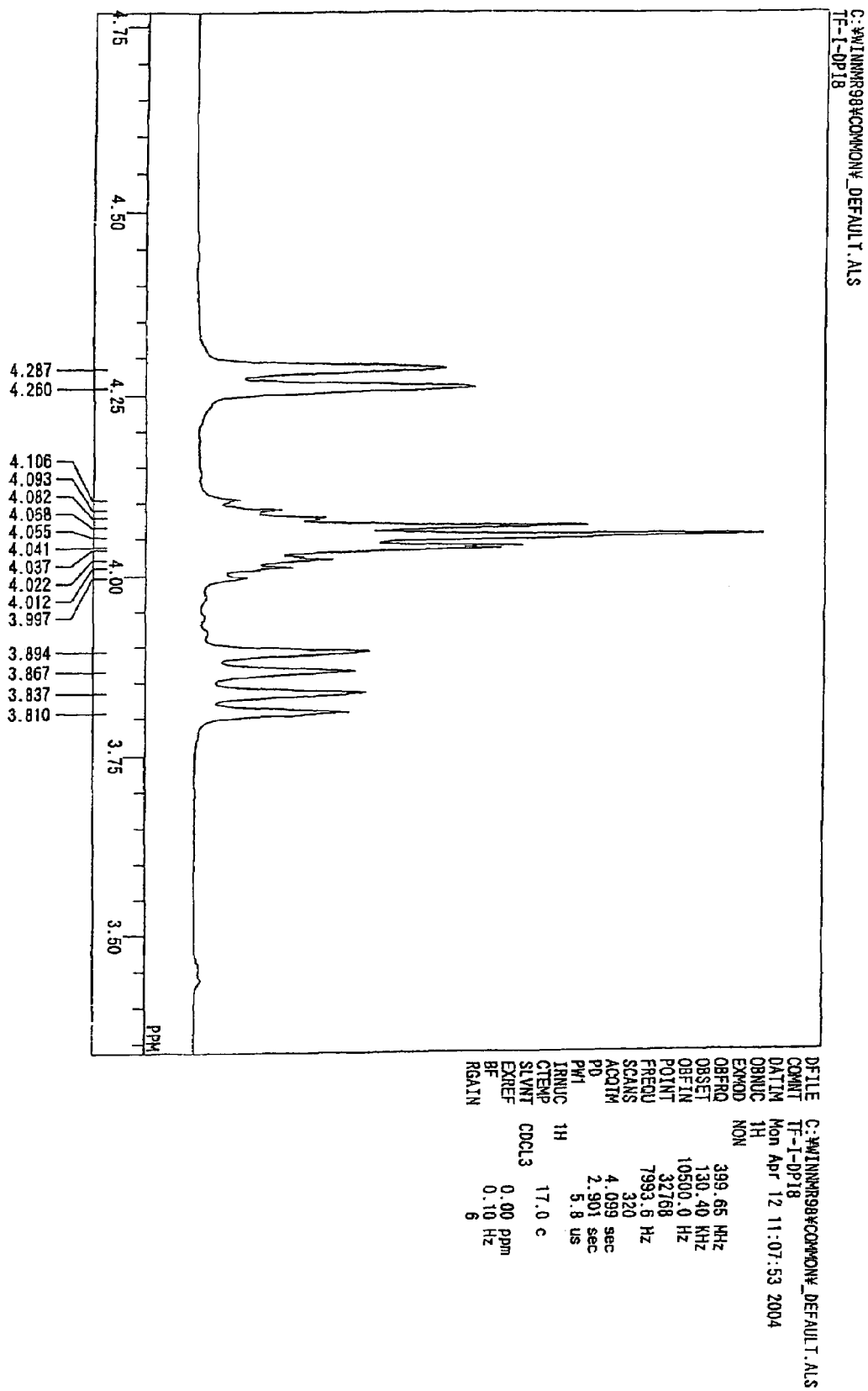
FIG. 13C shows a partially enlarged view of the $^1$H-NMR chart of phosphorus compound (5).
Figure 13D:
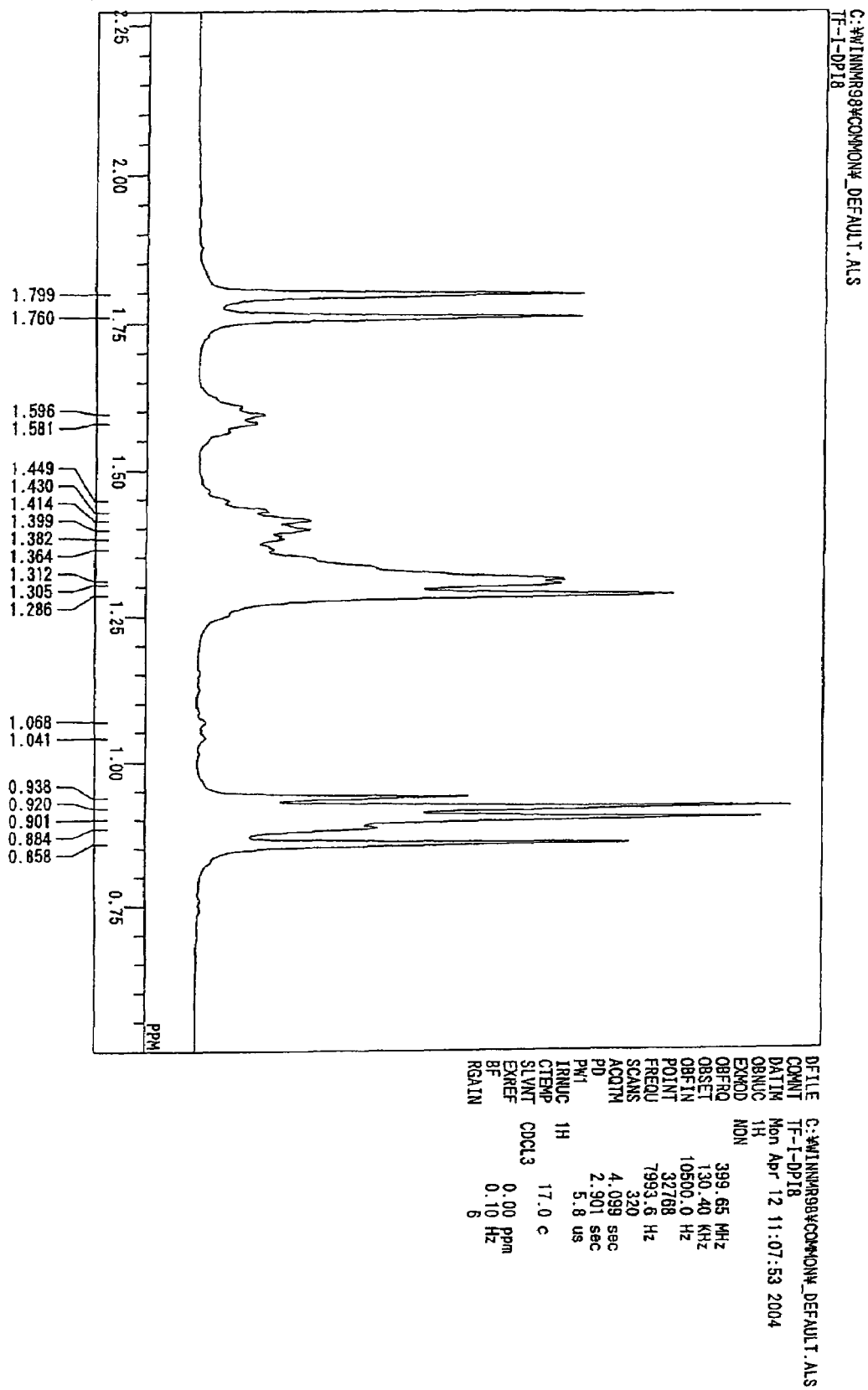
FIG. 13D shows a partially enlarged view of the $^1$H-NMR chart of phosphorus compound (5).
Figure 14B:
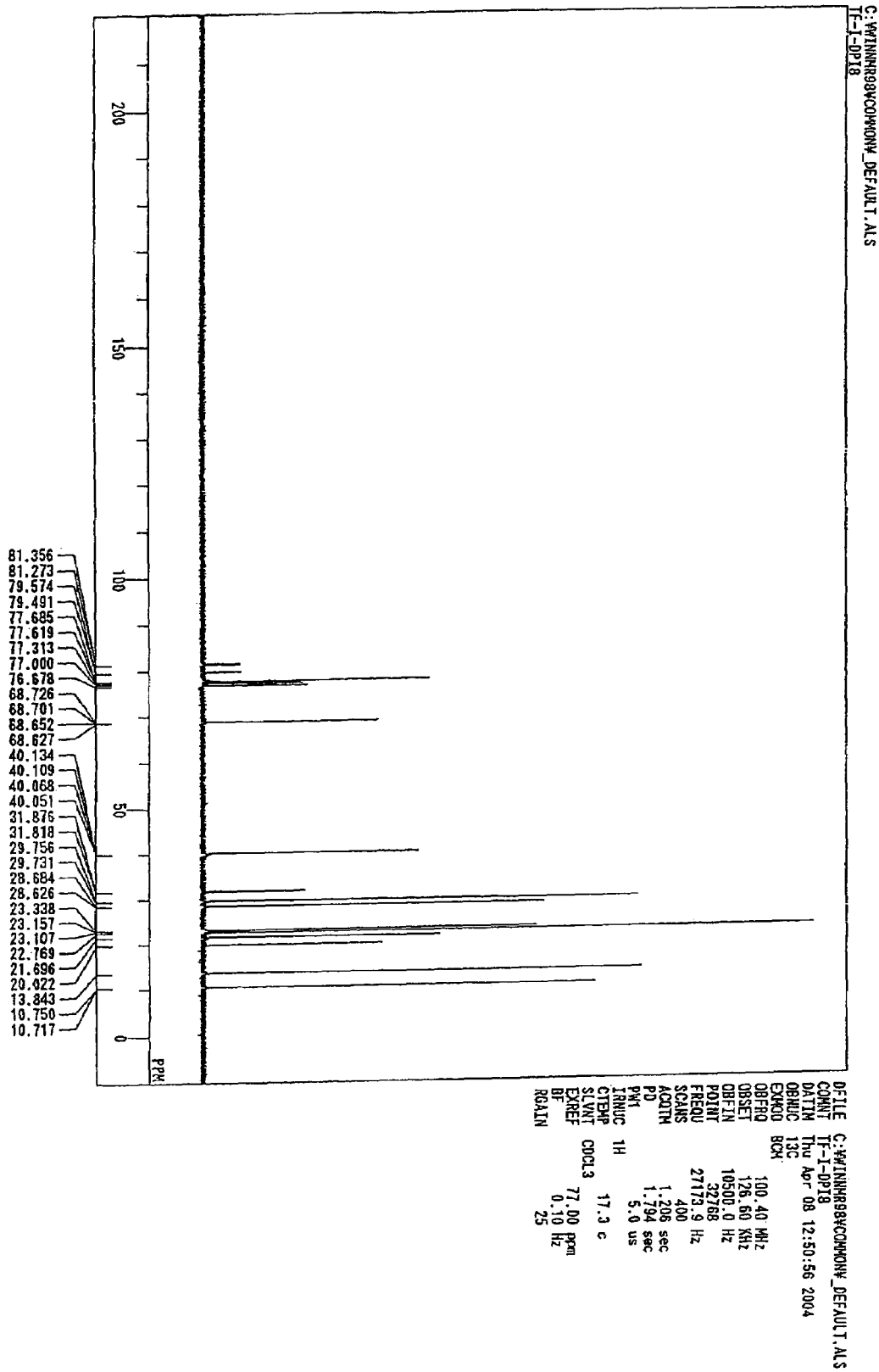
FIG. 14B shows a $^{13}$C-NMR chart of phosphorus compound (5).
Figure 14C:
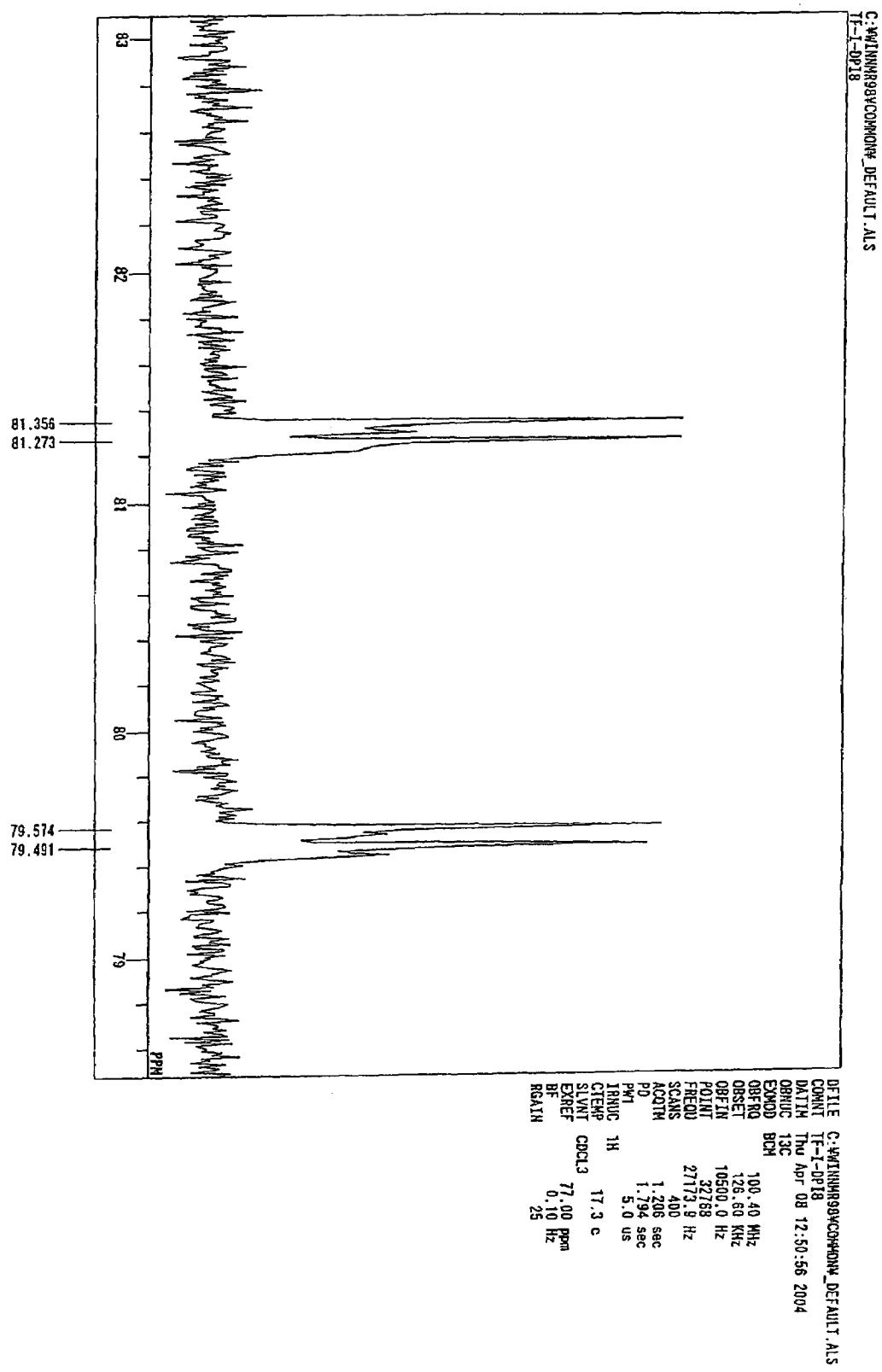
FIG. 14C shows a partially enlarged view of the $^{13}$C-NMR chart of phosphorus compound (5).
Figure 14D:
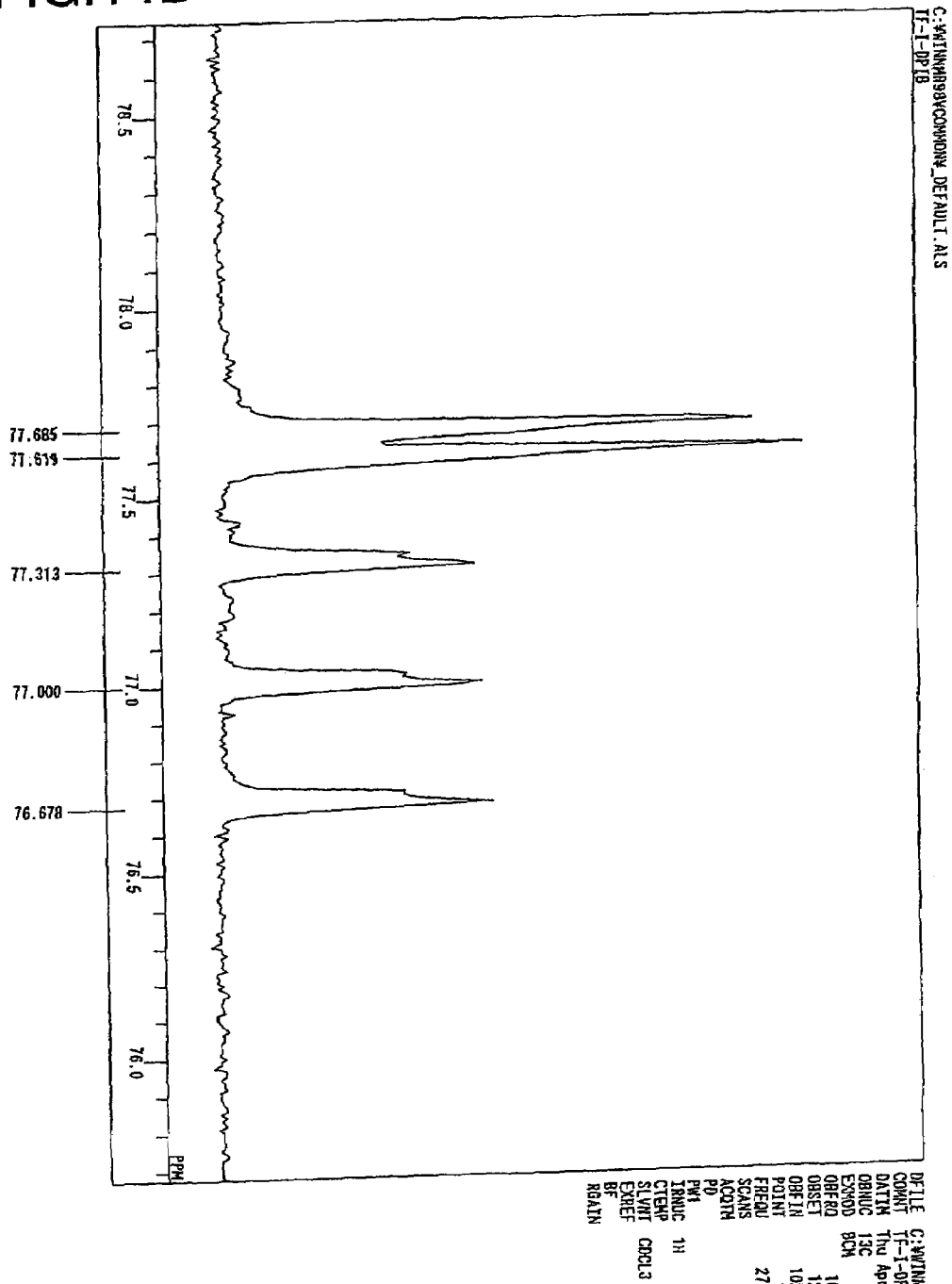
FIG. 14D shows a partially enlarged view of the $^{13}$C-NMR chart of phosphorus compound (5).
Figure 14E:
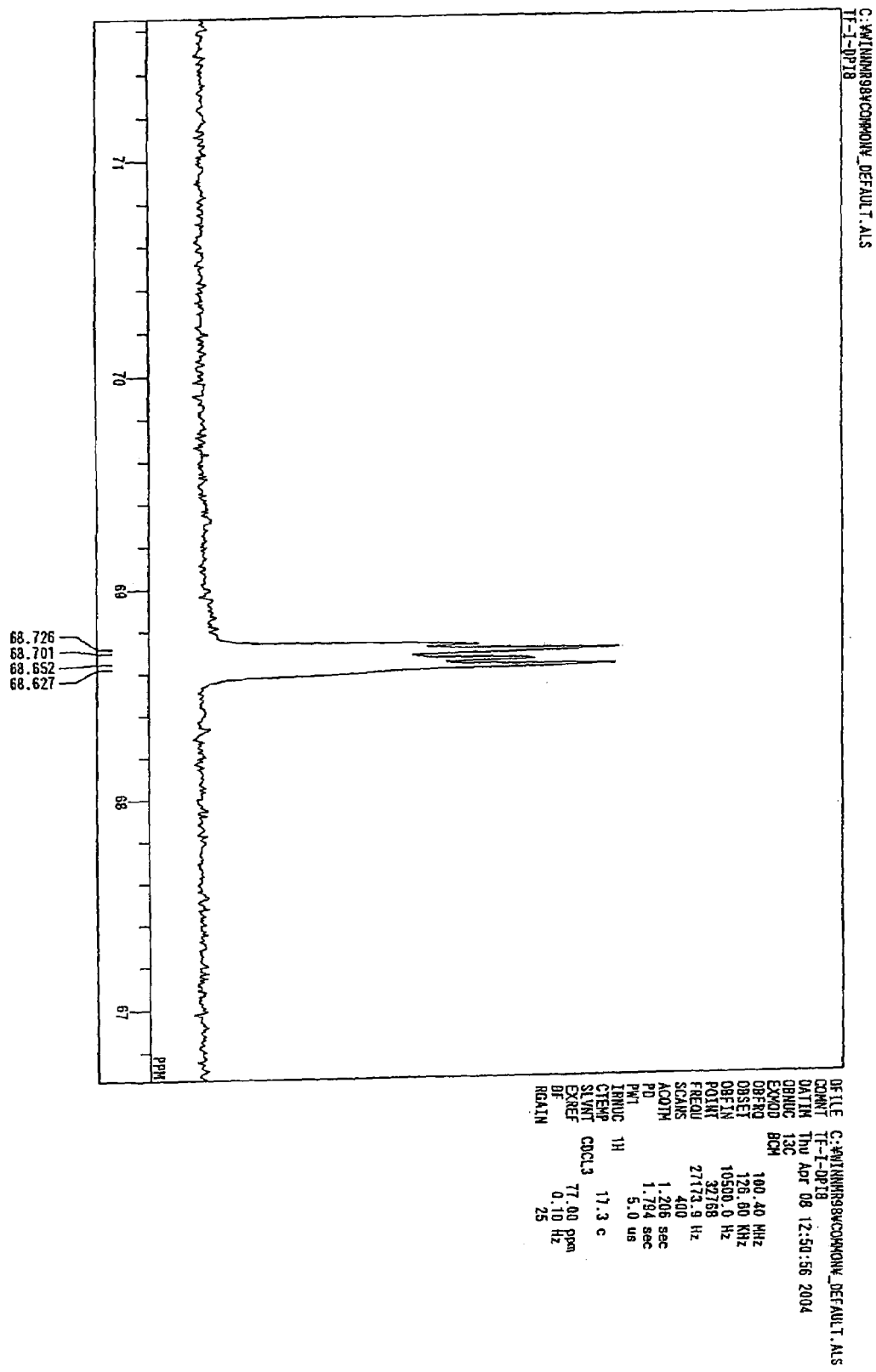
FIG. 14E shows a partially enlarged view of the $^{13}$C-NMR chart of phosphorus compound (5).
Figure 14F:
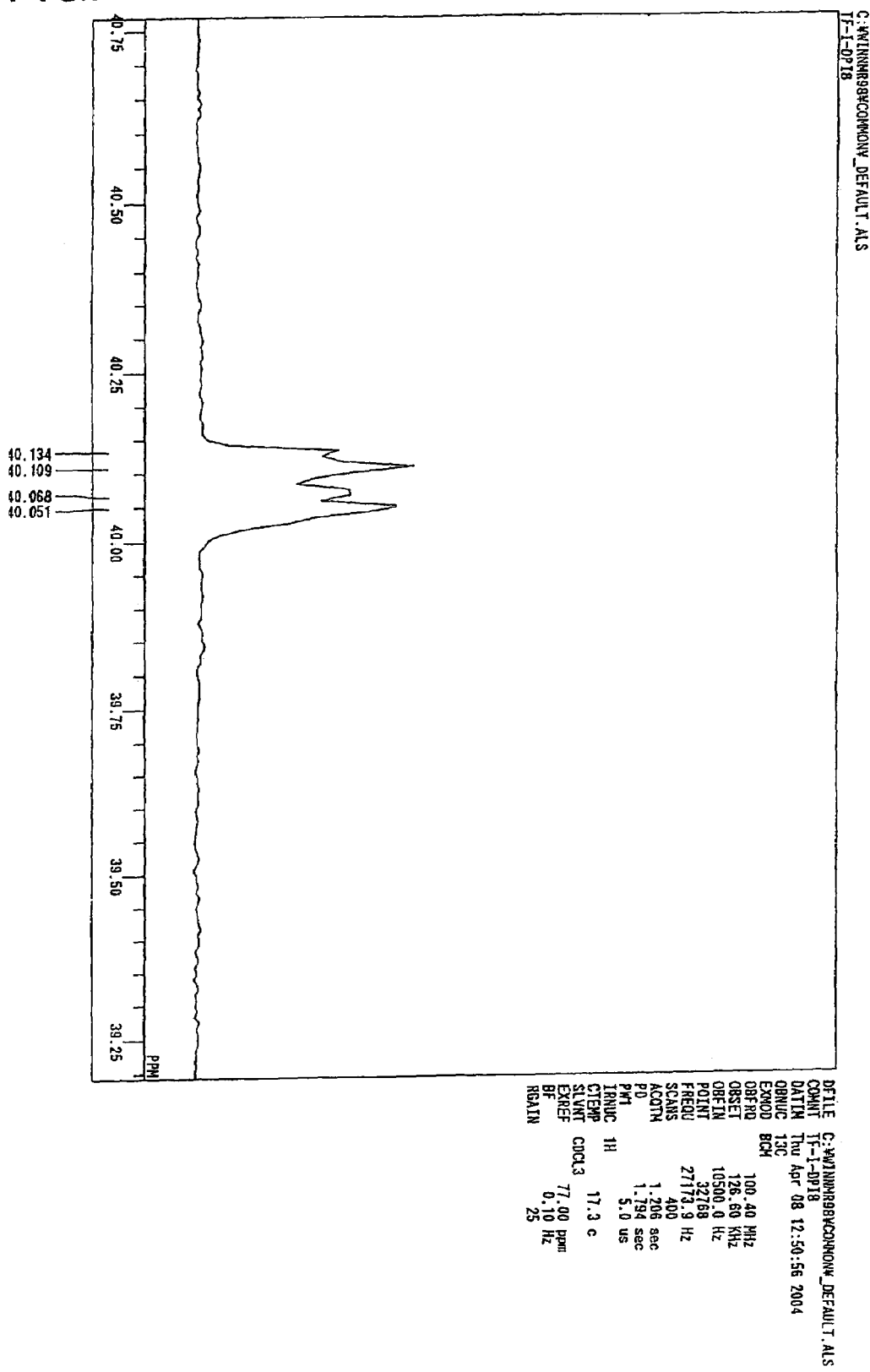
FIG. 14F shows a partially enlarged view of the $^{13}$C-NMR chart of phosphorus compound (5).
Figure 14G:
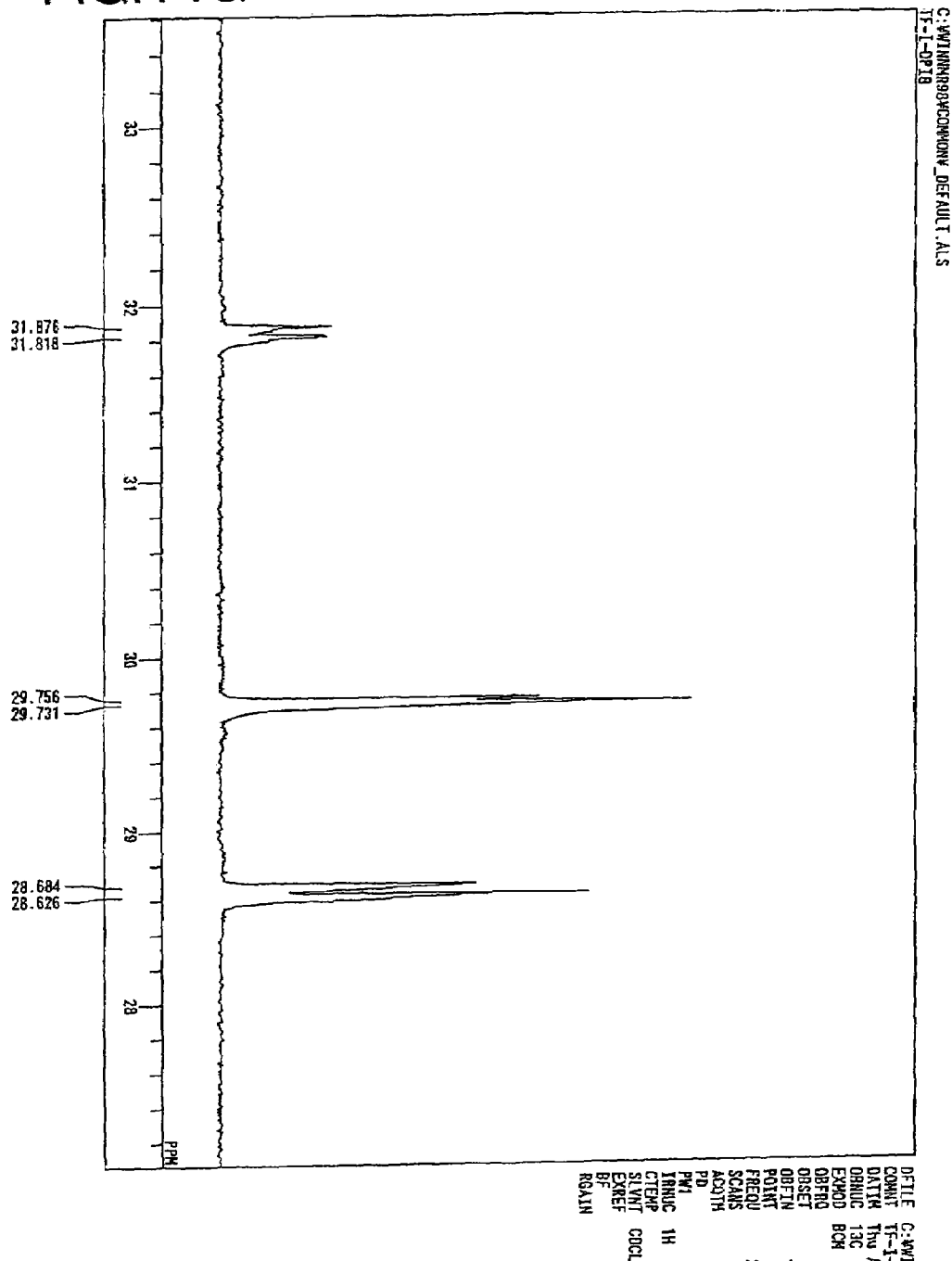
FIG. 14G shows a partially enlarged view of the $^{13}$C-NMR chart of phosphorus compound (5).
Figure 14H:
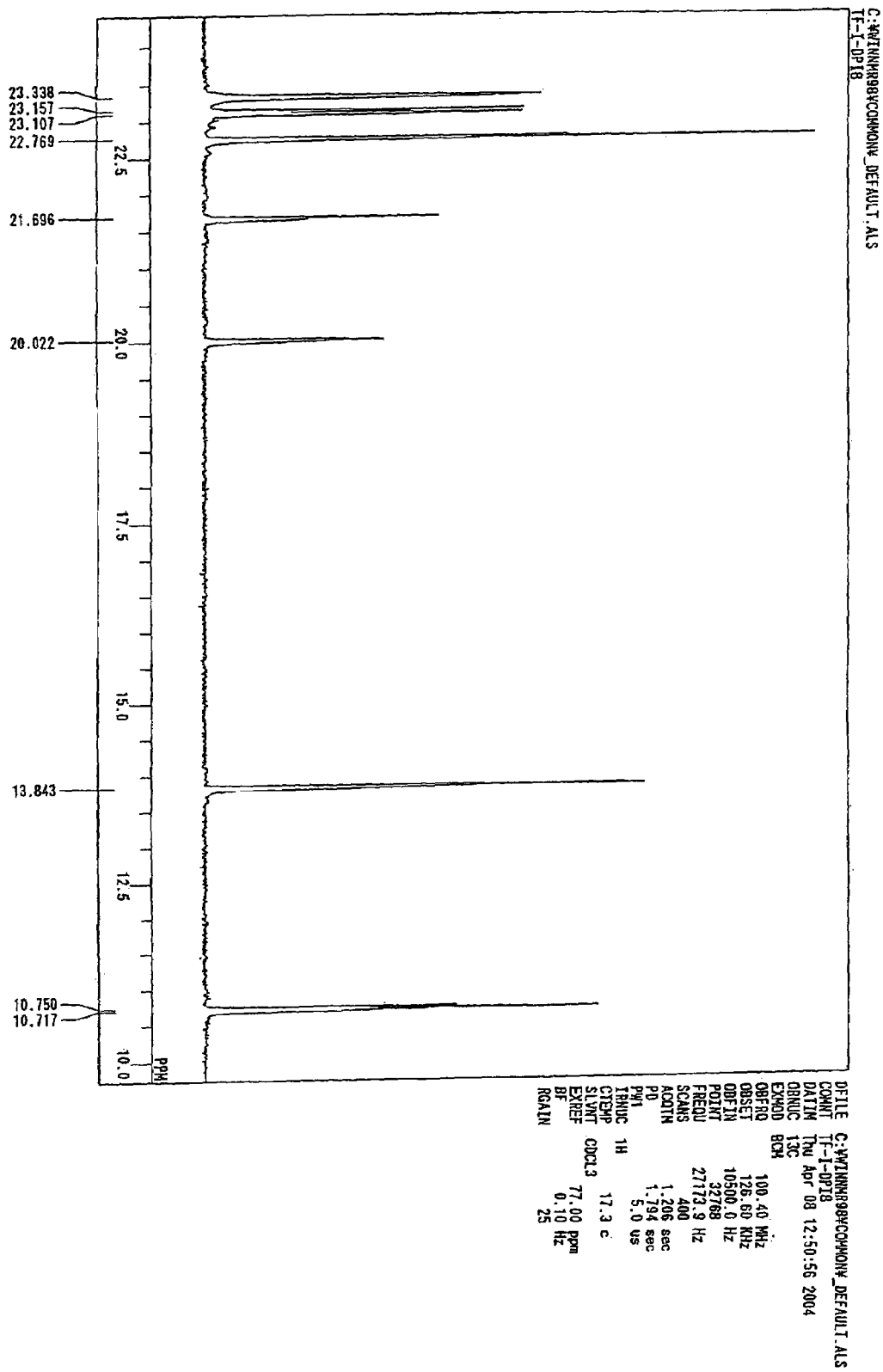
FIG. 14H shows a partially enlarged view of the $^{13}$C-NMR chart of phosphorus compound (5).
Figure 15:
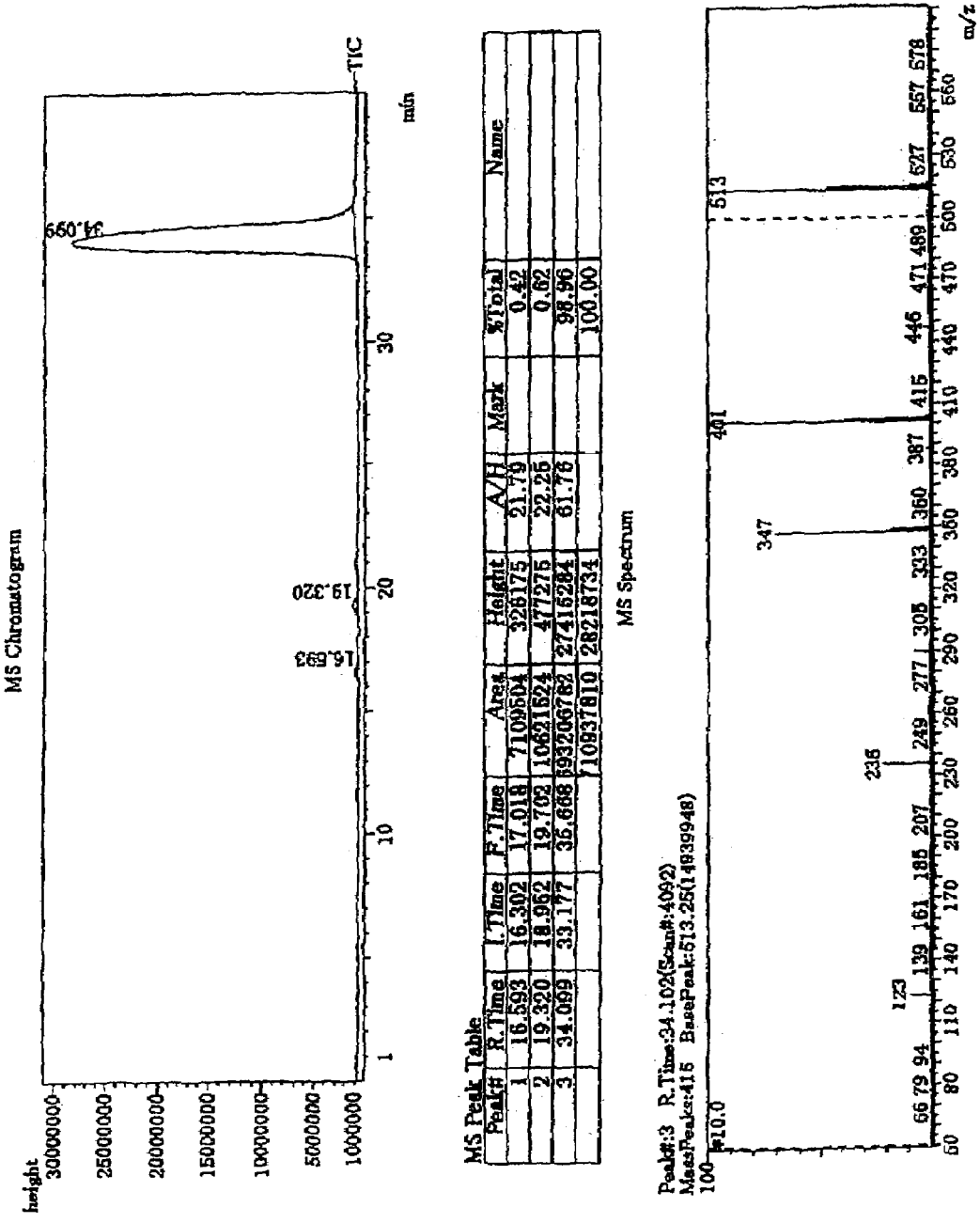
FIG. 15 shows LC-MS measurement results of phosphorus compound (5).

The obtained product exhibited the state of a colorless transparent liquid at room temperature. Table 5 shows the elemental analysis results and the quantization value of phosphorus measured using a UV spectroscope. The measured values substantially matched the theoretical values. Regarding FT-IR, the infrared absorption area was quantitated Numerically as shown below. $^1$H-NMR, $^{13}$C-NMR, and LC-MS chart are respectively shown in FIGS. 13A through 13D, FIGS. 14A through 14H, and FIG. 15. From the above results, the obtained product was confirmed to be a compound represented by the following chemical formula.

TABLE 5

|  | Measured value (%) | Theoretical value (%) |
|---|---|---|
| Carbon | 56.2 | 56.3 |
| Hydrogen | 9.8 | 9.8 |
| Phosphorus | 12.1 | 12.1 |

IR: 2960, 1466, 1376, 1309, 1264, 1216, 1152, 1069, 1014, 996, 918, 851, 816, 733, 624 cm$^{-1}$.

Compound 40:

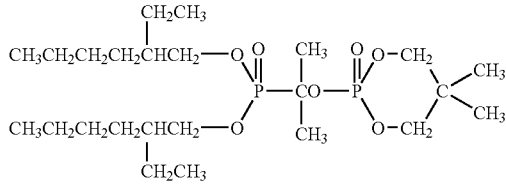

Synthesis Example 10

Synthesis was performed in substantially the same manner as in synthesis example 9 except that 1.1 mol of methylisobutylketone (MIBK) was used instead of 1.1 mol of acetone as a material of intermediate 6. As a result, a compound having a structure in which the linking group between a phosphorus atom and a phosphorus atom, (—C(CH$_3$)$_2$—O—), of phosphorus compound (5) is substituted with (—C(CH$_3$)(CH$_2$CH(CH$_3$)$_2$)—O—) was obtained.

Synthesis Example 11

Synthesis was performed in substantially the same manner as in synthesis example 9 except that intermediate 3 was used instead of intermediate 5. As a result, a corresponding compound was obtained at a good yield.

Synthesis Example 12

Synthesis was performed in substantially the same manner as in synthesis example 9 except that intermediate 3 was used instead of intermediate 5 and that 1.1 mol of cyclohexanone was used instead of 1.1 mol of acetone for synthesizing intermediate 6. As a result, a corresponding compound was obtained at a good yield.

Test Examples and Comparative Test Examples

Phosphorus compounds used for test examples and comparative test examples, and test methods will be described below.

(Flame Retardation Test on Polyester Fibers)

Polyester fiber fabrics (specific gravity: 250 g/m$^2$) of 100% polyethylene terephthalate were immersed in a 7.5% by weight of methanol solution having a phosphorus compound dissolved or dispersed therein for about 10 minutes, and squeezed by a mangle such that the pickup would be 70 to 80%. Then, the fabrics were dried at 110° C., and cured at 180° C. for several minutes. After that, the fabrics were washed and dried. These fabrics were used in a flame retardation test and a washing durability test. As the phosphorus compound, the phosphorus compounds obtained in synthesis examples 1 through 3 were used. Table 6 shows the results.

(Flame Retarding Property)

The flame retarding property was evaluated by the method described in JIS L 1091 A-1 (micro-burner method). The washing durability was evaluated by the method of washing described in JIS L 1091 (flame retarding property test method for fiber products).

TABLE 6

| | Flame retarding property (cm²) (Method A: combustion area) | |
| --- | --- | --- |
| Phosphorus compound | Washed 0 times | Washed 5 times |
| Phosphorus compound (1) | 4 | 4 |
| Phosphorus compound (2) | 3 | 3 |
| Phosphorus compound (3) | 5 | 5 |

When an organic phosphorus compound according to the present invention was used as a flame retarding agent for a polyester fiber, a sufficient level of flame retarding property was provided.

A flame retarding agent for polyester according to the present invention will be described more specifically below by way of synthesis examples, "polyester examples", and "polyester comparative examples", but the present invention is not limited by these examples.

Phosphorus compounds obtained by the synthesis examples, and components thereof used in the polyester examples and polyester comparative examples will be described below.

(a) Phosphorus compound (flame retarding agent) components (Hereinafter, for the sake of simplicity, flame retarding agents 1, 2, . . . for polyester will be referred to as "polyester flame retarding agents 1, 2, . . . .")

Polyester flame retarding agent 1: the following compound

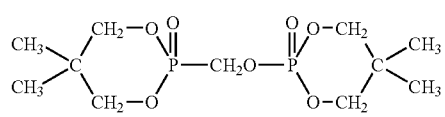

Polyester flame retarding agent 2: the following compound

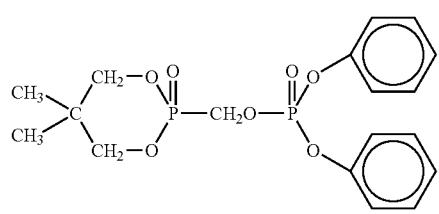

Polyester flame retarding agent 3: the following compound

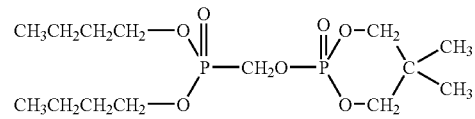

Polyester flame retarding agent 4: the following compound

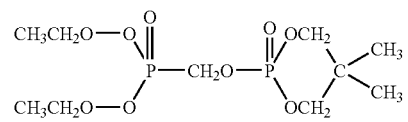

Polyester flame retarding agent 5: the following compound

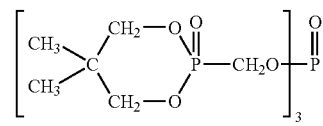

Polyester flame retarding agent 6: synthesis product obtained in conformity with EXAMPLE 10 described in U.S. Pat. No. 4,697,030

Polyester flame retarding agent 7: 1,2,5,6,9,10-hexabromocyclododecane (HBCD)

Polyester flame retarding agent 8: the following compound

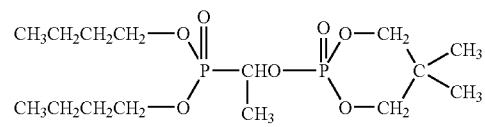

(b) Polyester Fiber

Polyester fiber fabrics (specific gravity: 250 g/m²) of 100% polyethylene terephthalate were used.

(Synthesis of Polyester Flame Retarding Agent 1)

A compound obtained by the same method as that described in "Synthesis of phosphorus compound (1)" above was used as polyester flame retarding agent 1.

(Synthesis of Polyester Flame Retarding Agent 2)

A compound obtained by the same method as that described in "Synthesis of phosphorus compound (2)" above was used as polyester flame retarding agent 2.

(Synthesis of Polyester Flame Retarding Agent 3)

A compound obtained by the same method as that described in "Synthesis of phosphorus compound (3)" above was used as polyester flame retarding agent 3.

Synthesis Example 13

Synthesis of Polyester Flame Retarding Agent 4

(Synthesis of Intermediate 7)

A fresh 2-liter four-neck flask equipped with a stirrer, a thermometer, a dripping device, and a reflux tube was filled with 138.0 g (1 mol) of diethyl phosphite (produced by Johoku Chemical Co., Ltd.) and 20.2 g (0.2 mol) of triethylamine. While the mixed solution was stirred, 31.9 g of 94% paraformaldehyde was added thereto at 60° C. over 1 hour. After that, the substances were reacted at the same temperature (60° C.) for 2 hours, thereby obtaining a solution containing diethyl (hydroxymethyl) phosphonate (intermediate 7) as a main component.

(Synthesis of Polyester Flame Retarding Agent 4)

Polyester flame retarding agent 4 was obtained in substantially the same manner as in the method described in "Synthesis of polyester flame retarding agent 3" except that a solution containing intermediate 7 after the reaction was terminated was used.

(Synthesis of Polyester Flame Retarding Agent 5)

A compound obtained by the same method as that described in "Synthesis of phosphorus compound (4)" above was used as polyester flame retarding agent 5.

(Synthesis of polyester Flame Retarding Agent 6)

Polyester flame retarding agent 6 was obtained in conformity with EXAMPLE 10 described in U.S. Pat. No. 4,697,030.

(Synthesis of Polyester Flame Retarding Agent 8)

A compound obtained by the same method as that described in "Synthesis Example 7" above was used as polyester flame retarding agent 8.

(Production of Flame Retardation Processing Agents for Polyesters)

(Hereinafter, for the sake of simplicity, flame retardation processing agents 1, 2, . . . for polyester will be referred to as "polyester flame retardation processing agents 1, 2, . . . .)

(Production of Polyester Flame Retardation Processing Agent 1)

40 g of polyester flame retarding agent 1 and 5 g of ethylene oxide 15 mol adduct of tristyrenated phenol as a surfactant were mixed, and 55 g of hot water was added thereto while stirring the mixture. After that, 0.2 g of carboxymethylcellulose was added as a dispersion stabilizer, thereby obtaining polyester flame retardation processing agent 1 in a form of white dispersion.

(Production of Polyester Flame Retardation Processing Agent 2)

40 g of polyester flame retarding agent 2 and 5 g of ethylene oxide 20 mol adduct of tristyrenated phenol as a surfactant were mixed, and 55 g of hot water was added thereto while stirring the mixture. After that, 0.2 g of xanthan gum was added as a dispersion stabilizer, thereby obtaining polyester flame retardation processing agent 2 in a form of white dispersion.

(Production of Polyester Flame Retardation Processing Agent 3)

Polyester flame retardation processing agent 3 in a form of white dispersion was obtained in substantially the same manner as in the method described in "Production of polyester flame retardation processing agent 1" except that polyester flame retarding agent 3 was used instead of polyester flame retarding agent 1.

(Production of Polyester Flame Retardation Processing Agent 4)

Polyester flame retardation processing agent 4 in a form of white dispersion was obtained in substantially the same manner as in the method described in "Production of polyester flame retardation processing agent 1" except that polyester flame retarding agent 4 was used instead of polyester flame retarding agent 1.

(Production of Polyester Flame Retardation Processing Agent 5)

Polyester flame retardation processing agent 5 in a form of white dispersion was obtained in substantially the same manner as in the method described in "Production of polyester flame retardation processing agent 1" except that polyester flame retarding agent 5 was used instead of polyester flame retarding agent 1.

(Production of Polyester Flame Retardation Processing Agent 6)

Polyester flame retardation processing agent 6 in a form of white dispersion was obtained in substantially the same manner as in the method described in "Production of polyester flame retardation processing agent 1" except that polyester flame retarding agent 6 was used instead of polyester flame retarding agent 1.

(Production of Polyester Flame Retardation Processing Agent 7)

40 g of polyester flame retarding agent 7 and 5 g of ethylene oxide 20 mol adduct of tristyrenated phenol as a surfactant were mixed, and 55 g of hot water was added thereto while stirring the mixture. After that, 0.2 g of carboxymethylcellulose was added as a dispersion stabilizer, thereby obtaining polyester flame retardation processing agent 7 in a form of white dispersion.

(Production of Polyester Flame Retardation Processing Agent 8)

Polyester flame retardation processing agent 8 in a form of white dispersion was obtained in substantially the same manner as in the method described in "Production of polyester flame retardation processing agent 1" except that polyester flame retarding agent 8 was used instead of polyester flame retarding agent 1.

(Suitability Tests for the Flame Retardation Processing Agents)

The suitability of the polyester flame retardation processing agents for a polyester fiber was checked by a hydrolysis resistance test and an emulsification stability test described below.

(1) Hydrolysis Resistance Test

A hydrolysis resistance test was performed as follows. Polyester flame retarding agents 1 through 4 (polyester examples 1 through 4) and polyester flame retarding agent 6 (polyester comparative example 1) were each weighed and put into a glass cylinder with no lid (30 mm (diameter)×80 mm (height)). Each agent was kept in a saturated water vapor pressure atmosphere (130° C.×1 hour). The increase in the ratio of the acid value of an acid component of each agent was calculated based on the post-hydrolysis resistance test value and pre-hydrolysis resistance test value.

(2) Emulsification Stability Test

Polyester flame retardation processing agents 1 through 4 (polyester examples 1 through 4) and polyester flame retardation processing agent 6 (polyester comparative example 1) were kept at 60° C. for 2 hours. The emulsification stability of each agent was evaluated by visual observation. Table 7 shows the result of the hydrolysis resistance test and the emulsification stability test performed on polyester flame retardation processing agents 1 through 4 (polyester examples 1 through 4) and polyester flame retardation processing agent 6 (polyester comparative example 1). In Table 7, "◯" represents very good, "Δ" represents good, and "X" represents bad.

TABLE 7

|  | Polyester examples | | | | Polyester comparative examples |
| --- | --- | --- | --- | --- | --- |
|  | 1 | 2 | 3 | 4 | 1 |
| Phosphorus compound | Agent 1 | Agent 2 | Agent 3 | Agent 4 | Agent 6 |
| Increased ratio of acid value[1] | 36.7% | 26.8% | 0.6% | 3.4% | 78.2% |
| Emulsification stability | ◯ | ◯ | ◯ | ◯ | X |

[1]Increased ratio of acid value = (post-test acid value − pre-test acid value)/theortical total acid value In Table 7, a greater increased ratio of acid value means that the phosphorus compound is more liable to hydrolysis by saturated water vapor.

Comparing the phosphorus compounds used for a polyester fiber in polyester examples 1 through 4 according to the present invention (polyester flame retarding agents 1 through 4) with the phosphorus compound as polyester comparative example 1 (polyester flame retarding agent 6), the phosphorus compound as polyester comparative example 1 is understood to be more liable to hydrolysis.

Comparing the phosphorus compound in polyester example 4 (polyester flame retarding agent 4) with the phosphorus compound as polyester comparative example 1 (polyester flame retarding agent 6), the former has a higher hydrolysis resistance owing to the cyclic structure thereof.

Reviewing the results of the emulsification stability test, the phosphorus compound as polyester comparative example 1 (polyester flame retarding agent 6) cannot be considered to have a good emulsification stability, as compared to the phosphorus compounds in polyester examples 1 through 0.4 (polyester flame retarding agents 1 through 4).

From these results, it is reasonably expected that, for example, when a conventional phosphorus compound such as polyester flame retarding agent 6 or the like is used as an aqueous flame retardation processing agent in an emulsified and dispersion state, the acid component generated by hydrolysis deteriorates the emulsification stability of the flame retardation processing agent, and thus causes defects such as uneven dyeing, oil spots and the like when the fiber is heated and processed to be flame-retarded.

(Method for Flame-Retardation Processing of a Polyester Fiber)

(Processing Method 1)

A flame retardation processing agent was added to a dyeing bath of 2% o.w.f. of a dispersion dye (Kayaron Polyester Blue; produced by Nippon Kayaku Co., Ltd.) such that the concentration of the flame retardation processing agent would be 7.5%. Polyester fiber woven fabrics (specific gravity: 250 g/m$^2$) of 100% polyethylene terephthalate were immersed in the resultant bath at a bath ratio of 1:20 at 130° C.×60 minutes using a mini color tester (produced by Techsum Giken Co., Ltd.). The fabrics were reduction-cleaned, rinsed with water, dried (100° C.×5 minutes), and then heat-treated (170° C.×1 minute).

(Processing Method 2)

Polyester fiber woven fabrics (specific gravity: 250 g/m$^2$) of 100% polyethylene terephthalate dyed with a thick-color pigment were immersed in an aqueous dispersion adjusted to have a flame retardation processing agent concentration of 7.5%, and squeezed by a mangle such that the pickup would be 70% to 80%. Then, the polyester fiber fabrics were dried (110° C.×3 minutes) and heated-treated (180° C.×1 minute). Then, the polyester fiber woven fabrics were rinsed with water and dried.

The physical properties of polyester fiber woven fabrics obtained by the following polyester examples and polyester comparative examples were measured according to the following tests.

(1) Flame Retarding Property Test

The flame retarding property (or the flame resistant property) of the polyester fiber woven fabrics obtained by processing methods 1 and 2 described above was evaluated in conformity with Method D described in JIS L 1091. The test was performed on the polyester fiber woven fabrics before being washed, after being washed 5 times in accordance with JIS L 0.1042, and after being dry-cleaned 5 times in accordance with JIS L 1018.

(2) Dyeability

The test pieces of polyester fiber woven fabrics obtained by processing methods 1 and 2, before being washed, after being washed as above, and after being dry-cleaned 5 times as above were evaluated regarding the dyeability by visual observation. The fabrics were evaluated as "no defect" or "defective".

(3) Texture (Feel)

The test pieces of polyester fiber woven fabrics obtained by processing methods 1 and 2, before being washed, after being washed as above, and after being dry-cleaned 5 times as above were evaluated regarding the texture (feel) by touching. The fabrics were evaluated as "very good", "good", or "bad".

Polyester Examples 5 Through 8 and Polyester Comparative Example 2

Tables 8A through 8C show the physical properties of the polyester fiber woven fabrics obtained by processing method 1 using polyester flame retardation processing agents 1 through 4 (polyester examples 5 through 8) and polyester flame retardation processing agent 7 (polyester comparative example 2).

TABLE 8A

| | Flame retarding property (Method D; number of times of contacting flame) | | |
| --- | --- | --- | --- |
| Processing method 1 | Before being washed | After being washed 5 times | After being dry-cleaned 5 times |
| Polyester example 5 | 5 | 5 | 5 |
| Polyester example 6 | 5 | 5 | 5 |
| Polyester example 7 | 5 | 5 | 5 |

TABLE 8A-continued

| | Flame retarding property (Method D; number of times of contacting flame) | | |
|---|---|---|---|
| Processing method 1 | Before being washed | After being washed 5 times | After being dry-cleaned 5 times |
| Polyester example 8 | 5 | 5 | 5 |
| Polyester comparative example 2 | 4 | 4 | 4 |

TABLE 8B

| | Dyeability | | |
|---|---|---|---|
| Processing method 1 | Before being washed | After being washed 5 times | After being dry-cleaned 5 times |
| Polyester example 5 | No defect | No defect | No defect |
| Polyester example 6 | No defect | No defect | No defect |
| Polyester example 7 | No defect | No defect | No defect |
| Polyester example 8 | No defect | No defect | No defect |
| Polyester comparative example 2 | No defect | No defect | No defect |

TABLE 8C

| | Texture (feel) | | |
|---|---|---|---|
| Processing method 1 | Before being washed | After being washed 5 times | After being dry-cleaned 5 times |
| Polyester example 5 | Good | Good | Good |
| Polyester example 6 | Good | Good | Good |
| Polyester example 7 | Good | Good | Good |
| Polyester example 8 | Good | Good | Good |
| Polyester comparative example 2 | Good | Good | Good |

Polyester Examples 9 Through 13 and Polyester Comparative Example 3

Tables 9A through 9C show the physical properties of the polyester fiber woven fabrics obtained by processing method 2 using polyester flame retardation processing agents 1 through 5 (polyester examples 9 through 13) and polyester flame retardation processing agent 7 (polyester comparative example 3).

TABLE 9A

| | Flame retarding property (Method D; number of times of contacting flame) | | |
|---|---|---|---|
| Processing method 2 | Before being washed | After being washed 5 times | After being dry-cleaned 5 times |
| Polyester example 9 | 5 | 5 | 5 |
| Polyester example 10 | 5 | 5 | 5 |
| Polyester example 11 | 5 | 5 | 5 |
| Polyester example 12 | 5 | 5 | 5 |
| Polyester example 13 | 5 | 5 | 5 |
| Polyester comparative example 3 | 4 | 4 | 4 |

TABLE 9B

| | Dyeability | | |
|---|---|---|---|
| Processing method 2 | Before being washed | After being washed 5 times | After being dry-cleaned 5 times |
| Polyester example 9 | No defect | No defect | No defect |
| Polyester example 10 | No defect | No defect | No defect |
| Polyester example 11 | No defect | No defect | No defect |
| Polyester example 12 | No defect | No defect | No defect |
| Polyester example 13 | No defect | No defect | No defect |
| Polyester comparative example 3 | No defect | No defect | No defect |

TABLE 9C

| | Texture (feel) | | |
|---|---|---|---|
| Processing method 2 | Before being washed | After being washed 5 times | After being dry-cleaned 5 times |
| Polyester example 9 | Good | Good | Good |
| Polyester example 10 | Good | Good | Good |
| Polyester example 11 | Good | Good | Good |
| Polyester example 12 | Good | Good | Good |
| Polyester example 13 | Good | Good | Good |
| Polyester comparative example 3 | Good | Good | Good |

As is clear from the results shown in Tables 8A through 8C and Tables 9A through 9C, the flame retardant polyester fibers formed of phosphate-phosphonate compounds indicated in polyester examples 5 through 13 according to the present invention (although the phosphate-phosphonate compounds are non-halogen-based compounds) exhibited superior flame retarding properties before washing, after washing, and after dry-cleaning than those of the flame retardant polyester fibers formed of hexabromocyclododecane which is a halogen-based compound (polyester comparative examples 2 and 3). The flame retardant polyester fibers treated with the phosphorus compounds also exhibited excellent physical properties as fibers including dyeability and texture (feel).

From the results shown in Tables 8A through 8C, it is appreciated that by adding phosphorus compounds according to the present invention to the dyeing bath (processing method 1), polyester fibers which are provided with flame retarding property at the time of dyeing can be obtained.

From the results shown in Tables 9A through 9C, it is appreciated that in processing method 2 by using pre-dyed fiber woven fabrics, the resultant flame retardant polyester fibers can maintain superb physical properties as fibers including dyeability and texture (feel).

In the polyester examples described above, phosphorus compounds each having a —CH$_2$—O— group as a linking group between a phosphorus atom and a phosphorus atom (phosphorus compounds in which the phosphorus atoms are linked by a "P—CH$_2$—O—P" structure) were used. The above tests were performed using phosphorus compounds having a —CH(CH$_3$)—O— group as a linking group, (phosphorus compounds in which the phosphorus atoms are linked by a "P—CH(CH$_3$)—O—P" structure). The results were as good as those of the above-mentioned polyester examples. The results are specifically as follows.

Polyester Examples 14 and 15

Table 10 shows the physical properties of the polyester fiber woven fabrics obtained by processing method 1 (polyester example 14) and processing method 2 (polyester example 15) using polyester flame retardation processing agent 8.

TABLE 10

| | Flame retarding property (Method D; number of times of contacting flame) | | | | |
|---|---|---|---|---|---|
| | Before being washed | After being washed 5 times | After being dry-cleaned 5 times | Dyeability | Texture (feel) |
| Processing method 1 | 5 | 5 | 5 | No defect | Good |
| Processing method 2 | 5 | 5 | 5 | No defect | Good |

A flame retarding agent for polyurethane according to the present invention will be described more specifically below by way of synthesis examples, "polyurethane examples", and "polyurethane comparative examples", but the present invention is not limited by these examples.

Phosphorus compounds obtained by the synthesis examples, and components thereof used in the polyurethane examples and polyurethane comparative examples will be described below.

(a) Phosphorus Compound (Flame Retarding Agent for Polyurethane) Components (Hereinafter, for the sake of simplicity, flame retarding agents 1, 2, . . . for polyurethane will be referred to as "polyurethane flame retarding agents 1, 2, . . . .")

Polyurethane flame retarding agent 1: the following compound

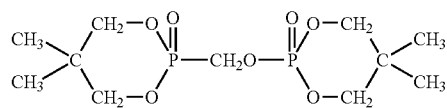

Polyurethane flame retarding agent 2: the following compound

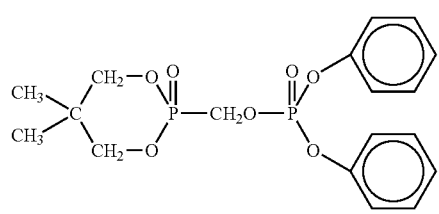

Polyurethane flame retarding agent 3: the following compound

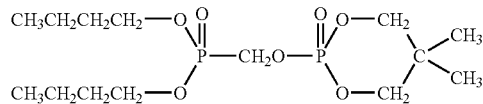

Polyurethane flame retarding agent 4: the following compound

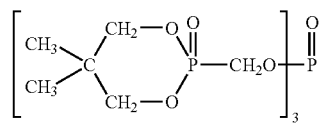

Polyurethane flame retarding agent 5: a mixture of two types phosphorus compounds containing of halogen (chlorine) represented by the following formulas (trade name: UF-500; acid value: 0.03 KOHmg/g; produced by Daihachi Chemical Industry Co., Ltd.)

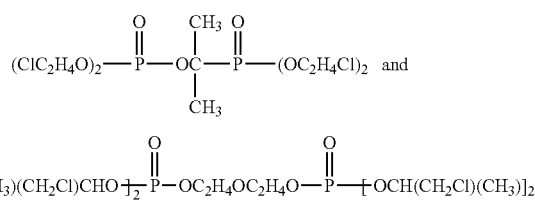

Polyurethane flame retarding agent 6: synthesis product obtained in conformity with EXAMPLE 9 described in U.S. Pat. No. 4,697,030

Polyurethane flame retarding agent 7: the following compound

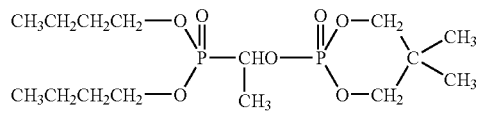

Polyurethane flame retarding agent 8: the following compound

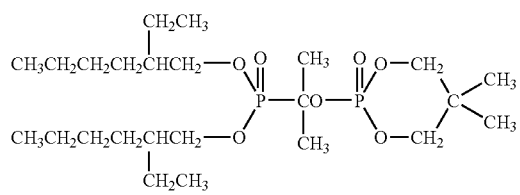

Polyurethane flame retarding agent 9: the following compound

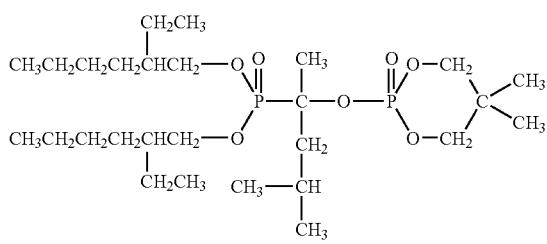

Polyurethane flame retarding agent 10: the following compound

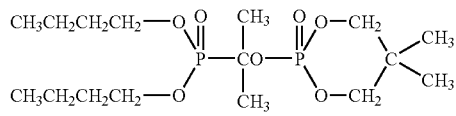

Polyurethane flame retarding agent 11: the following compound

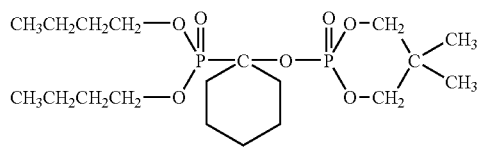

(b) Polyol Component

Polyol 1: trifunctional polypropyleneglycol-type polyetherpolyol (number average molecular weight: 3000; hydroxyl value: 56.0 KOHmg/g)(trade name: MN-3050 ONE; produced by Mitsui Takeda Chemicals, Inc.)

Polyol 2: polyfunctional polypropyleneglycol-type polyetherpolyol (number average molecular weight: 400; hydroxyl value: 460 KOHmg/g)(trade name: SU-464; produced by Mitsui Takeda Chemicals, Inc.)

(c) Polyisocyanate Component

Polyisocyanate 1: tolylene diisocyanate (2,4-/2,6-isomer ratio: 80/20) (trade name: Cosmonate T-80; produced by Mitsui Takeda Chemicals, Inc.)

Polyisocyanate 2: diphenylmethane 4,4'-diisocyanate (trade name: Cosmonate M-200; produced by Mitsui Takeda Chemicals, Inc.)

(d) Catalyst Component (d1) Amine Catalyst

Amine catalyst 1: dipropyleneglycol solution containing 33% by weight of triethylenediamine (trade name: DABCO 33LV; produced by Sankyo Air Products Co., Ltd.)

Amine catalyst 2: dipropyleneglycol solution containing 70% by weight of bis-(2-dimethylaminoethyl) ether (trade name: NIAX A1; produced by Crompton Specialities Limited)

Amine catalyst 3: triethanolamine (special grade reagent; Wako Pure Chemical Industries, Ltd.)

Amine catalyst 4: N,N,N',N'',N''-pentamethyldiethylenetriamine (trade name: Kaolizer No. 3; produced by Kao Corporation)

(d2) Tin Catalyst

Tin catalyst 1: stannous octate (trade name: DABCO T-9; produced by Sankyo Air Products Co., Ltd.)

(e) Silicone Foam Stabilizer Component

Foam stabilizer 1: L-620 (trade name: L-620; produced by Crompton Specialities Limited)

Foam stabilizer 2: SH-193 (trade name: SH-193; produced by Dow Corning Toray Silicone Co., Ltd.)

(f) Foaming Agent Component

Foaming agent 1: water

Foaming agent 2: dichloromethane (special grade reagent; Wako Pure Chemical Industries, Ltd.)

Other Components

Melamine: melamine powder having a particle diameter of 40 to 50 μm (Nissan Chemical Industries, Ltd.)

Examples of synthesizing phosphorus compounds according to the present invention will be described. The present invention is not limited to these synthesis methods.

(Synthesis of Polyurethane Flame Retarding Agent 1)

A compound obtained by the same method as that described in "Synthesis of phosphorus compound (1)" above was used as polyurethane flame retarding agent 1. Polyurethane flame retarding agent 1 had an acid value of 0.04 KOHmg/g.

(Synthesis of Polyurethane Flame Retarding Agent 2)

A compound obtained by the same method as that described in "Synthesis of phosphorus compound (2)" above was used as polyurethane flame retarding agent 2. Polyurethane flame retarding agent 2 had an acid value of 0.03 KOHmg/g.

(Synthesis of Polyurethane Flame Retarding Agent 3)

A compound obtained by the same method as that described in "Synthesis of phosphorus compound (3)" above was used as polyurethane flame retarding agent 3. Polyurethane flame retarding agent 3 had an acid value of 0.05 KOHmg/g.

(Synthesis of Polyurethane Flame Retarding Agent 4)

A compound obtained by the same method as that described in "Synthesis of phosphorus compound (4)" above was used as polyurethane flame retarding agent 4. Polyurethane flame retarding agent 4 had an acid value of 0.09 KOHmg/g.

(Synthesis of Polyurethane Flame Retarding Agent 6)

Polyurethane flame retarding agent 6 was obtained in conformity with EXAMPLE 9 described in U.S. Pat. No. 4,697,030. The physical properties of resultant polyurethane flame retarding agent 6 were shown below; hydroxyl value: 167 KOHmg/g (value described in EXAMPLE 9: 173 KOHmg/g); acid value: 1.4 KOHmg/g (value described in EXAMPLE 9: 0.8 KOHmg/g).

(Synthesis of Polyurethane Flame Retarding Agent 7)

A compound obtained by the same method as that described in "Synthesis example 7" above was used as polyurethane flame retarding agent 7. Polyurethane flame retarding agent 7 had an acid value of 0.06 KOHmg/g.

(Synthesis of Polyurethane Flame Retarding Agent 8)

A compound obtained by the same method as that described in "Synthesis of phosphorus compound (5)" above was used as polyurethane flame retarding agent 8. Polyurethane flame retarding agent 8 had an acid value of 0.06 KOHmg/g.

(Synthesis of Polyurethane Flame Retarding Agent 9)
A compound obtained by the same method as that described in "Synthesis example 10" above was used as polyurethane flame retarding agent 9. Polyurethane flame retarding agent 9 had an acid value of 0.07 KOHmg/g.

(Synthesis of Polyurethane Flame Retarding Agent 10)
A compound obtained by the same method as that described in "Synthesis example 11" above was used as polyurethane flame retarding agent 10. Polyurethane flame retarding agent 10 had an acid value of 0.06 KOHmg/g.

(Synthesis of Polyurethane Flame Retarding Agent 11)
A compound obtained by the same method as that described in "Synthesis example 12" above was used as polyurethane flame retarding agent 11. Polyurethane flame retarding agent 11 had an acid value of 0.07 KOHmg/g.

The physical properties of the resin compositions obtained in the following polyurethane examples and polyurethane comparative examples were tested as follows.

I. Tests for Flexible Polyurethane Foams (1) Horizontal Combustion Test
Test method: in conformity with FMVSS-302
Test sample: length: 250 mm; width 70 mm; thickness: 5 mm
Evaluation criteria: the average combustion rate must be 100 mm/minute or less; when not exceeding the A standard line (38 mm standard line), combustion distance (mm) was indicated.

(2) UL Flame Resistance Test
Test method: in conformity with UL94(HF test)
Test sample: length: 152 mm; width 50.8 mm; thickness: 12.7 mm
Evaluation: classified as HF-1, HF-2, or HBF (3) Fogging Test
Test sample thickness: 10 mm
Test sample diameter: 80 mm
Foamed pieces having the above-mentioned dimensions each were stored in a glass cylinder at 110° C. for 3 hours. The amount of volatile substance attached to a top glass plate was measured. A cooling device was provided to the top of the glass plate such that the glass plate could be cooled to 20° C.

(4) Residual Distortion by Compression
Test method: in conformity with JIS K-6400
Foam sample: length: 6 cm; width: 6 cm; thickness: 5 cm
The surface of each of 6 cm×6 cm foam samples was compressed by 50% at 70° C.×22 hours. After the samples were released from the compression, the thickness of the samples was measured. The ratio of the measured reduced thickness with respect to the pre-compression thickness was calculated as the residual distortion by compression. For example, when the 5 cm thick foam sample became a 4 cm thick foam sample, the residual distortion by compression is (1/5)×100=20%.

II. California 117 Combustion Tests (1) Vertical Combustion Test
Test method: in conformity with California 117, Section A, Part I. test method
Test sample: length: 305 mm; width 75.0 mm; thickness: 13.0 mm
Evaluation criteria: 5 test samples stored at room temperature and 5 test samples heat-aged (104±2° C., stored for 24 hours) were subjected to a vertical combustion test. The average combustion distance (which must be 147 mm or less), the maximum combustion distance (which must be 196 mm or less), the average combustion time (which must be 5 seconds or less), and the maximum combustion time (which must be 10 seconds or less) were determined. Foams fulfilling all of the four conditions were determined to "pass".

(2) Chair-Type Combustion Test (Smolder Combustion Test)
Test method: in conformity with California 117, Section D, Part II. test method
Test Sample:
Foam sample A: length: 203 mm; width 184 mm; thickness: 51 mm
Foam sample B: length: 203 mm; width 102 mm; thickness: 51 mm
Covering Cloth:
For foam sample A: length: 375 mm; width 200 mm
For foam sample B: length: 275 mm; width 200 mm
Thin cloth: length: 150 mm; width 150 mm
Wooden frame: chair-type frame accommodating the above test sample
Evaluation criteria: Foam samples A and B were each covered with a covering cloth having a suitable size and set to a prescribed wooden frame. The covering cloth on the back of the chair was fixed to the frame with cellophane tape. A prescribed cigarette (CABIN LIGHT 100's) was lit, the filter portion was detached, and set to the foam sample which had been set to the chair-type frame. More specifically, the cigarette was set to a portion of the foam sample at the center of the back of the chair. The cigarette was covered with a thin cloth. After the fire of the cigarette was put out, the residues by the combustion were removed. The pre-test and post-test weight of each foam sample were compared. The test was performed at n=3. When the remaining ratio of each of all the samples was 80% or greater, the foam was determined to "pass".

III. British Standard 5852 Combustion Test
Test method: in conformity with BS5852 Schedule 1, Part 1, Source 5 test method
Test Sample:
A: length: 450 mm; width: 450 mm; thickness: 75 mm
B: length: 300 mm; width: 450 mm; thickness: 75 mm
Evaluation criteria: Each of samples as mentioned above was covered with a cloth as prescribed and shaped like a chair. A combustion wooden frame created as prescribed was set to the center of the back of the chair. The lint fabric at the bottom was soaked with 1.4 ml n-butanol and lit.
After flame time and after glow time: 10 minutes or less Lost weight: 60 g or less
The test was performed at n=2. When all the samples fulfill the above conditions, the foam was determined to "pass".

IV. Tests for Rigid Polyurethane Foams (1) Combustion Test
Test method: in conformity with JIS A-9511 (combustion test method B).
Test sample: length: 150 mm; width 50 mm; thickness: 13 mm (2) Bending Test
Test method: in conformity with JIS K-7221-1
Test sample: length: 120 mm; width 25 mm; thickness: 20 mm (3) Compression Test Test method: in conformity with JIS K-7220

Test sample: length: 50 mm; width 50 mm; thickness: 30 mm (Production of Polyurethane Foams)

Flexible and rigid polyurethane foams were produced by the following one-shot method. Polyol, a silicone foam stabilizer, an amine catalyst, water, and a phosphorus compound were mixed, and stirred by a stirrer having a rotation rate of 3500 rpm for 1 minute to admix the substances uniformly. In the case of a flexible polyurethane foam, a tin catalyst and dichloromethane were further added, and stirred for another 10 seconds. Then, diisocyanate was added to the premixed substances and stirred at 3500 rpm for 5 to 7 seconds. The resultant mixture was put into a cubic cardboard box suitable for the foaming volume. Several seconds later, foaming occurred, and several minutes later, the volume reached the maximum level. In the case of a flexible foam, the obtained substance was dried and cured in a drier at 75° C. for 20 minutes. The obtained flexible foam was white and had continuous air bubbles. The obtained rigid foam was brown and was not air-permeable.

Regarding various polyurethane foams obtained by the above method, the time from the premixed substances were put into the cardboard box until the volume achieved the maximum level (rise time (RT)) was measured. A piece of each test sample which passed the test standards was cut out, and stored in a constant-temperature, constant-humidity device for 24 hours or longer. The density (JIS K-6400)(kg/m$^3$) and the air permeability (JIS K-6400)(ml/cm$^2$/sec) of the samples were measured. Then, as a physical property, the residual distortion by compression was measured (JIS K-6400)(%). As combustion tests, the following tests were performed: A horizontal combustion test of the slab foams for automobile (FMVSS-302); a combustion test in conformity with combustion standard UL94 (HF test) for foams used as electric materials; and a combustion test in conformity with California 117 test for foams used for furniture. In addition, a heat resistance test was performed by keeping the foams in a microwave oven (500 W)×3 minutes and in a heat air drier at 140° C.×3 hours. The yellowed state (scorch resistance) of the foams was indicated by degree of yellowing (JIS K-7105). In a fogging test, the ratio of the volatile component was quantitated numerically by a spectroscope.

Polyurethane Examples 1 Through 12 and Polyurethane Comparative Examples 1 Through 6

Tables 11 through 14 show the test results together with the flexible polyurethane foam components and the ratios thereof. In these tables the "examples" means polyurethane examples and "comparative examples" or "comparative" means "polyurethane comparative examples". Arrows "→" means that the value in that section is identical with the value in the section to the left. For example, in Table 11, the amount of the tin catalyst of Example 2 is the same as that of Example 1, i.e., 0.33 parts by weight.

TABLE 11

Ratios of general flexible polyurethane foam components and evaluation results thereof

| | | Examples | | | | Comparative examples | |
|---|---|---|---|---|---|---|---|
| | | 1 | 2 | 3 | 4 | 1 | 2 |
| Amount (parts by weight) | Polyol 1 | 100 | → | → | → | → | → |
| | Amine catalyst 1 | 0.18 | → | → | → | → | → |
| | Amine catalyst 2 | 0.05 | → | → | → | → | → |
| | Tin catalyst 1 | 0.33 | → | → | → | 0.26 | → |
| | Foaming agent 1 | 4.3 | → | → | → | → | → |
| | Foaming agent 2 | 8.0 | → | → | → | → | → |
| | Flame retardant agent 1 | 12 | — | — | — | — | — |
| | Flame retardant agent 2 | — | 16 | — | — | — | — |
| | Flame retardant agent 3 | — | — | 16 | — | — | — |
| | Flame retardant agent 4 | — | — | — | 10 | — | — |
| | Flame retardant agent 5 | — | — | — | — | 16 | — |
| | Flame retardant agent 6 | — | — | — | — | — | 16 |
| | Foam stabilizer 1 | 1.0 | → | → | → | → | → |
| | Polyisocyanate 1 | 57.8 | → | → | → | → | → |
| Physical property | Rise time (RT) (sec) | 88 | 89 | 82 | 87 | 86 | Form non-produceable |
| | Foam density (kg/m$^3$) | 22.5 | 21.8 | 22.2 | 22.0 | 22.5 | |
| | Air permeability (ml/cm$^2$/sec) | 170 | 170 | 150 | 156 | 167 | |
| | Scorch resistance (ΔYI) | 40 | 32 | 44 | 47 | 75 | |
| | FMVSS-302 test: Combustion distance (mm) | 35.5 | 35.1 | 32.3 | 30.4 | 37.0 | |
| | UL94 (HF combustion test) | HF-1 | HF-1 | HF-1 | HF-1 | HBF | |
| | Fogging test (110° C. × 3 hrs.; cooled) Amount* (mg) | <0.1 | <0.1 | <0.1 | <0.1 | 1.3 | |
| | Light reflectance (%) | 100 | 98 | 90 | 100 | 80 | |
| | Haze (ΔHz) | 0.1 | 0.4 | 0.6 | 0.2 | 1.8 | |
| | Residual distortion by compression (compressed by 50%) (%) | 2.0 | 4.0 | 2.7 | 3.0 | 3.2 | |

Note*:
The amount of volatile substance attached to a top glass plate

TABLE 12A

Ratios of flexible polyurethane foam components for the California 117 tests

| | | Examples | | | | Comparative example 3 |
|---|---|---|---|---|---|---|
| | | 5 | 6 | 7 | 8 | |
| Amount (parts by weight) | Polyol 1 | 100 | → | → | → | → |
| | Amine catalyst 1 | 0.20 | → | → | → | → |
| | Amine catalyst 2 | 0.05 | → | → | → | → |
| | Amine catalyst 3 | 0.05 | → | → | → | → |
| | Tin catalyst 1 | 0.33 | → | → | → | → |
| | Foaming agent 1 | 4.3 | → | → | → | → |
| | Foaming agent 2 | 8.0 | → | → | → | → |
| | Flame retardant agent 1 | 12 | — | — | — | — |
| | Flame retardant agent 2 | — | 16 | — | — | — |
| | Flame retardant agent 3 | — | — | 14 | — | — |
| | Flame retardant agent 4 | — | — | — | 12 | — |
| | Flame retardant agent 5 | — | — | — | — | 14 |
| | Foam stabilizer 1 | 1.0 | → | → | → | → |
| | Polyisocyanate 1 | 57.8 | → | → | → | → |

TABLE 12B

Evaluation results of flexible polyurethane foams by the California 117 tests

| | | Examples | | | | Comparative Example |
|---|---|---|---|---|---|---|
| | | 5 | 6 | 7 | 8 | 3 |
| Physical property | Rise time (RT) (sec) | 96 | 95 | 87 | 98 | 98 |
| | Foam density (kg/m$^3$) | 22.7 | 21.9 | 22.0 | 22.5 | 22.7 |
| | Air permeability (ml/cm$^2$/sec) | 121 | 111 | 100 | 105 | 100 |
| Cal. 117. Section A Part I | Before heat-aging Combustion distance (mm)/ Flame remaining time (sec) | 98  0<br>87  0<br>92  0<br>111 0<br>105 0 | 83  0<br>134 2<br>101 0<br>138 3<br>82  0 | 99  0<br>103 2<br>106 1<br>98  0<br>83  0 | 88  0<br>75  0<br>91  0<br>87  0<br>86  0 | 100 2<br>97  0<br>97  0<br>83  0<br>102 2 |
| | Average | 98.6 0 | 107.6 1 | 97.8 0.6 | 85.4 0 | 99.8 0.8 |
| | After heat-aging Combustion distance (mm)/ Flame remaining time (sec) | 86  0<br>101 0<br>98  0<br>104 0<br>99  0 | 103 0<br>94  0<br>97  0<br>121 0<br>124 0 | 87  0<br>85  0<br>91  0<br>101 0<br>96  0 | 73  0<br>86  0<br>92  0<br>77  0<br>63  0 | 97  0<br>101 2<br>97  0<br>99  0<br>105 3 |
| | Average | 97.6 0 | 107.8 0 | 92.0 0 | 78.2 0 | 101.8 1 |
| Cal. 117. Section D Part II | Remaining foam ratio (%) | 98<br>97<br>98 | 90<br>91<br>92 | 98<br>99<br>97 | 97<br>97<br>99 | 92<br>85<br>92 |
| Results | Overall evaluation | Pass | Pass | Pass | Pass | Pass |

TABLE 13

Ratios of flexible polyurethane foam components for British Standard 5852 tests and evaluation results thereof

| | | Examples | | Comparative Example |
|---|---|---|---|---|
| | | 9 | 10 | 4 |
| Amount (parts by weight) | Polyol 1 | 100 | → | → |
| | Amine catalyst 1 | 0.08 | → | → |
| | Amine catalyst 2 | 0.04 | → | → |
| | Amine catalyst 3 | 0.04 | → | → |
| | Tin catalyst 1 | 0.34 | → | → |
| | Foaming agent 1 | 4.6 | → | → |
| | Melamine | 25 | → | → |
| | Flame retardant agent 1 | 20 | — | — |
| | Flame retardant agent 4 | — | 20 | — |
| | Flame retardant agent 5 | — | — | 20 |
| | Foam stabilizer 1 | 1.0 | → | → |
| | Polyisocyanate 1 | 55.8 | → | → |
| Physical property | Rise time (sec) | 92  89 | 99  96 | 92  93 |
| | Foam density (kg/m$^3$) | 29.0 29.3 | 29.2 29.5 | 29.8 29.7 |
| | Air permeability (ml/cm$^2$/sec) | 110  85 | 88  96 | 86  101 |
| BS5852 Schedule 1 Results | Combustion time | 4 min. 02 sec  3 min. 25 sec | 2 min. 37 sec  2 min. 51 sec | 3 min. 19 sec  3 min. 40 sec |
| | Lost weight (g) | 45.4  41.0 | 35.9  38.7 | 39.2  44.3 |
| | Test evaluation | Pass | Pass | Pass |

TABLE 14

Ratios of general rigid polyurethane foam components and evaluation results thereof

|  |  | Examples | | Comparative Examples | |
|---|---|---|---|---|---|
|  |  | 11 | 12 | 5 | 6 |
| Amount (parts by weight) | Polyol 2 | 100 | → | → | → |
|  | Amine catalyst 4 | 0.75 | → | → | → |
|  | Foaming agent 1 | 5.0 | → | → | → |
|  | Flame retardant agent 2 | 14 | — | — | — |
|  | Flame retardant agent 3 | — | 14 | — | — |
|  | Flame retardant agent 6 | — | — | — | 14 |
|  | Foam stabilizer 2 | 2.0 | → | → | → |
|  | Polyisocyanate 2 | 191.3 | → | → | → |
| Physical property | Foam density (kg/m$^3$) | 32.3 | 31.2 | 30.8 | Foam non-produceable |
|  | Combustion test (n = 5): Combustion distance (mm) | 38.7 | 38.2 | BN |  |
|  | Bending test (n = 3) (MPa) | 0.24 | 0.21 | 0.25 |  |
|  | Compression test (n = 3) (MPa) | 0.22 | 0.22 | 0.24 |  |

From the results shown in Tables 11 through 14, it is appreciated that the polyurethane foams using the phosphate-phosphonate compounds according to the present invention have a sufficient level of flame retarding property although not containing halogen.

In polyurethane examples 1 through 4 shown in Table 11, the results of UL-94 combustion test and the fogging characteristics are very good. It is appreciated that the these polyurethane foams have a high level of flame retarding property and also have very little undesirable possibility of the problems of volatile substance (VOC).

In polyurethane comparative example 1 using polyurethane flame retardant agent 5, the polyurethane foam is flame retardant in the horizontal combustion test, but cannot pass the UL94 combustion test standards. It is appreciated that the polyurethane foam in polyurethane comparative example 1 clearly has a volatile substance and cannot be suitable to uses in which the anti-fogging characteristics are important.

In polyurethane comparative example 2 using polyurethane flame retardant agent 6, the polyurethane foam could not be produced. Possible reasons, for example, are considered to be as follows. (i) Since polyurethane flame retardant agent 6 has a hydroxyl group, which is reactive, and thus the foam could not be produced by a general formulation. (ii) Since the acid value of polyurethane flame retardant agent 6 is too high as compared to those of polyurethane flame retardant agents 1 through 4, the catalyst lost its activity, and thus the foam could not be produced.

In polyurethane examples 5 through 8 shown in Tables 12A and 12B, the foams completely cleared the standards for the four items, i.e., the average combustion distance (147 mm or less), the maximum combustion distance (196 mm or less), the average combustion time (5 seconds or less), and the maximum combustion time (10 seconds or less) in the vertical combustion test, both before and after the heat-aging. In the smolder test, satisfactory results were obtained. It is appreciated that these flexible polyurethane foams can be used for furniture with no problems.

In polyurethane comparative example 3, the foam passes the California 117 tests, but uses a halogen-containing flame retardant agent. Therefore, there is a possibility that hazardous substances such as hydrogen halides, dioxin and the like are generated by actual combustion. Therefore, it is considered that the foam in polyurethane comparative example 3 cannot be used in consideration of the future environmental problems.

In polyurethane examples 9 through 10 shown in Table 13, the foams completely cleared the standards for the two items, i.e., the combustion time (10 minutes or less) and the lost weight (60 g or less). It is appreciated that these flexible polyurethane foams can be used for furniture requiring more strict conditions than those of Table 13.

The BS5852 tests are conventionally unfavorable to conventional foams having a low density of 25 to 30 kg/m$^3$, and are often performed on foams having a density of about 35 to 40 kg/m$^3$. In, for example, polyurethane comparative example 4 using a halogen-based flame retardant agent and melamine together, the foam may possibly pass the BS5852 tests, but the flame retardation mechanism often relies on the synergistic effect of halogen and melamine. The fact that a foam using a phosphorus compound according to the present invention, which does not contain halogen, passed the BS5852 tests is very important.

Polyurethane examples 11 and 12 shown in Table 14 relate to use of a compound according to the present invention to rigid polyurethane foams. When compared with polyurethane comparative example 5 which does not use a phosphorus compound, it is appreciated that the phosphorus compound according to the present invention provides a superb flame retarding property without exerting adverse influences on various other physical properties.

In polyurethane comparative example 6 using polyurethane flame retardant agent 6, a polyurethane foam could not be produced. Possible reasons, for example, are as follows, like in the case of polyurethane comparative example 2. (i) Since polyurethane flame retardant agent 6 has a hydroxyl group, which is reactive, and thus the foam could not be produced by a general formulation. (ii) Since the acid value of polyurethane flame retardant agent 6 is too high as compared to those of polyurethane flame retardant agents 2 and 3, the catalyst loses its activity, and thus the foam could not be produced.

In the polyurethane examples described above, phosphorus compounds each having a —CH$_2$—O— group as a linking group between a phosphorus atom and a phosphorus atom (phosphorus compounds in which the phosphorus atoms are linked by a "P—CH$_2$—O—P" structure) were used. The same tests as those described above were performed except that phosphorus compounds having a —CH(CH$_3$)—O— group or the like as a linking group (phosphorus compounds in which the phosphorus atoms are linked by a "P—CH(CH$_3$)—O—P" structure, a "P—C(CH$_3$)$_2$—O—P" structure, a "P—C$_6$H$_{10}$—O—P" structure, or a "P—C(CH$_3$)(CH$_2$CH(CH$_3$)$_2$)—O—P" structure) were used as flame retardant agents. The results were as good as those of the above-mentioned polyurethane examples. The results are specifically as follows.

TABLE 15A

Ratios of general flexible polyurethane foam components and evaluation results thereof

|  |  | Examples |  |  |
|---|---|---|---|---|
|  |  | 13 | 14 | 15 |
| Amount (parts by weight) | Polyol 1 | 100 | → | → |
|  | Amine catalyst 1 | 0.18 | → | → |
|  | Amine catalyst 2 | 0.05 | → | → |
|  | Tin catalyst 1 | 0.33 | → | → |
|  | Foaming agent 1 | 4.3 | → | → |
|  | Foaming agent 2 | 8.0 | → | → |
|  | Flame retardant agent 7 | 16 | — | — |
|  | Flame retardant agent 8 | — | 18 | — |
|  | Flame retardant agent 9 | — | — | 20 |
|  | Foam stabilizer 1 | 1.0 | → | → |
|  | Polyisocyanate 1 | 57.8 | → | → |
| Physical property | Rise time (RT) (sec) | 83 | 89 | 82 |
|  | Foam density (kg/m$^3$) | 22.4 | 22.3 | 22.5 |
|  | Air permeability (ml/cm$^2$/sec) | 163 | 163 | 159 |
|  | Scorch resistance (ΔYI) | 41 | 30 | 25 |
|  | FMVSS-302 test: Combustion distance (mm) | 32.9 | 36.2 | 35.6 |
|  | UL94(HF combustion test) | HF-1 | HF-1 | HF-1 |
|  | Fogging test (110° C. × 3 hrs.; cooled) |  |  |  |
|  | Amount* (mg) | <0.1 | <0.1 | <0.1 |
|  | Light reflectance (%) | 95 | 100 | 100 |
|  | Haze (ΔHz) | 0.3 | 0.1 | 0.1 |
|  | Residual distortion by compression (compressed by 50%) (%) | 3.2 | 2.0 | 2.2 |

Note*:
The amount of volatile substance attached to a top glass plate

TABLE 15B

Ratios of general flexible polyurethane foam components and evaluation results thereof

|  |  | Examples | |
|---|---|---|---|
|  |  | 16 | 17 |
| Amount (parts by weight) | Polyol 1 | 100 | → |
|  | Amine catalyst 1 | 0.18 | → |
|  | Amine catalyst 2 | 0.05 | → |
|  | Tin catalyst 1 | 0.33 | → |
|  | Foaming agent 1 | 4.3 | → |
|  | Foaming agent 2 | 8 | → |
|  | Flame retardant agent 10 | 14 | — |
|  | Flame retardant agent 11 | — | 16 |
|  | Foam stabilizer 1 | 1.0 | → |
|  | Polyisocyanate 1 | 57.8 | → |
| Physical property | Rise time (RT) (sec) | 84 | 85 |
|  | Foam density (kg/m$^3$) | 22.4 | 22.5 |
|  | Air permeability (ml/cm$^2$/sec) | 165 | 160 |
|  | Scorch resistance (ΔYI) | 35 | 32 |
|  | FMVSS-302 test: Combustion distance(mm) | 32.4 | 34.1 |
|  | UL94(HF combustion test) | HF-1 | HF-1 |
|  | Fogging test (110° C. × 3 hrs.; cooled) |  |  |
|  | Amount* (mg) | <0.1 | <0.1 |
|  | Light reflectance (%) | 95 | 100 |
|  | Haze (ΔHz) | 0.3 | 0.1 |
|  | Residual distortion by compression (compressed by 50%) (%) | 2.9 | 2.7 |

Note*:
The amount of volatile substance attached to a top glass plate

TABLE 16A

Ratios of flexible polyurethane foam components for the California 117 tests and evaluation results thereof

|  |  | Examples |  |  |  |  |  |
|---|---|---|---|---|---|---|---|
|  |  | 18 | | 19 | | 20 | |
| Amount (parts by weight) | Polyol 1 | 100 | | → | | → | |
|  | Amine catalyst 1 | 0.20 | | → | | → | |
|  | Amine catalyst 2 | 0.05 | | → | | → | |
|  | Amine catalyst 3 | 0.05 | | → | | → | |
|  | Tin catalyst 1 | 0.33 | | → | | → | |
|  | Foaming agent 1 | 4.3 | | → | | → | |
|  | Foaming agent 2 | 8.0 | | → | | → | |
|  | Flame retardant agent 7 | 14 | | — | | — | |
|  | Flame retardant agent 8 | — | | 20 | | — | |
|  | Flame retardant agent 9 | — | | — | | 22 | |
|  | Foam stabilizer 1 | 1.0 | | → | | → | |
|  | Polyisocyanate 1 | 57.8 | | → | | → | |
| Physical property | Rise time (RT) (sec) | 90 | | 97 | | 96 | |
|  | Foam density (kg/m$^3$) | 22.3 | | 22.1 | | 22.3 | |
|  | Air permeability (ml/cm$^2$/sec) | 108 | | 110 | | 116 | |
| Cal. 117. Section A Part I | Before heat-aging Combustion distance (mm)/ Flame remaining time (sec) | 96 | 0 | 76 | 0 | 75 | 0 |
|  |  | 111 | 0 | 82 | 0 | 88 | 0 |
|  |  | 92 | 0 | 78 | 0 | 80 | 0 |
|  |  | 97 | 0 | 80 | 0 | 80 | 0 |
|  |  | 103 | 0 | 85 | 0 | 81 | 0 |
|  | Average | 99.8 | 0 | 80.2 | 0 | 82.4 | 0 |
|  | After heat-aging Combustion distance (mm)/ Flame remaining time (sec) | 87 | 0 | 74 | 0 | 76 | 0 |
|  |  | 92 | 0 | 81 | 0 | 81 | 0 |
|  |  | 106 | 0 | 83 | 0 | 81 | 0 |
|  |  | 95 | 0 | 83 | 0 | 82 | 0 |
|  |  | 99 | 0 | 82 | 0 | 82 | 0 |
|  | Average | 95.8 | 0 | 80.6 | 0 | 80.4 | 0 |
| Cal. 117. Section D Part II | Foam remaining ratio (%) | 97 | | 97 | | 97 | |
|  |  | 98 | | 98 | | 98 | |
|  |  | 97 | | 98 | | 99 | |
| Results | Overall evaluation | Pass | | Pass | | Pass | |

TABLE 16B

Ratios of flexible polyurethane foam components for the California 117 tests and evaluation results thereof

|  |  | Examples | |
|---|---|---|---|
|  |  | 21 | 22 |
| Amount (parts by weight) | Polyol 1 | 100 | → |
|  | Amine catalyst 1 | 0.2 | → |
|  | Amine catalyst 2 | 0.05 | → |
|  | Amine catalyst 3 | 0.05 | → |
|  | Tin catalyst 1 | 0.33 | → |
|  | Foaming agent 1 | 4.3 | → |
|  | Foaming agent 2 | 8 | → |
|  | Flame retardant agent 10 | 16 | — |

TABLE 16B-continued

Ratios of flexible polyurethane foam components for the California 117 tests and evaluation results thereof

|  |  | Examples | |
|---|---|---|---|
|  |  | 21 | 22 |
|  | Flame retardant agent 11 | — | 18 |
|  | Foam stabilizer 1 | 1.0 | → |
|  | Polyisocyanate 1 | 57.8 | → |
| Physical property | Rise time (RT) (sec) | 91 | 93 |
|  | Foam density (kg/m³) | 22.3 | 22.2 |
|  | Air permeability (ml/cm²/sec) | 112 | 106 |
| Cal. 117. Section A Part I | Before heat-aging Combustion distance (mm)/ Flame remaining time (sec) | 86 0 93 0 102 0 99 0 88 0 | 89 0 93 0 88 0 104 0 95 0 |
|  | Average | 93.6 0 | 93.8 0 |
|  | After heat-aging Combustion distance (mm)/ Flame remaining time (sec) | 94 0 91 0 85 0 98 0 86 0 | 91 0 93 0 88 0 96 0 89 0 |
|  | Average | 90.8 0 | 91.4 0 |
| Cal. 117. Section D Part II | Foam remaining ratio (%) | 97 97 99 | 98 97 97 |
| Results | Overall evaluation | Pass | Pass |

In the section of California 117, Section A, Part I., the numerical value on the left shows the combustion distance (mm) and the numerical value on the right shows the flame remaining time (seconds).

TABLE 17

Ratios of general rigid polyurethane foam components and evaluation results thereof

|  |  | Example 23 |
|---|---|---|
| Amount (parts by weight) | Polyol 2 | 100 |
|  | Amine catalyst 4 | 0.75 |
|  | Foaming agent 1 | 5.0 |
|  | Flame retardant agent 7 | 14 |
|  | Foam stabilizer 2 | 2.0 |
|  | Polyisocyanate 2 | 191.3 |
| Physical property | Foam density (kg/m³) | 31.9 |
|  | Combustion test (n = 5): Combustion distance (mm) | 38.4 |
|  | Bending test(n = 3) (MPa) | 0.21 |
|  | Compression test(n = 3) (MPa) | 0.22 |

A phosphate-phosphonate compound according to the present invention has a high phosphorus content, does not exert influences on physical properties on a product containing the phosphate-phosphonate compound as a material, and does not contain a halogen atom such as a chlorine atom, a bromine atom or the like. Therefore, the phosphate-phosphonate compound according to the present invention does not cause the problem of environmental pollution at the time of combustion or disposal, and is superb in recyclability.

A phosphate-phosphonate compound according to the present invention is very useful as a flame retardant agent for thermoplastic resins including polycarbonate, ABS resins, and PPE; a flame retardant agent for thermosetting resins including polyurethane resins, epoxy resins, and phenol resins; or a flame retardant agent for resins or fibers of polyester including polyethylene terephthalate and polybutylene terephthalate.

Using a flame retardant agent for a polyester according to the present invention, a flame retardant polyester fiber which has a high level of flame retarding property, maintains various good physical properties as a fiber, has a high durability against washing, and does not contain halogen can be obtained. The flame retardant polyester fiber according to the present invention does not contain a halogen atom, and therefore does not generate hazardous halogenated gas at the time of combustion and is effective for environmental protection.

A flame retardant agent for a polyurethane according to the present invention, by using a phosphate-phosphonate compound, provides a polyurethane resin composition having a high level of flame retarding property which can be used for foams including flexible, semi-flexible and rigid forms. A polyurethane foam obtained from a polyurethane resin composition according to the present invention does not generate a volatile substance derived from a flame retardant agent, has a high thermal resistance, and does not substantially lower the physical properties of the foam. Since a polyurethane resin composition for forming a foam according to the present invention is non-halogenic, hazardous substances such as hydrogen halides, dioxin or the like are not generated at the time of combustion, and thus human bodies are not substantially adversely influenced.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A compound represented by the following formula (I):

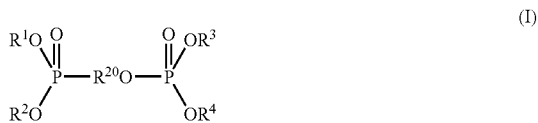

(I)

wherein, in formula (I), $R^1$, $R^2$, $R^3$ and R4 are identical to or different from each other, and are:

a $C_{2-8}$ alkyl group having a straight or branched chain, a $C_{5-10}$ cycloalkyl group which may have one or more substituents, or a $C_{6-15}$ aryl group which may have one or more substituents; or $R^1$ and $R^2$ are combined to become an alkylene group represented by the following formula (II)

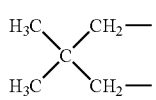

(II)

and form the following cyclic structure A together with the oxygen atoms and the phosphorus atom;

Cyclic structure A:

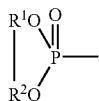

(in cyclic structure A, —R$^1$—R$^2$— is the alkylene group); or R$^3$ and R$^4$ are combined to become an alkylene group represented by the following formula (II)

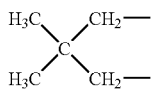

(II)

and form the following cyclic structure B together with the oxygen atoms and the phosphorus atom;

Cyclic structure B:

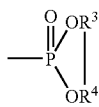

(in cyclic structure B, —R$^3$—R$^4$— is the alkylene group); wherein: the compound indispensably has at least one of cyclic structure A and cyclic structure B; and R$^{20}$ is a linking group having formula 67:

(Formula 67)

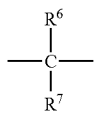

(in formula 67, R$^6$ and R$^7$ may be identical to or different from each other; are either hydrogen, a C$_{1-6}$ alkyl group, or C$_{6-11}$ aryl group; or R$^6$ and R$^7$ may be combined to become a C$_{4-10}$ alkylene group which may have one or more substituents, the C$_{4-10}$ alkylene group forming the following cyclic structure together with the carbon atom

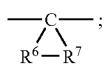

and
a total number of carbons of R$^6$ and R$^7$ is 0 to 12).

2. A compound according to claim 1, wherein R$^1$ and R$^2$ are combined to become an alkylene group represented by the formula (II) and form the cyclic structure A and R$^3$ and R$^4$ are combined to become an alkylene group represented by the formula (II) and form the cyclic structure B.

3. A compound according to claim 1, wherein R$^{20}$ is either a methylene group, a —CH(CH$_3$)— group, or a —C(CH$_3$)$_2$— group.

4. A compound according to claim 1, wherein at least one of R$^3$ and R$^4$ is a C$_{6-15}$ aryl group when the compound has the cyclic structure A, and at least one of R$^1$ and R$^2$ is a C$_{6-15}$ aryl group when the compound has the cyclic structure B.

5. A compound represented by the following formula (III):

(III)

wherein, in formula (III), R$^5$ is a C$_{2-9}$ alkylene group, and R$^{21}$ is a linking group having formula 89:

(Formula 89)

(in formula 89, R$^8$ and R$^9$ may be identical to or different from each other; are either hydrogen, a C$_{1-6}$ alkyl group, or C$_{6-11}$ aryl group; or R$^8$ and R$^9$ may be combined to become a C$_{4-10}$ alkylene group which may have one or more substituents, the C$_{4-10}$ alkylene group forming the following cyclic structure together with the carbon atom

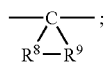

and
a total number of carbons of R$^8$ and R$^9$ is 0 to 12).

6. A compound according to claim 5, wherein R$^{21}$ is either a methylene group, a —CH(CH$_3$)— group, or a —C(CH$_3$)$_2$— group.

7. A compound according to claim 5, wherein R$^5$ is the following formula (IV)

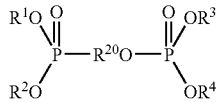

(IV)

8. A flame retardant agent for a resin formed of a compound represented by the following formula (I):

(I)

wherein, in formula (I), R$^1$, R$^2$, R$^3$ and R$^4$ are identical to or different from each other, and are:
 a C$_{2-8}$ alkyl group having a straight or branched chain,
 a C$_{5-10}$ cycloalkyl group which may have one or more substituents,
 a C$_{6-15}$ aryl group which may have one or more substituents; or
R$^1$ and R$^2$ are combined to become an alkylene group represented by the following formula (II)

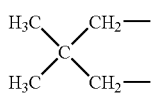
(II)

and form the following cyclic structure A together with the oxygen atoms and the phosphorus atom;

Cyclic structure A:

(in cyclic structure A, —$R^1$—$R^2$— is a $C_{2-9}$ alkylene group); or
$R^3$ and $R^4$ are combined to become an alkylene group represented by the following formula (II)

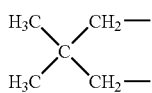
(II)

and form the following cyclic structure B together with the oxygen atoms and the phosphorus atom;

Cyclic structure B:

(in cyclic structure B, —$R^3$—$R^4$— is the alkylene group);
wherein: the compound indispensably has at least one of cyclic structure A and cyclic structure B; and $R^{20}$ is a linking group having formula 67:

(Formula 67)

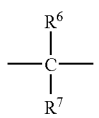

(in formula 67, $R^6$ and $R^7$ may be identical to or different from each other; are either hydrogen, a $C_{1-6}$ alkyl group, or $C_{6-11}$ aryl group; or $R^6$ and $R^7$ may be combined to become a $C_{4-10}$ alkylene group which may have one or more substituents, the $C_{4-10}$ alkylene group forming the following cyclic structure together with the carbon atom

;

and
a total number of carbons of $R^6$ and $R^7$ is 0 to 12).

9. A flame retardant agent for a resin formed of a compound represented by the following formula (III):

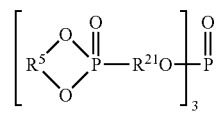
(III)

wherein, in formula (III), $R^5$ is a $C_{2-9}$ alkylene group, and $R^{21}$ is a linking group having formula 89:

(Formula 89)

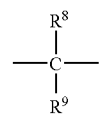

(in formula 89, $R^8$ and $R^9$ may be identical to or different from each other; are either hydrogen, a $C_{1-6}$ alkyl group, or $C_{6-11}$ aryl group; or $R^8$ and $R^9$ may be combined to become a $C_{4-10}$ alkylene group which may have one or more substituents, the $C_{4-10}$ alkylene group forming the following cyclic structure together with the carbon atom

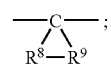;

and
a total number of carbons of $R^8$ and $R^9$ is 0 to 12).

10. A flame retardant agent according to claim 8, which is used for flame retardation of a polyester fiber.

11. A flame retardant agent according to claim 9, which is used for flame retardation of a polyester fiber.

12. A polyester fiber processed with a flame retardant agent, the flame retardant agent being formed of a compound represented by the following formula (I):

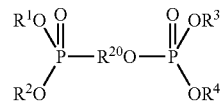
(I)

wherein, in formula (I), $R^1$, $R^2$, $R^3$ and $R^4$ are identical to or different from each other, and are:
  a $C_{2-8}$ alkyl group having a straight or branched chain,
  a $C_{5-10}$ cycloalkyl group which may have one or more substituents, or
  a $C_{6-15}$ aryl group which may have one or more substituents; or
$R^1$ and $R^2$ are combined to become an alkylene group represented by the following formula (II)

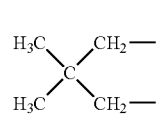
(II)

and form the following cyclic structure A together with the oxygen atoms and the phosphorus atom;

Cyclic structure A:

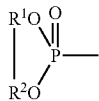

(in cyclic structure A, —R¹—R²— is the alkylene group); or R³ and R⁴ are combined to become am alkylene group represented by the following formula (II)

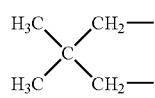
(II)

and form the following cyclic structure B together with the oxygen atoms and the phosphorus atom;

Cyclic structure B:

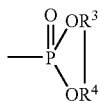

(in cyclic structure B, —R³—R⁴— is the alkylene group); wherein: the compound indispensably has at least one of cyclic structure A and cyclic structure B; and R²⁰ is a linking group having formula 67:

(Formula 67)

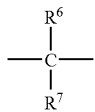

(in formula 67, R⁶ and R⁷ may be identical to or different from each other; are either hydrogen, a $C_{1-6}$ alkyl group, or $C_{6-11}$ aryl group; or R⁶ and R⁷ may be combined to become a $C_{4-10}$ alkylene group which may have one or more substituents, the $C_{4-10}$ alkylene group forming the following cyclic structure together with the carbon atom

and
a total number of carbons of R⁶ and R⁷ is 0 to 12).

13. A polyester fiber according to claim 12, wherein R¹ and R² of the flame retardant agent are combined to form the cyclic structure A and R³ and R⁴ of the flame retardant agent are combined to form the cyclic structure B.

14. A polyester fiber according to claim 12, wherein R²⁰ of the flame retardant agent is either a methylene group, a —CH(CH₃)— group, or a —C(CH₃)₂— group.

15. A polyester fiber according to claim 12, wherein at least one of R³ and R⁴ is a $C_{6-15}$ aryl group when the flame retardant agent has the cyclic structure A, and at least one of R¹ and R² is a $C_{6-15}$ aryl group when the flame retardant agent has the cyclic structure B.

16. A polyester fiber according to claim 12, wherein a content of the flame retardant agent of the polyester fiber is 0.1 to 30% by weight with respect to the total weight of the polyester fiber including the flame retardant agent.

17. A polyester fiber processed with a flame retardant agent, the flame retardant agent being formed of a compound represented by the following formula (III):

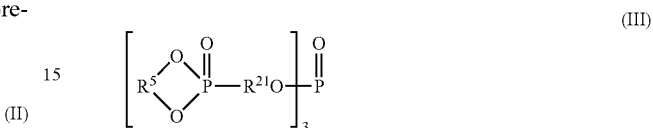
(III)

wherein, in formula (III), R⁵ is a $C_{2-9}$ alkylene group, and R²¹ is a linking group having formula 89:

(Formula 89)

(in formula 89, R⁸ and R⁹ may be identical to or different from each other; are either hydrogen, a $C_{1-6}$ alkyl group, or $C_{6-11}$ aryl group; or R⁸ and R⁹ may be combined to become a $C_{4-10}$ alkylene group which may have one or more substituents, the $C_{4-10}$ alkylene group forming the following cyclic structure together with the carbon atom

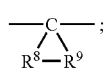

and
a total number of carbons of R⁸ and R⁹ is 0 to 12).

18. A polyester fiber according to claim 17, wherein R²¹ of the flame retardant agent is either a methylene group, a —CH(CH₃)— group, or a —C(CH₃)₂— group.

19. A polyester fiber according to claim 17, wherein R⁵ of the flame retardant agent is the following formula (IV)

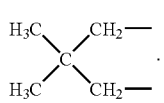
(IV)

20. A polyester fiber according to claim 17, wherein a content of the flame retardant agent of the polyester fiber is 0.1 to 30% by weight with respect to the total weight of the polyester fiber including the flame retardant agent.

21. A method for flame-retarding a polyester fiber, comprising the step of processing the polyester fiber with a flame retardant agent according to claim 10.

22. A method for flame-retarding a polyester fiber, comprising the step of processing the polyester fiber with a flame retardant agent according to claim 11.

23. A flame retardant agent according to claim 8, which is used for flame retardation of a polyurethane resin.

24. A flame retardant agent according to claim 9, which is used for flame retardation of a polyurethane resin.

25. A flame retardant polyurethane resin composition, comprising (a) a flame retardant agent, (b) a polyol component, and (c) a polyisocyanate component, wherein the flame retardant agent is represented by the following formula (I):

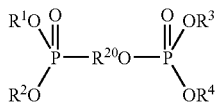
(I)

wherein, in formula (I), $R^1$, $R^2$, $R^3$ and $R^4$ are identical to or different from each other, and are:
- a $C_{2-8}$ alkyl group having a straight or branched chain,
- a $C_{5-10}$ cycloalkyl group which may have one or more substituents, or
- a $C_{6-15}$ aryl group which may have one or more substituents; or $R^1$ and $R^2$ are combined to become an alkylene group represented by the following formula (II)

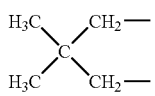
(II)

and form the following cyclic structure A together with the oxygen atoms and the phosphorus atom;

Cyclic structure A:

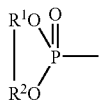

(in cyclic structure A, —$R^1$—$R^2$— is the alkylene group); or $R^3$ and $R^4$ are combined to become an alkylene group represented by the following formula (II)

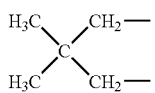
(II)

and form the following cyclic structure B together with the oxygen atoms and the phosphorus atom;

Cyclic structure B:

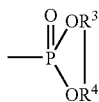

(in cyclic structure B, —$R^3$—$R^4$— is the alkylene group);
wherein: the compound indispensably has at least one of cyclic structure A and cyclic structure B; and $R^{20}$ is a linking group having formula 67:

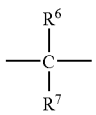
(Formula 67)

(in formula 67, $R^6$ and $R^7$ may be identical to or different from each other; are either hydrogen, a $C_{1-6}$ alkyl group, or $C_{6-11}$ aryl group: or $R^6$ and $R^7$ may be combined to become a $C_{4-10}$ alkylene group which may have one or more substituents, the $C_{4-10}$ alkylene group forming the following cyclic structure together with the carbon atom

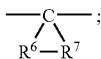;

and
a total number of carbons of $R^6$ and $R^7$ is 0 to 12).

26. A composition according to claim 25, further comprising (d) a catalyst, (e) a silicone foam stabilizer, and (f) a foaming agent.

27. A composition according to claim 25, wherein $R^1$ and $R^2$ of the flame retardant agent are combined to form the cyclic structure A and $R^3$ and $R^4$ of the flame retardant agent are combined to form the cyclic structure B.

28. A composition according to claim 25, wherein $R^{20}$ of the flame retardant agent is either a methylene group, a —CH($CH_3$)— group, or a —C($CH_3$)$_2$— group.

29. A composition according to claim 25, wherein at least one of $R^3$ and $R^4$ is a $C_{6-15}$ aryl group when the flame retardant agent has the cyclic structure A, and at least one of $R^1$ and $R^2$ is a $C_{6-15}$ aryl group when the flame retardant agent has the cyclic structure B.

30. A composition according to claim 25, wherein the polyol component is selected from the group consisting of polyether polyol, polyester polyol, and polymer polyol.

31. A composition according to claim 25, wherein the polyisocyanate component is selected from the group consisting of tolylene diisocyanate (TDI) and diphenylmethane 4,4'-diisocyanate (MDI).

32. A composition according to claim 25, wherein a content of the flame retardant agent is 0.1 to 60 parts by weight with respect to 100 parts by weight of the polyol component.

33. A composition according to claim 25, further comprising, as an antioxidant, (g) a hydroquinone compound represented by the following general formula (VII) and/or trivalent organic phosphorus compound:

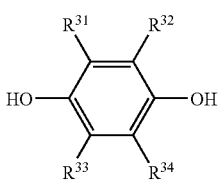
(VII)

(in the formula, $R^{31}$, $R^{32}$, $R^{33}$ and $R^{34}$ are each a hydrogen atom or a $C_{1-14}$ alkyl group).

34. A flame retardant polyurethane resin composition, comprising (a) a flame retardant agent, (b) a polyol component, and (c) a polyisocyanate component, wherein the flame retardant agent is represented by the following formula (III):

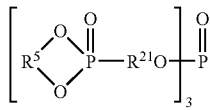 (III)

wherein, in formula (III), $R^5$ is a $C_{2-9}$ alkylene group, and $R^{21}$ is a linking group having formula 89:

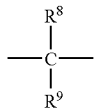 (Formula 89)

(in formula 89, $R^8$ and $R^9$ may be identical to or different from each other; are either hydrogen, a $C_{1-6}$ alkyl group, or $C_{6-11}$ aryl group; or $R^8$ and $R^9$ may be combined to become a $C_{4-10}$ alkylene group which may have one or more substituents, the $C_{4-10}$ alkylene group forming the following cyclic structure together with the carbon atom

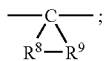

and a total number of carbons of $R^8$ and $R^9$ is 0 to 12).

35. A composition according to claim 34, further comprising (d) a catalyst, (e) a silicone foam stabilizer, and (f) a foaming agent.

36. A composition according to claim 34, wherein $R^{21}$ of the flame retardant agent is either a methylene group, a —CH(CH$_3$)— group, or a —C(CH$_3$)$_2$— group.

37. A composition according to claim 34, wherein $R^5$ of the flame retardant agent is the following formula (IV)

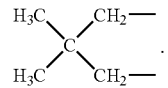 (IV)

38. A composition according to claim 34, wherein the polyol component is selected from the group consisting of polyether polyol, polyester polyol, and polymer polyol.

39. A composition according to claim 34, wherein the polyisocyanate component is selected from the group consisting of tolylene diisocyanate (TDI) and diphenylmethane 4,4'-diisocyanate (MDI).

40. A composition according to claim 34, wherein a content of the flame retardant agent is 0.1 to 60 parts by weight with respect to 100 parts by weight of the polyol component.

41. A composition according to claim 34, further comprising, as an antioxidant, (g) a hydroquinone compound represented by the following general formula (VII) and/or trivalent organic phosphorus compound:

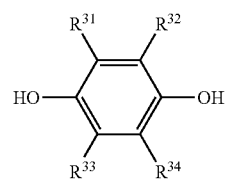 (VII)

(in the formula, $R^{31}$, $R^{32}$, $R^{33}$ and $R^{34}$ are each a hydrogen atom or a $C_{1-14}$ alkyl group).

42. A molded product which is obtained by molding the composition according to claim 25.

43. A molded product which is obtained by molding the composition according to claim 34.

44. A method for molding a flame retardant polyurethane foam, comprising the step of foaming a composition according to claim 25.

45. A method for molding a flame retardant polyurethane foam, comprising the step of foaming a composition according to claim 34.

* * * * *